United States Patent
Huebsch et al.

(10) Patent No.: US 10,851,344 B2
(45) Date of Patent: Dec. 1, 2020

(54) REVERSIBLE STENCILS FOR FABRICATING MICRO-TISSUES

(71) Applicants: The Regents of The University of California, Oakland, CA (US); The J. David Gladstone Institutes, a testamentary trust established under the Will of J. David Gladstone, San Francisco, CA (US)

(72) Inventors: Nathaniel Huebsch, San Bruno, CA (US); Bruce Conklin, San Francisco, CA (US); Kevin E. Healy, Moraga, CA (US); Peter Loskill, Berkeley, CA (US)

(73) Assignees: The J. David Gladstone Institutes, a testamentary trust established under the Will of J. David Gladstone, San Francisco, CA (US); The Regents of The University of California, Oakland, CA (US)

( * ) Notice: Subject to any disclaimer, the term of this patent is extended or adjusted under 35 U.S.C. 154(b) by 172 days.

(21) Appl. No.: 15/329,035

(22) PCT Filed: Aug. 7, 2015

(86) PCT No.: PCT/US2015/044232
§ 371 (c)(1),
(2) Date: Jan. 25, 2017

(87) PCT Pub. No.: WO2016/022930
PCT Pub. Date: Feb. 11, 2016

(65) Prior Publication Data
US 2017/0211044 A1  Jul. 27, 2017

Related U.S. Application Data

(60) Provisional application No. 62/034,210, filed on Aug. 7, 2014.

(51) Int. Cl.
| | | |
|---|---|---|
| C12N 5/077 | (2010.01) |
| C12M 3/00 | (2006.01) |
| C12M 1/12 | (2006.01) |
| C12M 1/32 | (2006.01) |

(52) U.S. Cl.
CPC ........... *C12N 5/0657* (2013.01); *C12M 21/08* (2013.01); *C12M 23/12* (2013.01); *C12M 25/14* (2013.01); *C12N 2533/30* (2013.01); *C12N 2535/10* (2013.01)

(58) Field of Classification Search
None
See application file for complete search history.

(56) References Cited

U.S. PATENT DOCUMENTS

| | | | |
|---|---|---|---|
| 2002/0173033 A1 | 11/2002 | Hammerick et al. | |
| 2004/0191891 A1* | 9/2004 | Tsinberg | B01D 61/18 506/9 |
| 2011/0086427 A1 | 4/2011 | Faris et al. | |
| 2013/0196435 A1 | 8/2013 | Lee et al. | |

FOREIGN PATENT DOCUMENTS

| | | |
|---|---|---|
| DE | 102010022675 | 12/2011 |
| EP | 1840207 B1 | 5/2018 |
| WO | 2013151755 | 10/2013 |
| WO | 2014021778 | 2/2014 |
| WO | WO-2014085933 A1 | 6/2014 |
| WO | WO-2016022930 A1 | 2/2016 |

OTHER PUBLICATIONS

Gai et al., Generation and characterization of functional cardiomyocytes using induced pluripotent stem cells derived from human fibroblasts, Cell Biology International vol. 33, (2009): pp. 1184-1193.*
Legant et al., PNAS, Jun. 23, 2009, vol. 106, No. 25, pp. 10097-10102 (Year: 2009).*
Svoronos et al., Tissue Engineering: Part A, vol. 20, No. 7 and 8, 2014, pp. 1134-1144 (Year: 2014).*
"European Application Serial No. 15828943.9, Extended European Search Report dated Feb. 13, 2018", 7 pgs.
Albert, Folch, "Microfabricated elastomeric stencils for micropatterning cell cultures", Journal of Biomedical Materials Research. PA, Wiley Periodicals Inc, Hoboken, NY, US, vol. 52, No. 2, (Aug. 1, 2000), 346-353.
"International Application Serial No. PCT/US2015/044232, International Preliminary Report on Patentability dated Feb. 16, 2017", 12 pgs.
"European Application Serial No. 158289419, Response filed Sep. 12, 2017 to Communication pursuant to Rules 161(2) and 162 EPC", 7 pgs.
"International Application Serial No. PCT/US2015/044232, International Search Report dated Nov. 9, 2015", 2 pgs.
"International Application Serial No. PCT/US2015/044232, Written Opinion dated Nov. 9, 2015", 10 pgs.
"European Application Serial No. 15828943.9, Response filed Aug. 20, 2018 to Extended European Search Report dated Feb. 13, 2018", 15 pgs.
"European Application Serial No. 15828943.9, Communication Pursuant to Article 94(3) EPC dated Mar. 6, 2019", 7 pgs.
"European Application Serial No. 15828943.9, Response filed Jul. 3, 2019 to Communication Pursuant to Article 94(3) EPC dated Mar. 6, 2019", 25 pgs.
"European Application U.S. Appl. No. 15/828,943.9, Communication Pursuant to Article 94(3) EPC dated Aug. 4, 2020", 5 pgs.

* cited by examiner

*Primary Examiner* — Scott Long
*Assistant Examiner* — Evelyn Y Pyla
(74) *Attorney, Agent, or Firm* — Schwegman Lundberg & Woessner, P.A.

(57) ABSTRACT

The invention relates to devices, methods, kits, and compositions for in vitro generation of three-dimensional microtissues that are accurate models of heart, skeletal muscle, neuronal, and other tissues.

25 Claims, 43 Drawing Sheets

BRIGHTFIELD
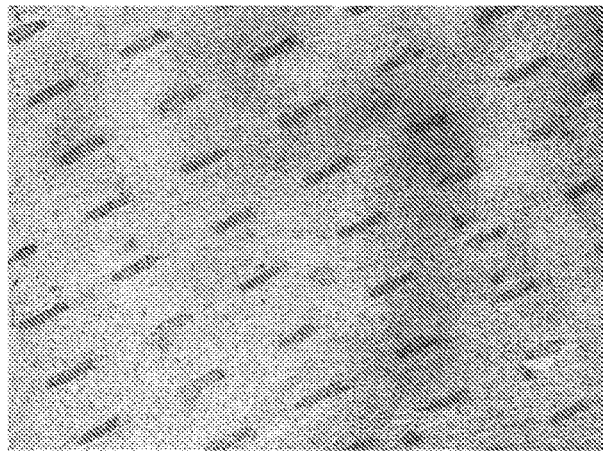
Fig. 1D1
mCHERRY
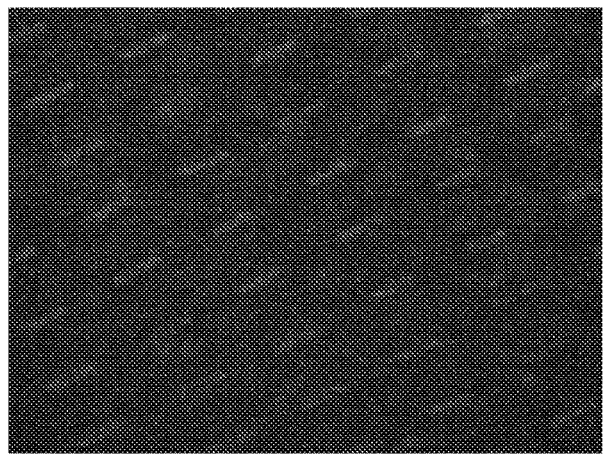
Fig. 1D2

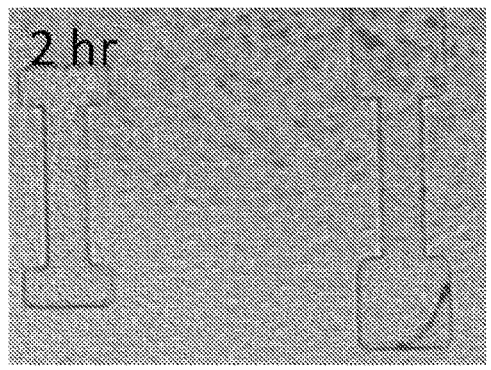
*Fig. 3A1*
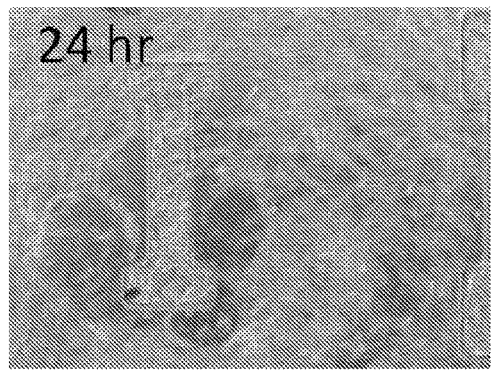
*Fig. 3A2*
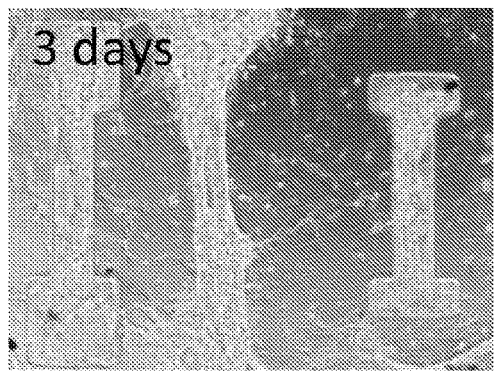
*Fig. 3A3*
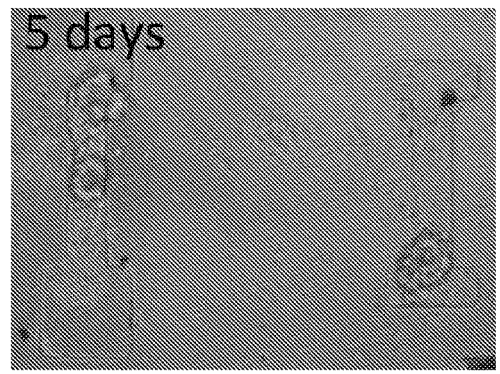
*Fig. 3A4*

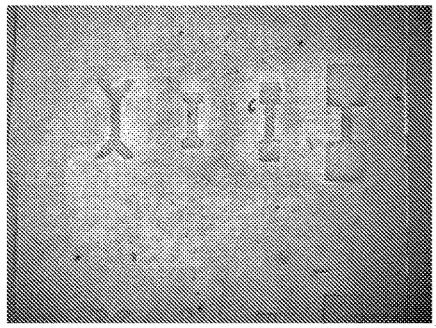
2 HR
*Fig. 3D1*
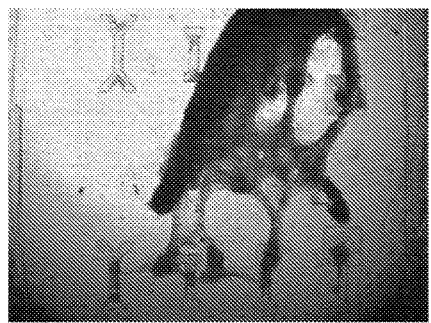
5 DAYS
*Fig. 3D2*
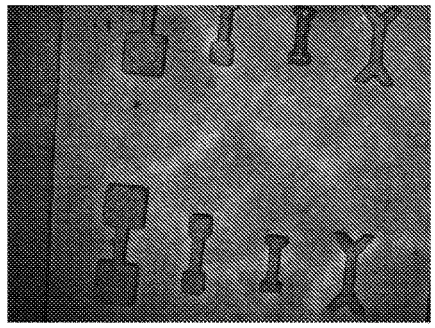
2 HR
*Fig. 3E1*
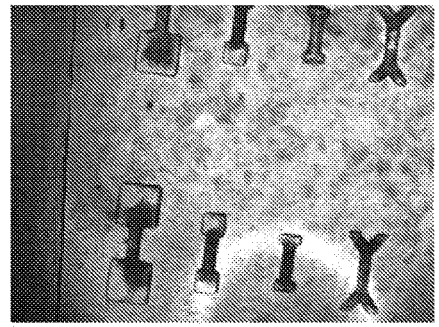
5 DAYS
*Fig. 3E2*

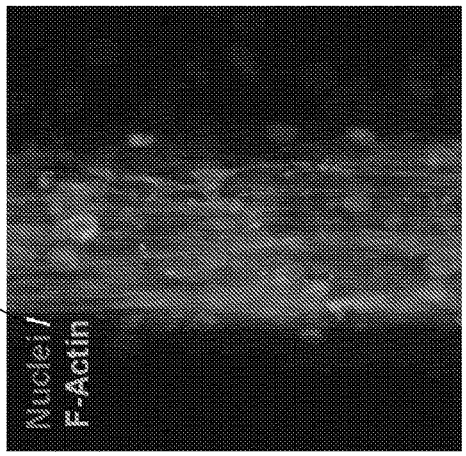
Fig. 3F3
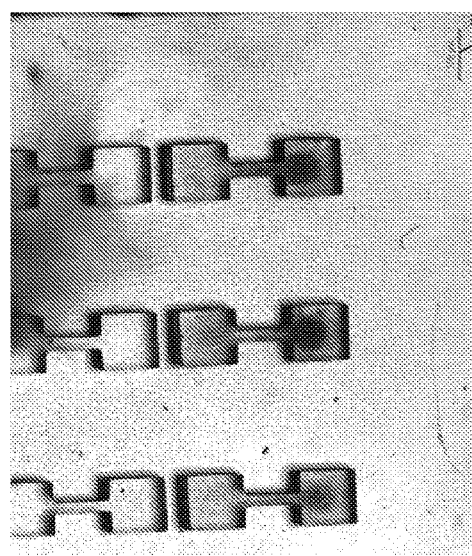
Fig. 3F2
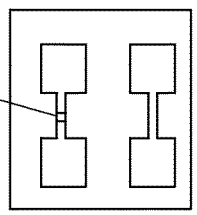
Fig. 3F1

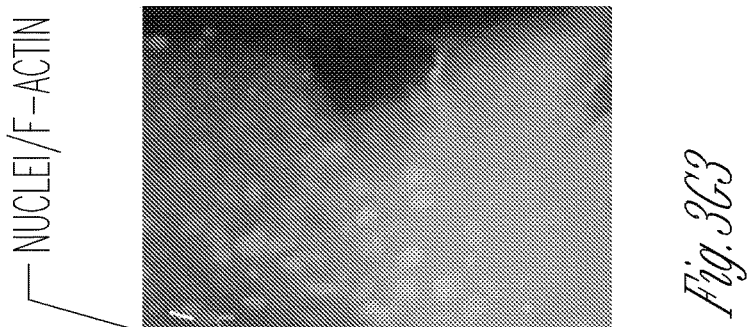
Fig. 3G3
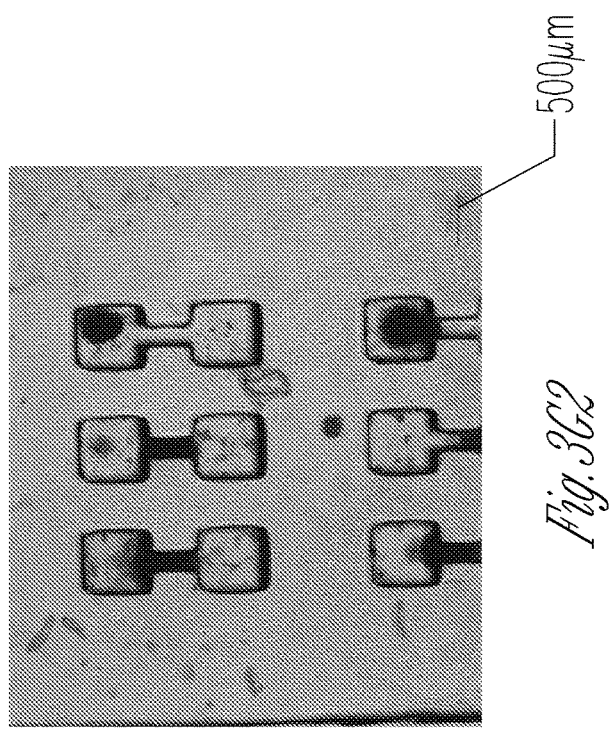
Fig. 3G2
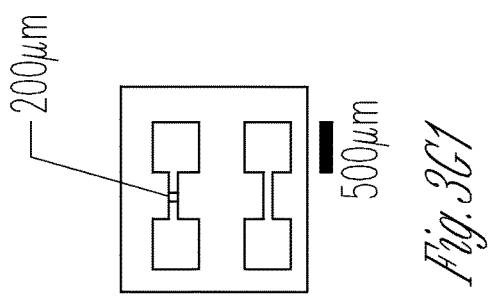
Fig. 3G1

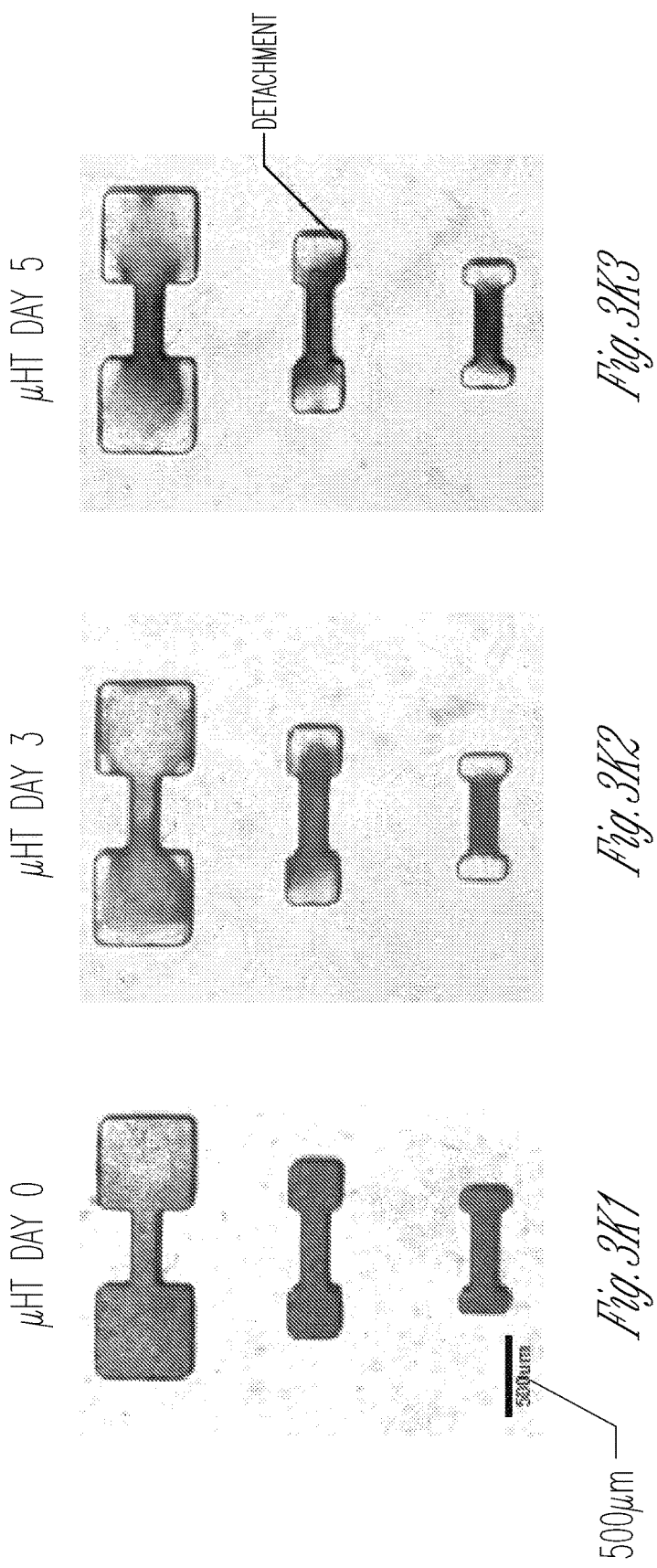
Fig. 3K1  Fig. 3K2  Fig. 3K3

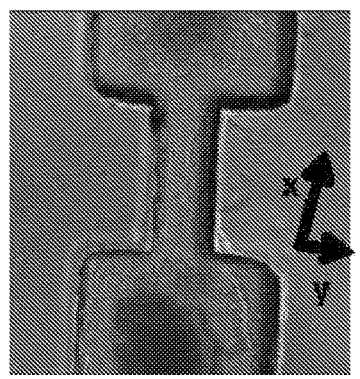
Fig. 4A1
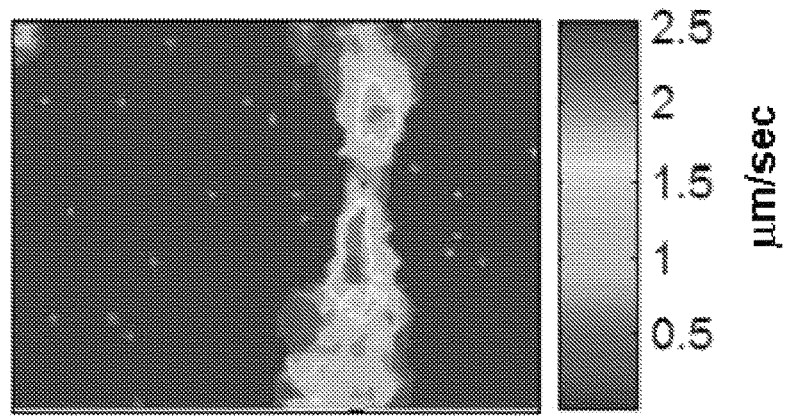
Averaged x-contraction
Fig. 4A2
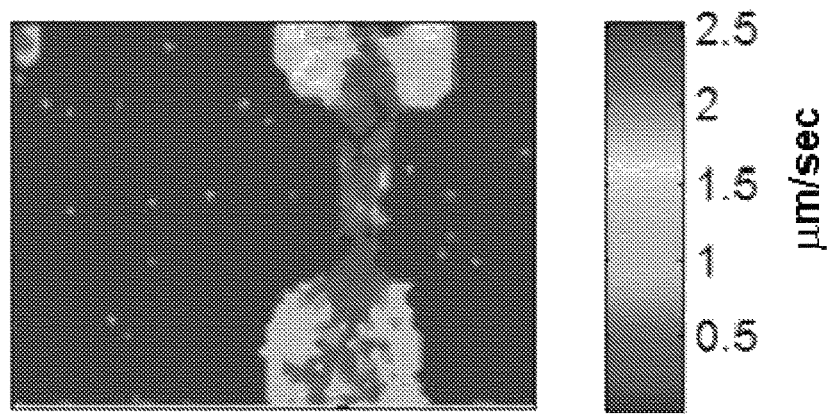
Averaged y-contraction
Fig. 4A3

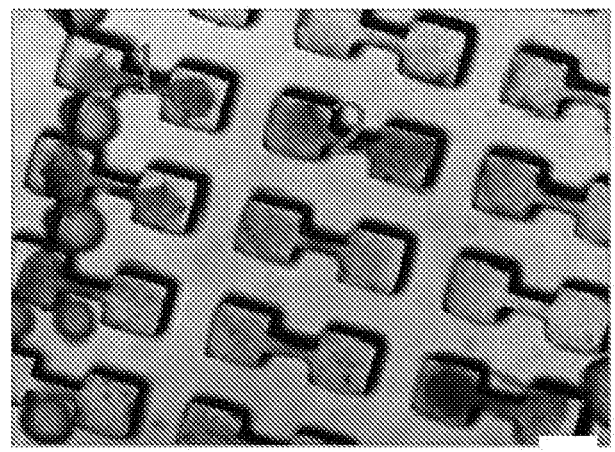
Fig. 4B1
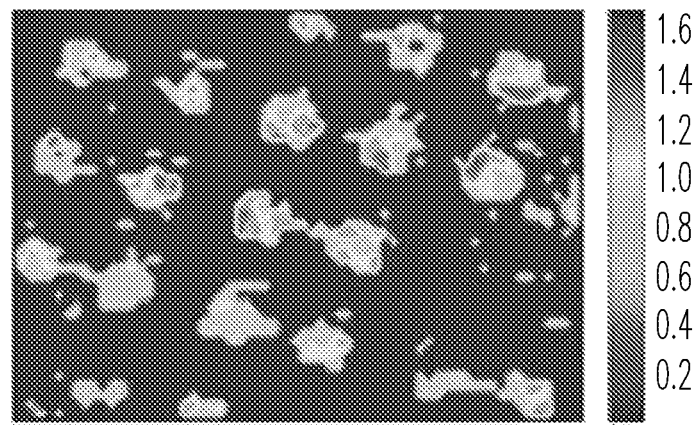
Fig. 4B2

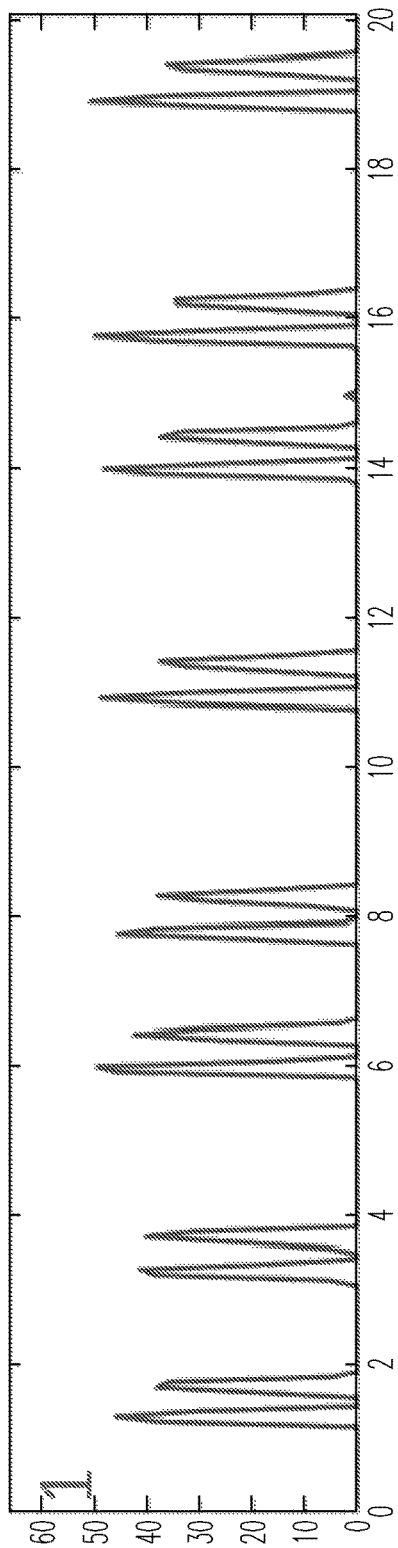
Fig. 4B3
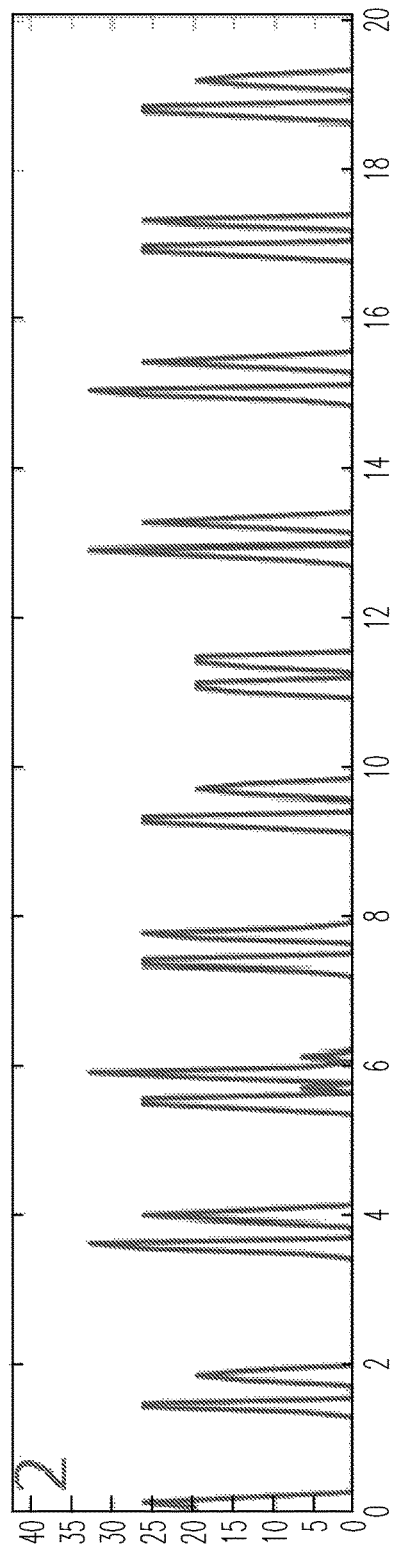
Fig. 4B4

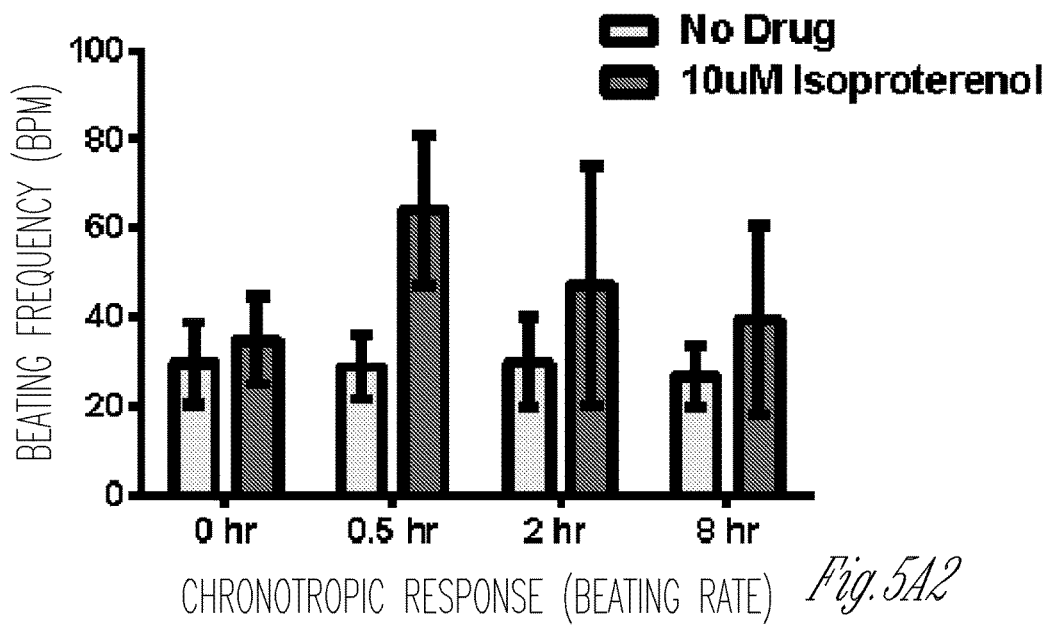
Fig.5A1
Fig.5A2
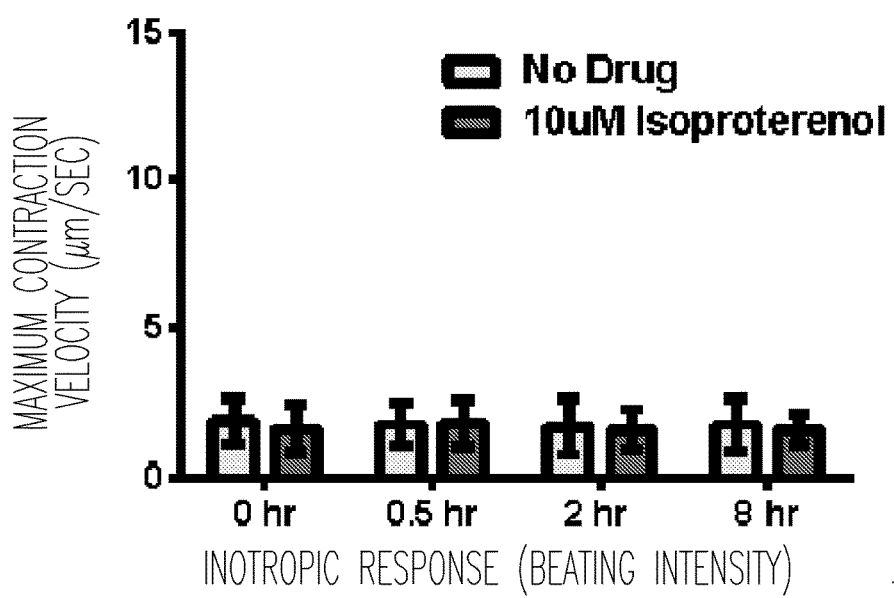
Fig.5A3

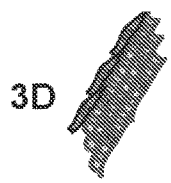
Fig.5A4
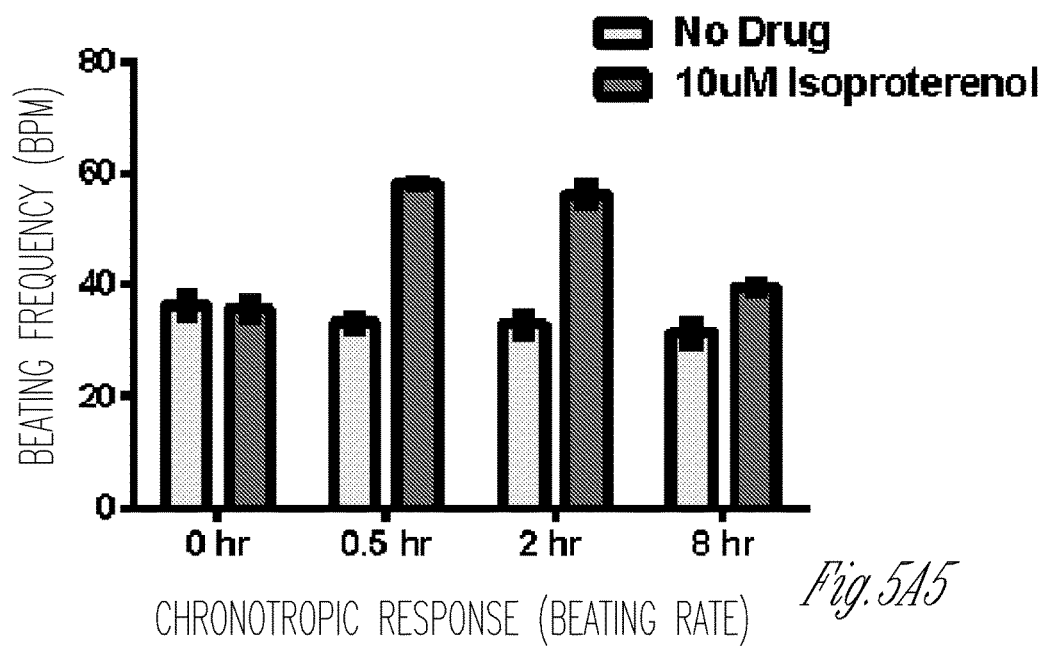
Fig.5A5
CHRONOTROPIC RESPONSE (BEATING RATE)
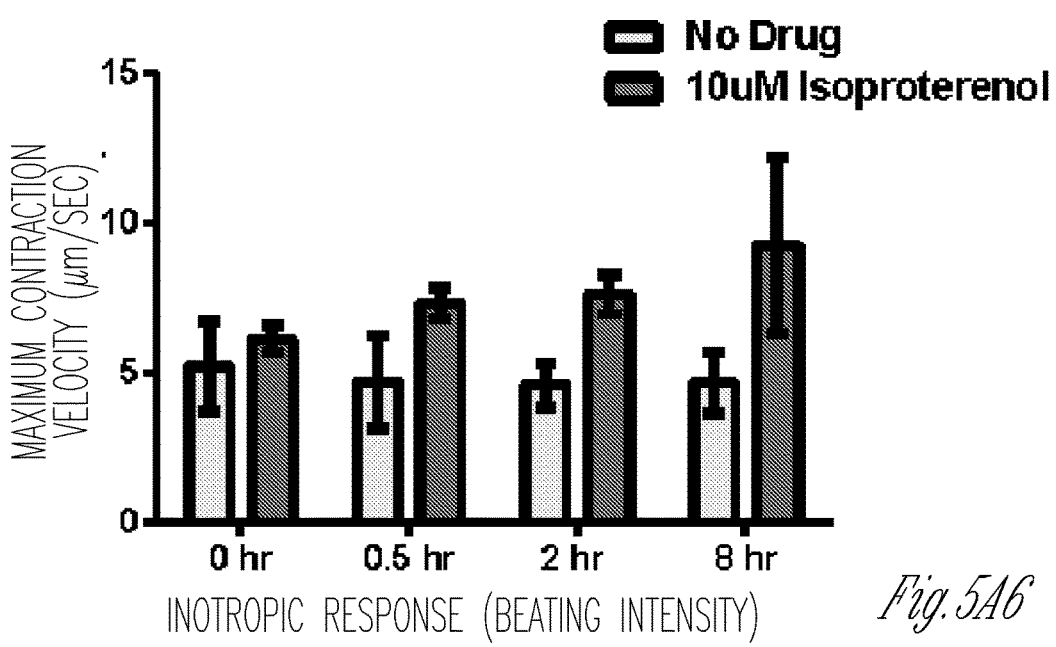
Fig.5A6
INOTROPIC RESPONSE (BEATING INTENSITY)

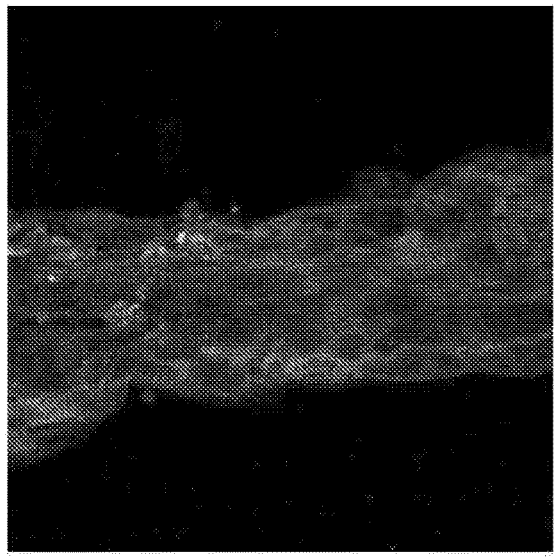
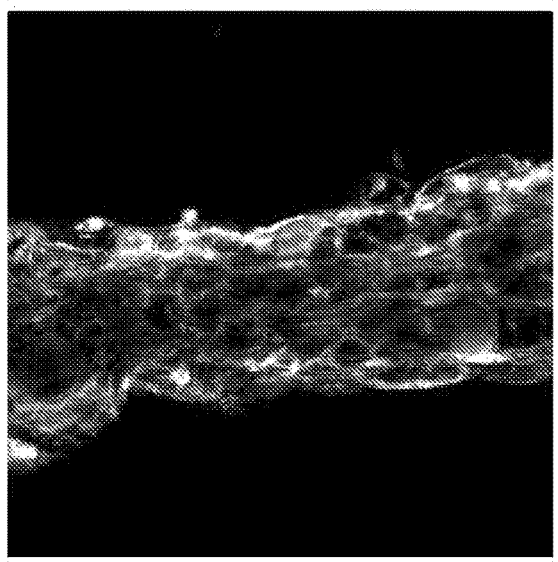
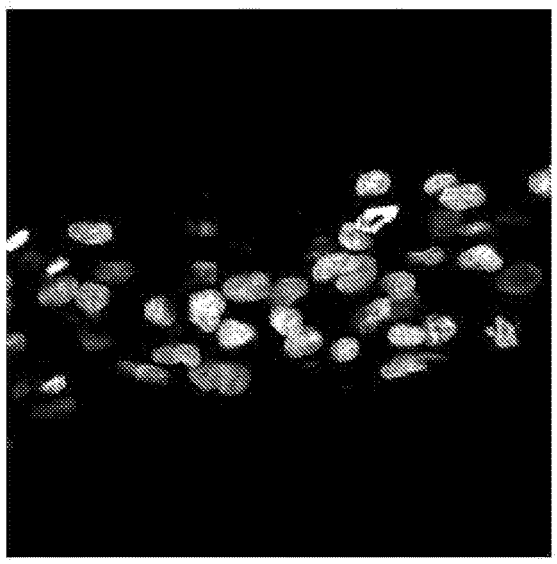
Fig. 6C Actn2 Antibody (Sarcomeres)
Fig. 6B Fitc-Wheat Germ Agglutinin (Membranes)
Fig. 6A Hoescht (nuclei)

Fitc-Wheat Germ Agglutinin (Membranes);

Vinculin antibody (Cell-cell adhesions)

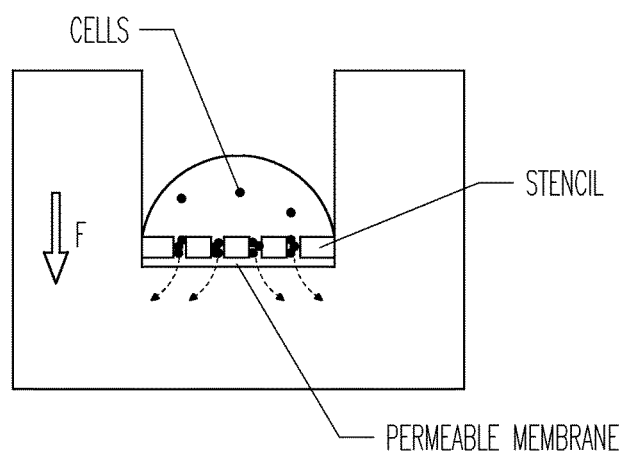
*Fig. 7A*
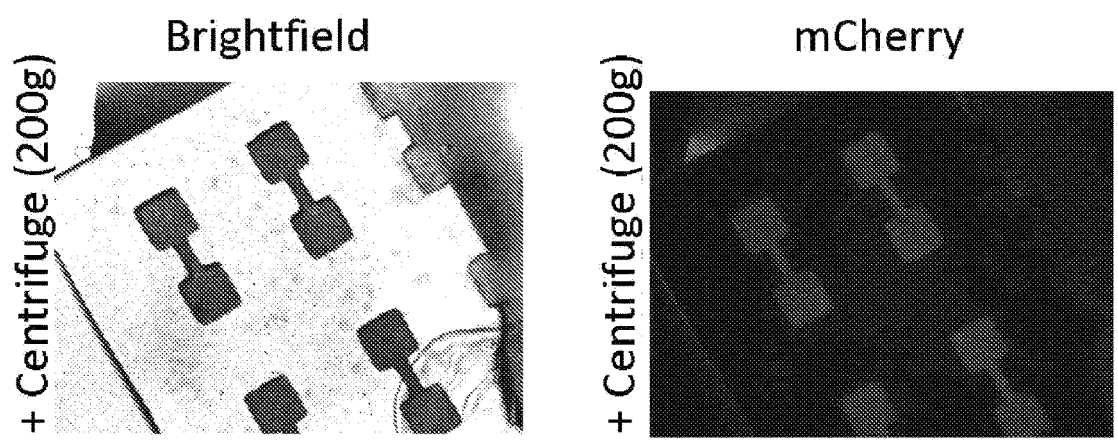
*Fig. 7B1*  *Fig. 7B2*

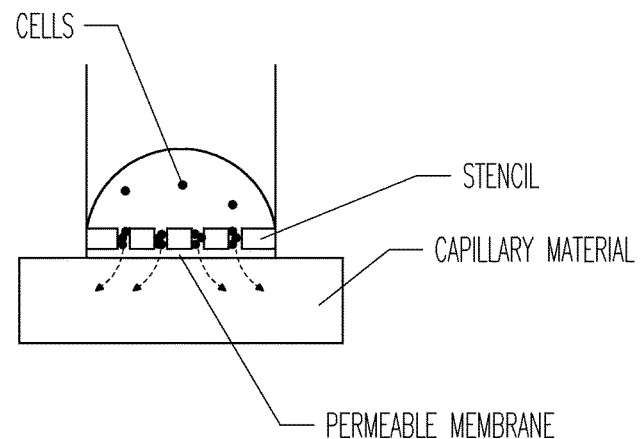
Fig. 7C
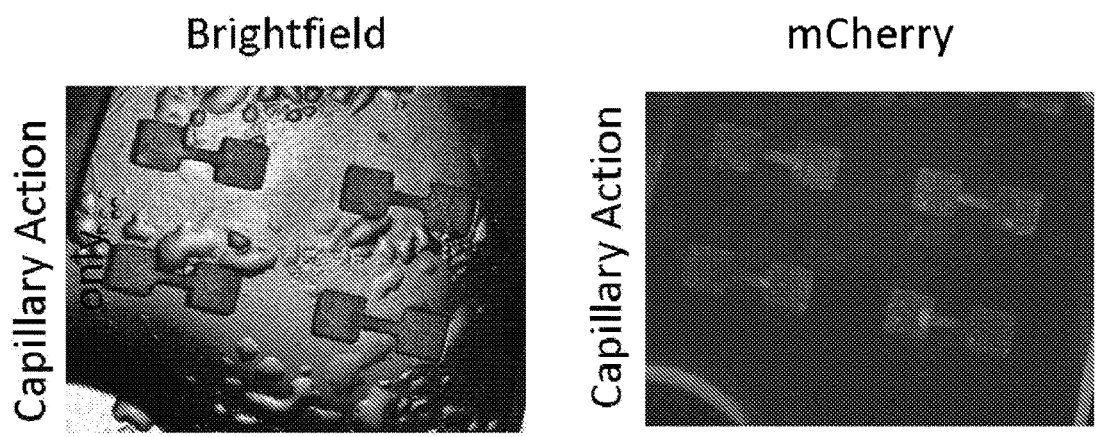
Fig. 7D1          Fig. 7D2

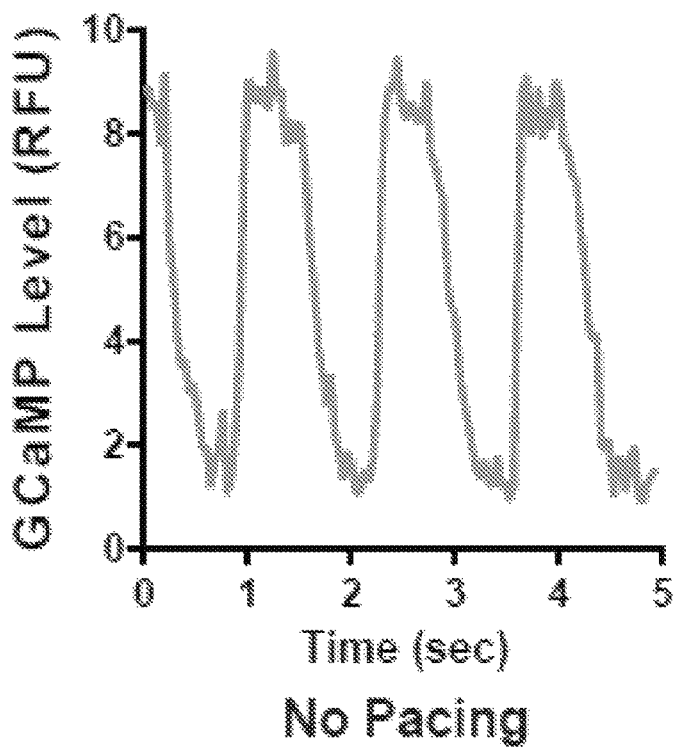
Fig.8C1
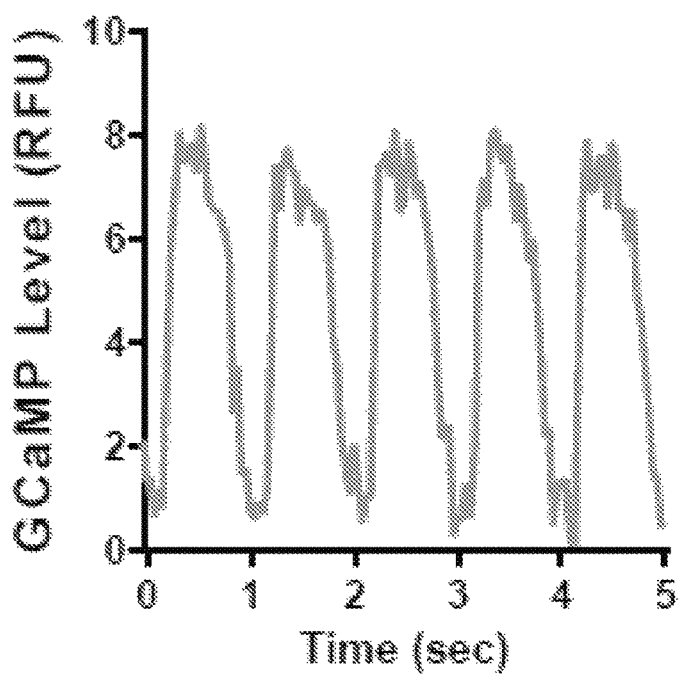
Fig.8C2

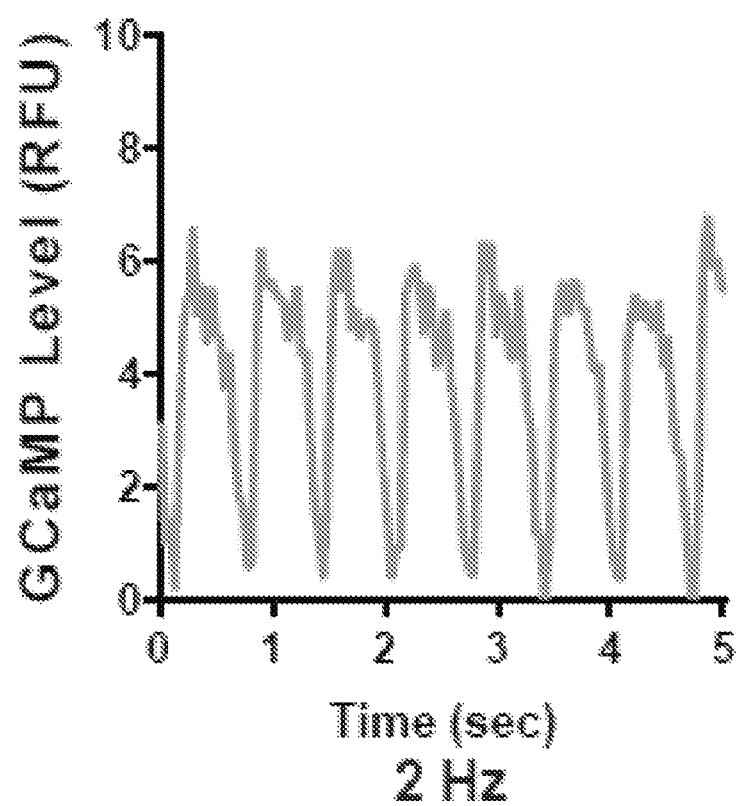
Fig. 8C3

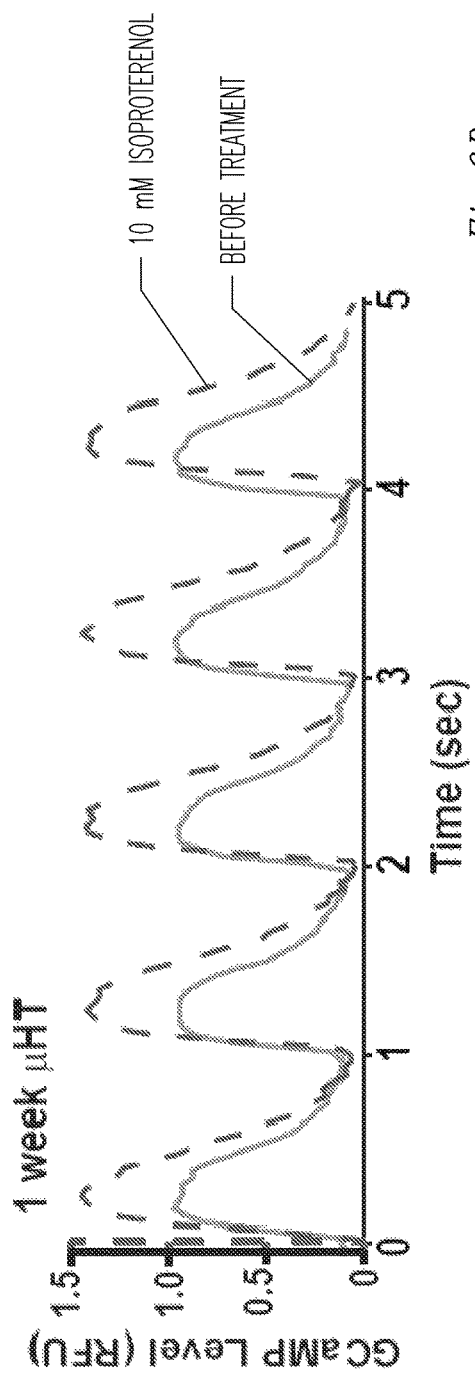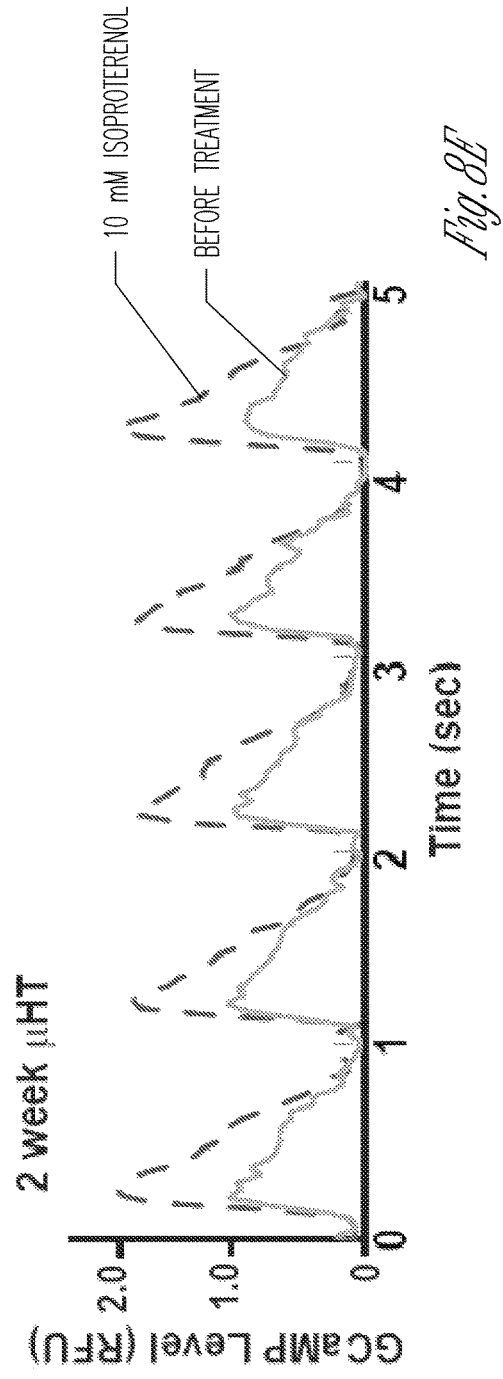
Fig. 8D
Fig. 8E

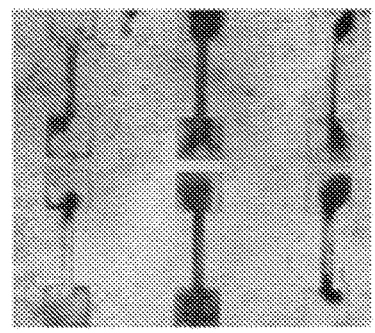
*Fig. 9A*
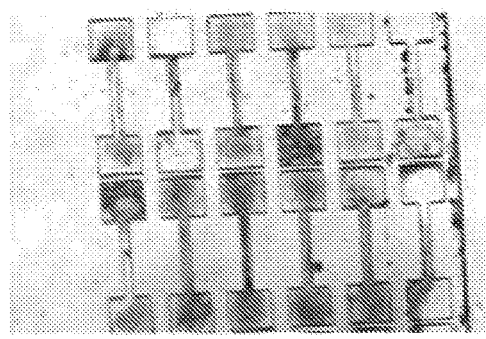 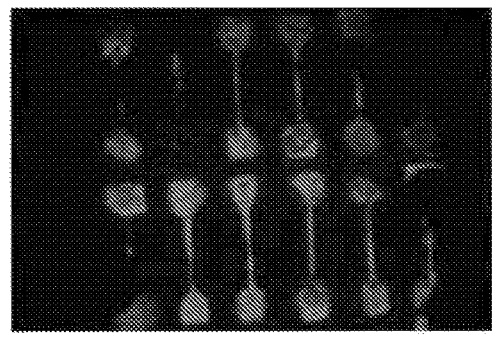
*Fig. 9B1* *Fig. 9B2*
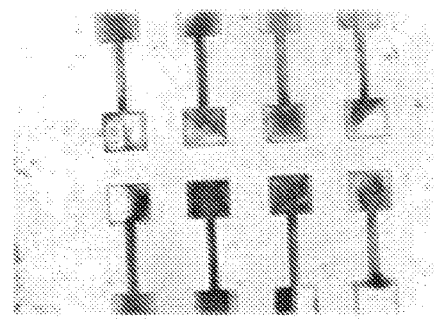 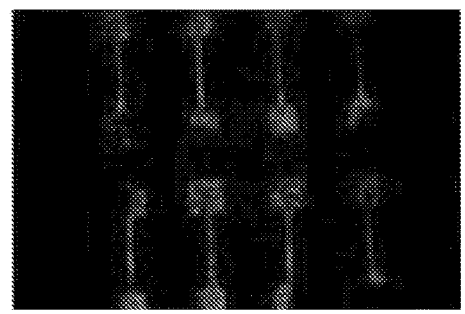
*Fig. 9C1* *Fig. 9C2*

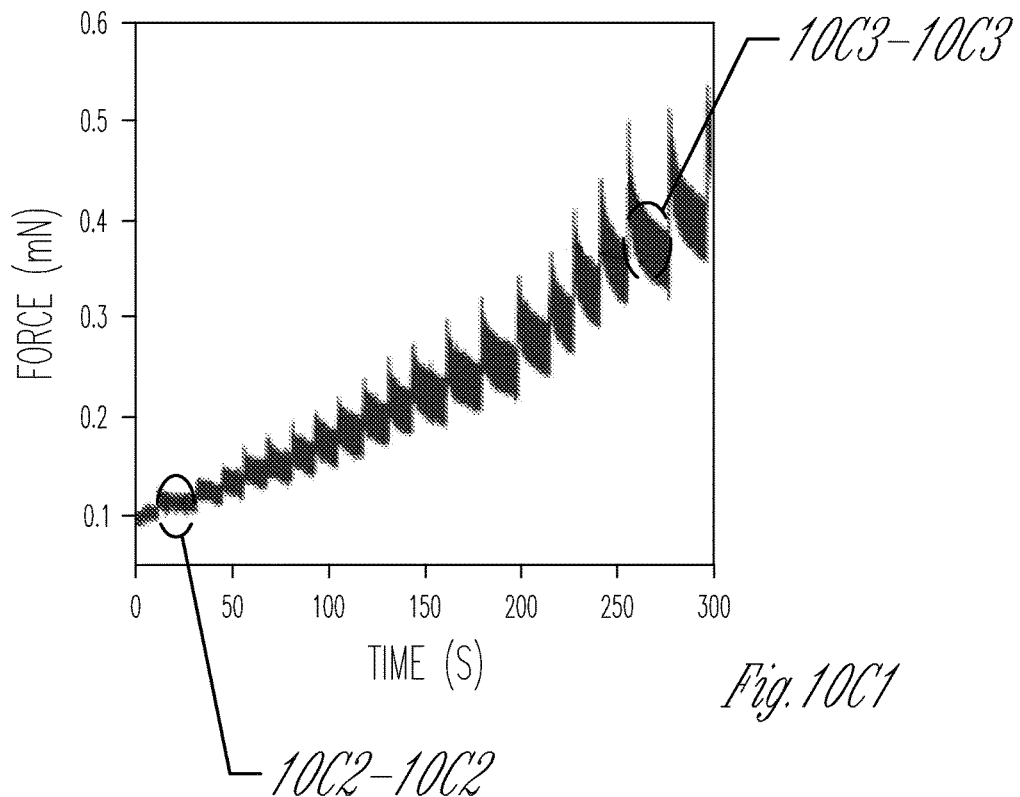
Fig.10C1
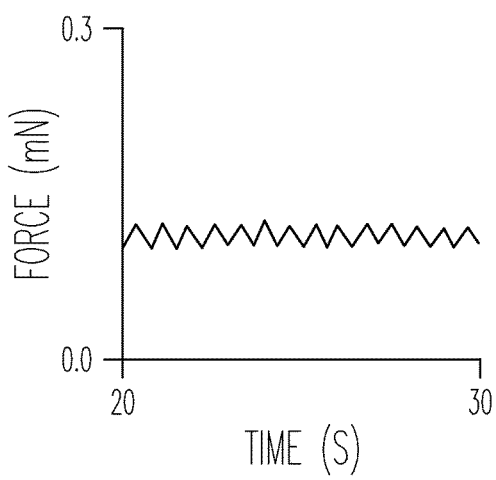
Fig.10C2
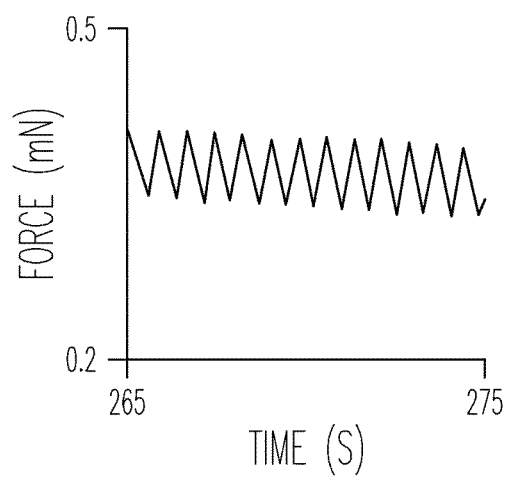
Fig.10C3

REVERSIBLE STENCILS FOR FABRICATING MICRO-TISSUES

CROSS REFERENCE TO RELATED APPLICATIONS

This application is a U.S. National Stage Filing under 35 U.S.C. 371 from International Patent Application Serial No. PCT/US2015/044232. filed Aug. 7, 2015, published on Feb. 11, 2016 as WO 2016/022930 A1. which application claims the benefit of priority to the filing date of U.S. Provisional Application Ser. No. 62/034,210, filed Aug. 7, 2014, the contents of which are specifically incorporated herein by reference in their entireties.

GOVERNMENT SUPPORT

This invention was made with government support under TR000487 awarded by the National Institutes of Health. The government has certain rights in the invention.

BACKGROUND

Chemical substances such as pharmaceuticals, industrial chemicals, biocides, food and feed preservatives, as well as cosmetics have to be assessed for toxicity in studies that typically involve the use of animals. However, animal-based tests are often poor models for predicting the effects of such substances in humans. Such animal-based tests are also ethically questionable, costly, and time consuming. For these reasons both the European Commission and US regulatory bodies encourage use of non-animal models for safety and efficacy testing. However, such testing should be based on predictive, human cell organotypic models that mimic as closely as possible the conditions in humans (*Toxicity Testing in the 21st Century: A Vision and a Strategy*, 2007).

Moreover, drug testing could be expedited if appropriate human tissue models were available, for example, models that appropriately and realistically model the types of mutations and defects present in the hearts, muscles, nervous systems and other tissues of people with cardiac, muscular, or neuronal diseases and conditions. The most common heart models used today for safety and pharmacological studies with new pharmaceuticals are animal models and most ex vivo models involve isolated hearts from guinea pigs or rabbis, or Purkinje cells isolated from dogs. No validated in vitro heart model exists that could be used for these purposes.

A few in vitro 3D-cardiac tissue constructs have been developed with both contractile properties and action potentials (Zimmermann et al., *Circulation Research* 90:22 (2002); Akiyama et al., *Int. J. Mol. Sci.* 11: 2910 (2010)). However, such constructs have disadvantages. For example, they typically require large numbers of cells, long periods of time to make tissues for testing, and have only short-lived functional utility (a few weeks). In addition, it is difficult to isolate cells from currently available constructs to perform single cell physiological tests such as patch-clamp electrophysiological tests or identification of the types of genes expressed and their expression levels. In order to effectively utilize in vitro tissue models for the types of extensive tests needed to evaluate the safety and efficacy of drugs, the tissues should be three-dimensional, they should exhibit appropriate physico-chemical properties, they should have dimensions relevant to features of the tissues of interest, and the cells within the tissues should reproducibly express relevant biomarkers. In addition, the tissue models should be available in sufficient numbers for statistically relevant studies, and employ cell numbers and cell types that can reasonably be generated with a reproducible phenotype and purity.

SUMMARY

Methods, devices, cell preparations, and compositions described herein provide clinically relevant tissues that accurately model in vivo human tissues. For example, the tissue model of cardiac function described herein not only exhibits beating frequency, beating strength, electrical activity, and different channel activities of functional human cardiac tissue, but can be quickly generated in large numbers appropriate for large scale, high throughput screening of drug candidates.

One aspect of the invention is a device for confining mammalian cells and forcing tissue alignment and self-assembly, comprising:
  a cell adhesion substrate; and
  a removable elastomeric stencil overlay;
  wherein the elastomeric stencil has one or more cut-out patterned microwells comprising two or more circular, oval, rectangular, square, V-shaped, or triangular holes, each hole joined to an adjacent hole by a canal; and
  wherein the cell adhesion substrate binds cells within at least the holes of the cut-out pattern.

Another aspect of the invention is a method of inducing self-assembly of mammalian cells into one or more three-dimensional micro-tissues comprising
  seeding the mammalian cells into one or more microwells of a device comprising
    a cell adhesion substrate; and
    a removable elastomeric stencil overlay; and
  culturing the seeded cells within the microwells, to thereby induce the self-assembly of the mammalian cells into one or more micro-tissues;
  wherein the elastomeric stencil has one or more cut-out patterned microwells comprising two or more circular, oval, rectangular, square, V-shaped, or triangular holes, each hole joined to an adjacent hole by a canal; and
  wherein the cell adhesion substrate binds cells within at least the holes of the cut-out pattern.

Another aspect of the invention is a kit that includes a device for confining mammalian cells and forcing tissue alignment and self-assembly, comprising:
  a cell adhesion substrate; and
  a removable elastomeric stencil overlay;
  wherein the elastomeric stencil has one or more cut-out patterned microwells comprising two or more circular, oval, rectangular, square, V-shaped, or triangular holes, each hole joined to an adjacent hole by a canal; and
  wherein the cell adhesion substrate binds cells within at least the holes of the cut-out pattern; and
  instructions for making and/or testing micro-tissues in the device(s).

Another aspect of the invention is a kit that includes components for generating a device for confining mammalian cells and forcing tissue alignment and self-assembly, comprising:
  a cell adhesion substrate; and
  components for generating a removable elastomeric stencil overlay;
  wherein the elastomeric stencil has one or more cut-out patterned microwells comprising two or more circular, oval, rectangular, square, V-shaped, or triangular holes, each hole joined to an adjacent hole by a canal; and wherein the cell adhesion substrate binds cells within at least the holes of the cut-out pattern; and instructions for generating the device and/or generating micro-tissues in the device.

DESCRIPTION OF THE FIGURES

FIG. 1A-1D provide a series of schematic diagrams illustrating micro-tissue assembly by elastomeric stencils. FIG. 1A is a schematic diagram illustrating generation of micro-tissues in a stencil. The top left image shows a removable, micro-fabricated poly(dimethyl siloxane) (PDMS) stencil that is sealed in an air-tight, reversible manner to a standard tissue culture substrate (e.g. polystyrene tissue culture plate). Short exposure of the PDMS stencil to 1% Pluronics F68 inhibits protein and cell adhesion to the PDMS, which generates the image at the top right. The next step shows flooding the through-holes of the stencil with extracellular matrix protein (e.g. fibronectin) under a vacuum to promote cell adhesion to the substrate (but not PDMS) generates the lower left image. A concentrated suspension of cells, such as induced pluripotent stem cell-derived-cardiomyocytes and stroma, can then be seeded into microwells of the stencil, which upon incubation generates a micro-tissue. FIG. 1B is a representative image of a micro-tissue array, where the micro-tissues were formed within dumb-bell or dogbone shaped stencils. Scale bar: 500 µm. FIG. 1C is an image of a sample micro-well stencil, with arrows denoting the longitudinal axis along the canal of the micro-well or the shaft of the micro-tissue, and the transverse axis that is perpendicular to the canal of a single dogbone structure. Cells experience more stress along the longitudinal axis. The canal region is the narrow rectangular region, here with a width of 100 µm and a length of 500 µm that connects two 500 µm×500 µm squares. FIG. 1D1-1D2 show images of a stencil made from fibrin gel with microwells containing H2B-mCherry-C2C12 myoblasts. FIG. 1D1 shows a bright field image of the microwells, and FIG. 1D2 shows the same field to illustrate expression of the mCherry fluorescent marker within the micro-tissues generated within the microwells.

FIG. 2A is a schematic of an exemplary hydrogel inversion process starting with the micro-tissue within the stencil. Micro-tissues are subjected to physiologic analysis (e.g., contraction frequency). Next, either after or without cell fixation, a hydrogel is cast above the array. Once cross-linked, the hydrogel is peeled off the substrate, taking the micro-tissue array with it. The micro-tissue attached to the hydrogel can then be analyzed, for example, by sectioning, and/or by immunocytochemistry (ICC) or by fluorescence in situ hybridization (FISH). FIG. 2B is a representative image of a micro-tissue array embedded into agarose hydrogel. FIG. 1C shows hematoxylin/eosin stained sections obtained from the hydrogel shown in FIG. 2B. Note that the original orientation and relative positions of individual micro-tissues are preserved. FIG. 2D is a representative image of live C2C12 myoblasts after inversion of a living micro-tissue array into calcium-alginate hydrogel.

FIG. 3A-3Q illustrate the geometry and formation conditions for dense cardiomyocyte based micro-tissues. FIG. 3A1-3A4 are a series of images illustrating the time-course of micro-tissue assembly within a 100 µm thick PDMS stencil that was not passivated against cell adhesion. Note the initially dense population of cells (2 hours, FIG. 3A1) segregates itself into two distinct populations, either within microwells or above microwells, by 3 days (FIG. 3A3). Because of weak adhesion of the cells to the PDMS surface, the tissue spanning between microwells at day 3 had disappeared by day 5 (FIG. 3A4). FIGS. 3D and 3E are representative images showing the time-course of micro-tissue formation in PDMS stencils that were not passivated against cell adhesion, and where the stencil depth was either 100 µm (FIG. 3D) or 500 µm (FIG. 3E) thick. FIG. 3D1 shows non-passivated microwells that are 100 µm deep at 2 hours after cell seeding, and FIG. 3D2 shows the same microwells at 5 days after cell seeding, illustrating that the cells are not forming micro-tissues within the microwells. FIG. 3E1 shows non-passivated microwells that are 500 µm deep at 2 hours after cell seeding, and FIG. 3E2 shows the same microwells at 5 days after cell seeding, illustrating that the cells sometimes form irregular micro-tissues within the microwells. FIG. 3F1-3F3 show a schematic (FIG. 3F1) illustrating the geometry of 250 µm deep micro-wells, and representative bright-field (FIG. 3F2) or immunofluorescence (FIG. 3F3) images of C2C12 myoblasts within micro-wells with an optimal geometry (100 µm width shaft). FIG. 3G1-3G3 show a schematic (FIG. 3G1) illustrating the geometry of 250 µm deep micro-wells, and representative bright-field (FIG. 3G2) or immunofluorescence (FIG. 3G3) images of C2C12 myoblasts within micro-wells with a sub-optimal geometry (200 µm thick shaft). The cells employed to generate the micro-tissues in FIGS. 3F-3G express nuclear H2B-mCherry (red) and were stained with Alexa Fluor 488 Phalloidin to visualize stress fibers (green). As shown in FIG. 3I, a higher percentage of motion vectors occur along the shaft (0 degrees, circular symbols) when the shaft width is about 50-150 µm, or about 50-100 µm. FIG. 3K1-3K3 illustrates tissue attachment as a function of time within microwells that have different knob areas. The top three images in FIG. 3K1-3K3 are of a cardiomyocyte micro-tissue (µHT) cultured for 0, 3, and 5 days within a microwell that has a knob area of 500 µm×500 µm. The middle three images in FIG. 3K1-3K3 are of a cardiomyocyte micro-tissue (µHT) cultured for 0, 3, and 5 days within a microwell that has a knob area of 250 µm×250 µm. The lower three images in FIG. 3K1-3K3 are of a cardiomyocyte micro-tissue (µHT) cultured for 0, 3, and 5 days within a microwell that has a knob area of 100 µm×250 µm. As illustrated, by day 5 tissues had detached from the microwell that had a knob area of 250 µm×250 µm. FIG. 3M-3Q show a "micro-muscle" formed from a 50:50 mixture of iPSC-derived cardiomyocytes and isogenic iPSC derived fibroblasts. FIG. 3M shows the shaft of the micro-tissue after staining with sarcomeric alpha-actinin (to show the "micro-muscle" structure) and with DAPI to show cellular nuclei. FIG. 3N shows the whole micro-tissue generated from the cardiomyocytes and fibroblasts. FIG. 3N-3Q shows scanning electron micrographs of the micro-muscle. FIG. 3N shows a scanning electron micrograph of the entire micro-muscle. FIG. 3O shows a scanning electron micrograph of the micro-tissue shaft. FIG. 3P shows an expanded view of the micro-tissue shaft, illustrating the alignment of myofilaments therein. FIG. 3Q shows the sub-micron scale filaments within the micro-tissue knob.

FIG. 4A-4H illustrate the physiology and isoproterenol response of control and MYBPC3 deficient iPS-Cardiomyocyte micro-tissues. FIG. 4A1-4A3 show representative images of an iPS-CM micro-tissue, with superimposed motion vectors generated by block-matching software, to indicate the magnitude and direction of movement (FIG. 4A1) and heat-maps depicting the time-averaged intensity of motion along the noted longitudinal x-axis (FIG. 4A2) and transverse y-axis of the dogbone-shaped micro-tissue (FIG. 4A3). FIG. 4B1-4B4 show an exemplary images of a micro-tissue array formed from MYBPC3 deficient iPS-CM and stroma (FIG. 4B1) and heat-map of time-averaged contractility (directionless; FIG. 4B2). Two adjacent microwells are noted, and the magnitude of motion over time is shown (FIG. 4B3 and FIG. 4B4). Note the tracings in FIGS. 4B-3 and 4B4 indicate peak doublets (first peak for contraction, second for relaxation of micro-tissues); counting peak doublets yields beating rate, which is very similar between different micro-tissues. However, as indicated by the imperfect overlap between the motion tracings, the individual tissues are not connected by a syncytium. FIG. 4C graphically illustrates that time-course of the beat-rate responses of either wild type control (diamond symbols) or MYBPC3 deficient iPS-CM micro-tissues (square symbols) after exposure to 10 µm isoproterenol. FIG. 4D graphically illustrates the beat rate at baseline (before drug), or at 30 minutes after adding 10 µm isoproterenol, to MYPBC3$^{+/+}$ wild type control or MYBPC3 deficient micro-tissues after 4 days of exposure to 10 µm isoproterenol (single dose applied once every 24 hr). FIG. 4E-4F are scatter plots indicating the normalized beat-rate of individual cells and clusters of two-dimensional cells (FIG. 4E) compared with micro-tissues (FIG. 4F), after isoproterenol exposure. Note the relatively wide scatter of the two-dimensional cell/cluster samples, which masks the apparent difference in isoproterenol responsiveness between control and MYBPC3 deficient iPS-CM. In contrast, the micro-tissue responses are more synchronous. Error bars: SD, n=5-8. FIG. 4G graphically illustrates the chronotropic responses of different micro-tissues to a first daily 10 uM isoproterenol dose. The micro-tissues were generated within the dogbone-shaped microwells described herein from three different cell types: wild type MYPBC3$^{+/+}$ iPS (circular symbols), heterozygous MYPBC3$^{+/-}$ iPS (square symbols), and null MYPBC3$^{-/-}$ iPS (triangle symbols). FIG. 4H graphically illustrates the chronotropic responses of the different micro-tissues described for FIG. 4G to a fifth daily 10 uM isoproterenol dose.

FIG. 5A-5D illustrate drug responses of control iPS-cardiomyocytes within two-dimensional and three-dimensional tissues. FIG. 5A graphically illustrate the responses of disorganized iPS-CM in two-dimensional cultured cells (2D, FIG. 5A1-A3) and three-dimensional (3D, FIG. 5A4-A6) micro-tissues to 10 µm isoproterenol. Note that this drug causes a robust increase in beat-rate response in three-dimensional micro-tissues (FIG. 5A5), whereas in two-dimensional tissues a large variance amongst samples is apparent, with some samples diminishing in their beat rate within 2 hr of adding the drug (FIG. 5A2. Also note that in three-dimensional tissues, the intensity of beating, measured via the maximum contraction velocity, was affected by isoproterenol (FIG. 5A6). However, isoproterenol did not affect the intensity of beating in two-dimensional monolayers (FIG. 5A3). Error bars: SD, and n=3-8. FIG. 5B graphically illustrates dose responses of control iPS-CM micro-tissues (3D, square symbols) and disorganized cell clusters (2D, diamond symbols). For each drug dose, cells were incubated for 30 minutes, and beating was recorded, before more drug was added to increase the concentration. Error bars: SD, and n>8 (FIG. 5B). FIGS. 5C-5D graphically illustrate the chronotropic response to isoproterenol dosing in non-paced iPS-CM monolayers (FIG. 5C) and micro-tissues (FIG. 5D). FIG. 5C shows the variability in drug (isoproterenol) responses (beat rate) of cell monolayers over time. FIG. 5D graphically illustrates the reproducibility of drug (isoproterenol) responses (beat rate) of the three-dimensional micro-tissues described herein.

FIG. 6A-6E shows images illustrating cellular structures within hydrogel inverted micro-tissues. Representative confocal images of two different micro-tissues (FIG. 6A-6C vs. FIG. 6D-6E) which were cut to 10 µm on a cryotome, and then stained to visualize nuclei (Hoescht; FIG. 6A), membranes (FITC-what germ agglutinin, FIGS. 6B and 6E), sarcomeres (sarcomeric actinin, FIG. 6C), or cell-cell adhesions (vincullin antibody; FIG. 6D).

FIG. 7A-7F illustrates a membrane loading approach to seeded cells in the microwells of the device. FIGS. 7A, 7B, and 7C show schematic diagrams of the membrane loading method. Cells (dots) in media (clearer dome region) are sucked or fall into micro-wells of the device by application of a pressure gradient, centrifugal force, capillary action, vacuum, or gravity across the permeable membrane. The microfluidic channels can facilitate such cellular loading by drawing fluids into and through the microwells and the permeable membrane. FIG. 7B shows bright-field (FIG. 7B1) and fluorescence (FIG. 7B2) images of C2C12 cells that express nuclear mCherry as the cells are loaded into stencils by centrifugal force. FIG. 7D shows bright-field (FIG. 7D1) and fluorescence (FIG. 7D2) images of C2C12 cells that express nuclear mCherry as the cells are loaded into stencils by capillary action. FIG. 7E is a schematic diagram illustrating a stencil on a permeable membrane with a microfluidic channel system below the stencil and the membrane. The channels of microfluidic channel system align with the microwells of the stencil. Cells can be loaded into micro-wells by application of a mild vacuum through the microfluidic channel system. FIG. 7F is a schematic diagram illustrating tissue formation in microwells where microfluidic channels can facilitate introduction of different test agents and/or culture media. The membranes have a pore size of 1 µm.

FIG. 8A-8E illustrate formation of cardiac micro-tissues from induced pluripotent stem cell derived cardiomyocytes that express the calcium indicator, GCaMP6f. FIG. 8A shows an image of a micro-tissue that expresses GCaMP6f (green fluorescence), with a box near the top of the image indicating the region where the fluorescence intensity of the GCaMP reporter (proportional to intracellular calcium concentration) was quantified as shown in FIG. 8B. FIG. 8B shows that the GCaMP6f green fluorescence signal is repetitive and that the intensity of the signal is proportional to intracellular calcium concentration. FIG. 8C1-8C3 show that the micro-tissues described herein respond to electric field pacing. FIG. 8C1 shows calcium flux by micro-tissues that were not subjected to pacing. FIG. 8C2 shows calcium flux by micro-tissues that were subjected pacing in a 1 Hz electrical field, and FIG. 8C3 shows calcium flux by micro-tissues that were subjected pacing in a 2 Hz electrical field. FIG. 8D illustrates calcium flux by 1 week micro-tissues before and after treatment with 10 mM isoproterenol. FIG. 8E illustrates calcium flux by 2 week micro-tissues before and after treatment with 10 mM isoproterenol.

FIG. 9A-9C shows genetically mixed micro-tissues. Wild type induced pluripotent stem cells were derived from a healthy volunteer and differentiated into either wild type cardiomyocytes (iPS-CM) or fibroblasts (EB-fibroblasts), where neither the iPS-CM nor the fibroblast express the mCherry marker. The isogenic, wild type iPS-CM or MYBPC3$^{+/-}$ and MYBPC3$^{-/-}$ iPS-CM were combined with the EB-fibroblasts to form mixed tissues. FIG. 9A shows micro-tissues made from a mixture of wild type iPS-CM and EB-fibroblasts that do not express the mCherry marker. FIG. 9B shows micro-tissues generated from a mixture of heterozygous MYBPC3$^{+/-}$ iPS-CMs that do express the mCherry marker, and wild type fibroblasts that do not express mCherry. FIG. 9C shows micro-tissues generated from a mixture of null MYBPC3$^{-/-}$ iPS-CMs that express the mCherry marker, and wild type fibroblasts that do not express mCherry. As demonstrated, the cardiomyocytes (lighter areas, red in the original) aggregated within the center of micro-tissues and that were formed.

FIG. 10A-10C show that micro-muscles can be mounted onto apparatus typically used for adult rodent muscle and macro-scale hESC-CM Engineered Heart Muscles, and that the micro-muscles exhibit behavior similar to such muscles (i.e., the micro-muscles stay intact upon being stretched and increase their passive tension when stretched). FIG. 10A is a schematic diagram of a micro-muscle on a strain gauge micromanipulator. FIG. 10B illustrates the relative muscle tensile force of cardiac micro-muscles as a function of time. To generate the micro-muscles for FIG. 10B, approximately 3000 cardiomyocytes were seeded into the stencil microwell as a mixture of 50% iPS-cardiomyocytes and 50% EB-fibroblasts, and the cells were incubated for three weeks to form the micro heart tissue (µHT; also called a micro-muscle). FIG. 10C1-10C3 shows comparative data from Tulloch et al., to illustrate the contraction force of a macroscale heart muscle generated from approximately two million cardiomyocytes differentiated from human embryonic stem cells (hESC-CM) that were incubated for three weeks to generate an engineered heart muscle (EHM) that contained about 53% hESC-CM. See Tulloch et al., Circ Res. 109(1):47-59 (2011). FIGS. 10C2 and 10C3 show expanded views of the portions of the graph shown in FIG. 10C1.

FIG. 11A graphically illustrates twitch force (in µN) as a function of percent maximum stretch. FIG. 11B illustrates the pacing frequency of micro-muscles versus their twitch amplitude. FIG. 11C graphically illustrates twitch force (in µN) as a function of percent stretch over baseline, demonstrating that the Frank-Starling behavior of micro-muscles is consistent across healthy muscles (triangular symbols), and that visibly damaged tissues do not exhibit Frank-Starling behavior (circular and square symbols). These results indicate that micro-muscles display physiologically relevant disease symptoms when damaged. FIG. 11D-11F illustrate calcium dose responses of micro-heart muscles demonstrating that the increases in twitch force (during beating) observed for micro-heart muscles are similar to macro-scale engineered heart muscle (made from more than $5 \times 10^5$ cells/tissue) formed from human embryonic stem cell derived cardiomyocytes. These data show micro-muscles behave comparably to much larger engineered heart tissues, and also that the tissues respond appropriately to inotropic stimuli. FIG. 11D graphically illustrates the force (mN) as a function of time for heart micro-muscles at 6 mM calcium. FIG. 11E graphically illustrates the force (mN) as a function of time for heart micro-muscles at 2 mM calcium. FIG. 11F graphically illustrates the force (mN) as a function of calcium concentration for heart micro-muscles.

FIG. 12A shows an image of a stencil, illustrating the surface of the PDMS material employed in the stencil, as well as the micro-wells, each with a knob and a canal. FIG. 12B graphically illustrates the amount and the scatter of mean mCherry fluorescence from mCherry-expressing micro-muscles where the cells that generated the micro-muscles were loaded by either a droplet (only) or by scraping the surface of the stencil to load the cells into microwells. Also shown in FIG. 12B are the processes to which the loaded cells were subjected including no PDMS processing, centrifugation-based wetting of the PDMS stencil, or 5 minutes of oxygen plasma treatment. High throughput loading can employ the droplet loading method, whereas scraping of cells into wells is a manual loading method. FIG. 12C graphically illustrates the surface covered by cells upon drop loading different volumes of cells where the number of cells loaded was constant. As illustrated, decreased water contact angle achieved by making the stencil surface more hydrophilic allows loading of cells into micro-wells by pipetting only, which is a method that is compatible with robotic automation. Current methods involve loading by scraping the cells into wells.

DETAILED DESCRIPTION

Figure 1A:
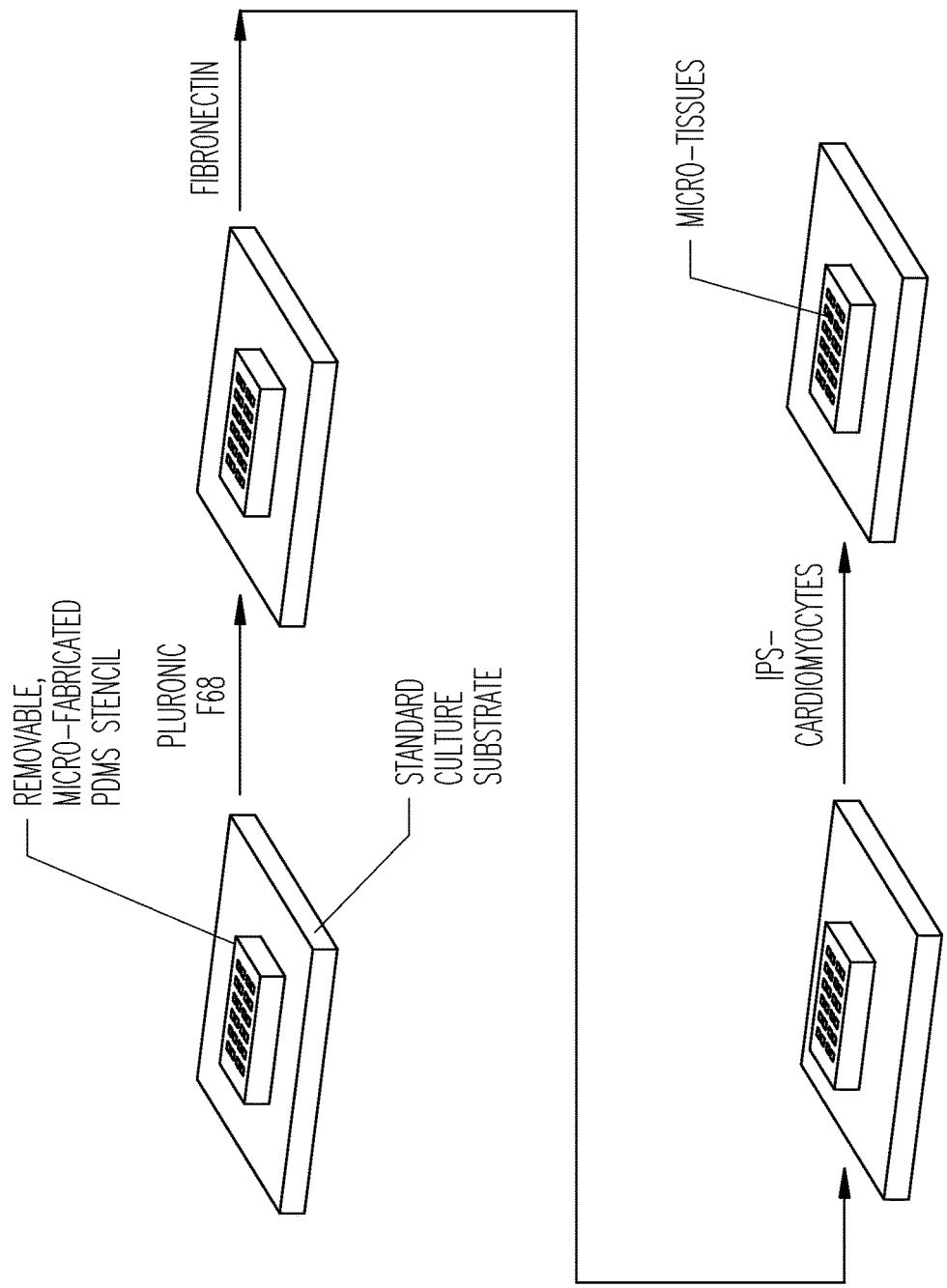

The present invention provides devices, methods and compositions for in vitro generation of three-dimensional tissues that are accurate models of heart, skeletal muscle, neuronal, and other tissues. Such models are useful for tests involving pharmacological efficacy, safety and toxicity studies. The models can include mixtures of cells that would commonly be present in an organ or tissue of interest. The cells are cultured within a stencil that not only forces alignment of the cells but guides the cells to self-assemble into three-dimensional cellular structures. Surprisingly, such accurate organ and tissue models can be manufactured without adding exogenous matrix or biomaterials.

Devices

The devices provided herein are useful for forcing cells to become aligned and to self-assemble into three-dimensional tissues. The devices generally include a cell adhesion substrate and a stencil overlay. The stencil adheres to the substrate but can be removed if desired. Cells preferentially adhere to the substrate instead of the stencil. In general, the stencil is removable, but if desired, the stencil can be covalently bonded to the substrate.

The stencils have one or more cut-out patterned microwells. The microwells are dogbone shaped, with two or more circular, oval, rectangular, square, V-shaped, or triangular holes, and each hole is joined to at least one adjacent hole by a canal. The geometry of the microwells facilitates cell alignment and self-assembly into micro-tissues by being deep enough to hold sufficient cells, by having sufficient substrate surface area in the holes to anchor the micro-tissues within the holes, and by having canals that are narrow enough (e.g., relative to the substrate surface area of the holes) to force cellular alignment and three dimensional self-assembly. The devices uniaxially align cells in the canal region, and form a tissue with a local gradient of mechanical stress, as the cells are guided by geometrical cues from a stencil.

Although each of the microwells is small enough to be seeded with only about 1000-10000 cells, the tissues that self-assemble within the microwells accurately and realistically model the properties of in vivo tissues. For example, cardiac micro-tissues formed using the devices and methods described herein express biomarkers of mature cardiac tissues, exhibit highly synchronous contractility, and respond to drugs in the same manner as heart tissues (e.g., with synchronous chronotropic and/or inotropic responses).

The low volume of the microwells and the small sizes of the micro-tissues are advantageous because the types of cells needed for evaluation can quickly be obtained (no need to grow up large numbers of cells), and a multitude of micro-tissues can simultaneously be generated and tested at once. Thus, the devices allow high throughput testing with statistically significant numbers of tissues. Abundant control micro-tissues can also be generated and tested as desired.

One issue with tissue engineering devices, especially engineered heart tissue, has been a requirement for expertise in handling extracellular matrix (ECM) gels (e.g. fibrin, collagen I) and encapsulating cells within such matrices. This process is time and temperature sensitive, and the liquid pre-hydrogel polymers tend to be viscous. All of these factors make automated pipetting, or incorporation into microfluidic devices, very difficult. Hence, significant skill is required to assemble such tissues because experts are needed to incorporate the cells into such ECM gels. Making large numbers of separate tissues is time consuming, expensive, and energy consuming.

Figure 7E:
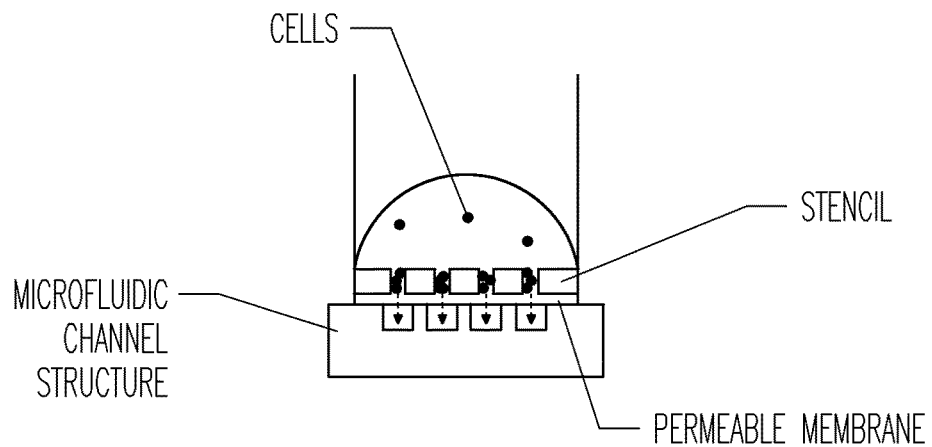
Figure 7F:
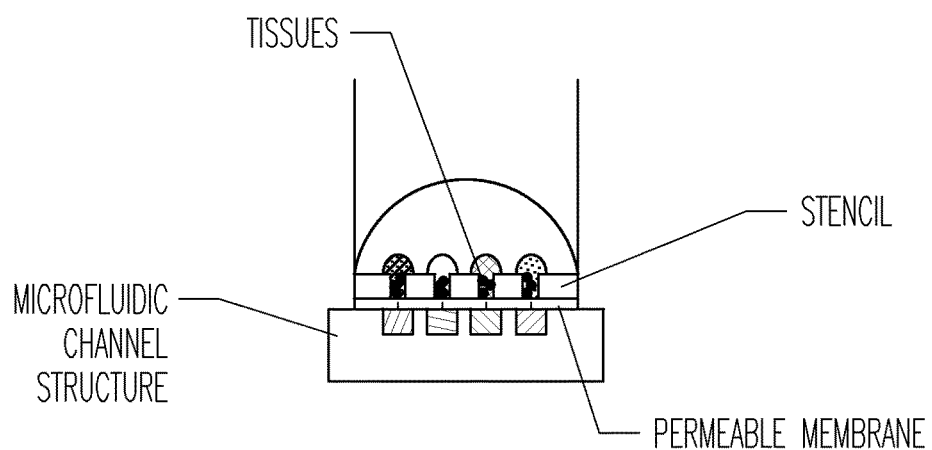

Because the devices described herein require very few cells, and no encapsulation into extra cellular matrix (ECM) gels, novel methods of cell seeding—which require smaller cell numbers than available tissue models—can be employed. One such method is called membrane loading. Briefly, instead of being attached to a tissue culture plastic substrate, the stencils are bonded to a cell adhesive, porous membrane (for example, commercially available Millipore membranes for cell extravasation studies). The pores in the membrane are smaller than cells (typically, 0.5-8 µm diameter but large enough to allow fluid flux. Media containing cells is suspended over the device. A pressure drop can be created in a variety of ways such as by applying a vacuum beneath the membranes, by centrifugation of the device, or by capillary action created by applying sterile wipes to the bottom of the membrane across the membrane to guide cells to concentrate into the micro-wells. As illustrated in FIG. 7, such gentle forces (gravity, centrifugation, or gentle suction) effectively load the wells. This approach has the advantage of being user-independent, as expertise in handling small volumes of concentrated cells would not be required.

Alignment of cells and contractile strain within the tissues occurs because of the geometric constraints of the device. When seeding cells into the device one would generally expect that the cells within the microwells would initially exert the same amount of traction force per cell, and exert stress in a random direction. However, when all the force vectors are added together for the traction exerted by all cells due to the device geometry, the magnitude of the net force along the longitudinal axis of the canal is much greater than the net force along the transverse axis.

The devices have stencil microwells that are about 200 µm to about 1000 µm, or about 250 µm to about 750 µm, or about 250 µm to about 500 µm deep. When the microwells are less than about 200 µm or less than about 250 µm deep, "bridging" of tissues across stencil microwells can occur as the cells flow or grow out of the microwells. Hence, to generate a series of separate distinct micro-tissues, the microwell depth is at least about 200 µm or at least about 250 µm. The separate micro-tissues so generated can be independently tested under different (or the same) conditions.

The canals of the microwells facilitate alignment and three dimensional self-assembly of cells cultured therein. In general, the dimensions of the canals relate to the dimensions of the adjoining holes, and to some extent to the types of cells that will undergo self-assembly. The width of the canals is less than the width of the holes. As used herein, the width of the canals and the holes is perpendicular to the longitudinal axis of the microwell.

The larger size of the holes facilitates anchoring of the micro-tissues so that during contraction of the tissues along the longitudinal axis of the microwell, the tissues do not become detached. When the holes are too small, or the width of the canals is too great, the cells do not appropriately populate, adhere to the substrate, align, and self-assemble within the entire microwell.

For example, the width of the canals is typically about 1:3 to about 1:10, or about 1:3 to about 1:7, or about 1:3 to about 1:5, or at least about 1:4 of the width of the holes. The canals can, for example, be about 10 µm to about 250 µm wide, or about 20 µm to about 225 µm wide, or about 30 µm to about 200 µm wide, or about 40 µm to about 175 µm wide, or about 50 µm to about 150 µm wide, or about 60 µm to about 135 µm wide, or about 70 µm to about 130 µm wide, or about 75 µm to about 125 µm wide, or about 100 µm wide. The length of the canals can vary from about 100 µm to about 2000 µm, or from about 200 µm to about 1500 µm, or from about 300 µm to about 1000 µm, or from about 400 µm to about 700 µm.

The holes can be about as long as they are wide. However, some variation from a 1:1 ratio of hole width to length is acceptable, and in some cases such variation is desirable. For example, the length compared to the width of the holes can be about 1:1.5, or about 1:1.25, or about 1:1, or about 1.15:1, or about 1.25:1, where the length is measured along the longitudinal axis of the microwell, and the width is measured perpendicular to the microwell.

The holes of the microwells can have a substrate surface area of about 50 $\mu m^2$ to about 500,000 $\mu m^2$, or of about 100 $\mu m^2$ to about 250,000 $\mu m^2$. The volume of the holes can vary. For example, the volume of the holes can be about 0.05 µL to about 2 µL, or about 0.1 µL to about 1.0 µL, or about 0.1 µL to about 0.5 µL.

In addition, holes with corners are typically more desirable than those with rounded sides. Hence, holes that are square, rectangular, triangular, Y-shaped, T-shaped or angular, are generally preferred over circular or oval shaped holes.

For example, the devices can have stencil micro-wells with a dogbone geometry, where the holes, also called "knobs," at the end of the dogbones can be squares with side length "L" between 250 and 1000 µm, and the canal (shaft) connecting them can have a width "y" of 50-200 µm and a length "x" of 250-1000 µm. The height of the devices can be constant within the shaft and knobs, for example, at about 100-500 µm. The ratio between L and y relates to whether or not tissues will collapse into the center of the device, and generally, for iPS-CM tissues, an L/y ratio is optimally at least five.

The stencils can be placed on, and be removable from, a substrate. The substrate can be any convenient surface to which cells can gather. For example, the substrate can be the surface of a culture plate so that cells can readily be cultured within the microwells of the stencil. Alternatively the substrate can be a membrane that not only allows transportation of the stencil-membrane unit from one location to another, but also facilitates loading of cells into microwells because gentle suction can be applied to the exterior side of the membrane so that the cells flow into the microwells when such suction is applied. Useful types of substrates and membranes are described hereinbelow.

The substrate can have a cell adhesion coating to facilitate cellular adhesion to the substrate. Such a cell adhesion coating can include adhesion proteins such as fibronectin, E-selectin, gelatin, laminin, or matrigel. The cell adhesion coating can also include hydrogel-forming polymers such as collagen, fibrinogen, bisacrylamide, or combinations thereof. In addition, the cell adhesion coating can include RGD peptides, PHSRN peptides, and DGEA peptides, and combinations thereof.

The stencil can be coated with a blocking agent to inhibit cell adhesion to the stencil. Such a coating facilitates removal of the stencil without removal of the micro-tissue from the substrate. In addition, coated with a blocking agent diminishes cell adhesion to the top of the stencil, for example between microwells, so that each micro-tissue is separate from the others. The blocking coating can be a polymeric coating, a protein coating, or a detergent. Examples of suitable stencil coatings include Pluronics, polyethylene oxide, alginate, poly-N-isopropylacrylamide, bovine serum albumin, or combinations thereof. The stencil coatings can also include hydrogels such as bisacrylamide, alginate, agarose, polyethylene glycol diacrylate, or any combination thereof. Coatings may be applied by physioabsorption or covalent binding Stencil Manufacture The stencil can be made from a variety of materials. The microwells are indentations or holes within the stencil that are backed by a substrate.

For example, the stencils can include materials such as polydimethylsiloxane (PDMS), surface functionalized PDMS, polyimide, polyurethane, SU8, thermoplastics, poly(methylmethacrylate) (PMMA), polycarbonate (PC), polystyrene (PS), polyethylene terephthalate (PET), polycaprolactone (PCL), poly(vinyl chloride) (PVC), fibrin, glass, quartz, silicon, hydrogel forming polymers (e.g. polyacrylamide, polyethylene glycol, alginate, agarose), protein-based gels (e.g., gelatin, collagen, and/or fibrin) or any combination thereof. In some instances, the stencil is made from an elastomeric material such as a flexible polymeric material. Poly(dimethylsiloxane) (PDMS) is one example of an elastomeric material that readily be manufactured into the stencils described herein.

The stencils can be manufactured by any available procedure. In one example, poly(dimethylsiloxane) (PDMS; sylgard 184, Dow-Corning) stencils, each with a plurality of microwells, can be fabricated by replica molding on an SU8 master mold. Such a master mold can be patterned by standard photolithography procedures.

The shape of the microwells in the stencil can be generated by AutoCAD® 2005 and printed with a high-resolution plot (Innovative Laser System, Singapore). An SU-8 wafer can serve as a master patterning template for the stencils. Clean silicon wafers can be used as the surface upon with the SU-8 master wafer is generated. The silicon wafers are dried after cleaning and a thick coating of SU-8 100 can be applied by spin coating followed by soft-baking to form a first layer of SU-8 of about 250 µm. To form thicker (500 µm) SU-8 masters, a second cycle of SU-8 100 spin-coating and soft-baking can be applied to the first coat.

After soft-baking, wafers are cooled to room temperature and a transparency mask can be applied. The SU-8 coating is exposed to ultraviolet light, baked, and then exposed to SU-8 developer for 2-20 hours. The coated wafers are baked at 175° C. for more than 2 hours to produce a master for the stencils. The master can be coated to prevent adhesion of the stencil polymers to the SU-8/silicon surface of the master in subsequent processing steps. For example, the master can be contacted or exposed to vapors of Tridecafluoro-1,1,2,2-Tetrahydrooctyl-1-Trichlorosilane.

Multi-level fabrication of the master template is not required to manufacture stencils containing a variety of different polymers that can be used to form the stencils. Alternative procedures can be used for manufacturing, such as laser engraving (Myers et al. *Integr. Biol.* 5: 1495-506 (2013)).

Substrate

The substrate of the devices forms the base on which the stencil is placed. Microwells are formed by the walls of the stencil and a substrate floor. The substrate can be a solid support surface or a porous membrane.

The substrate can include a polymeric material such as: polyolefins, polystyrenes, "tissue culture treated" polystyrenes, poly(alkyl)methacrylates and poly(alkyl)acrylates, poly(acrylamide), poly(carbonate), poly(ethylene glycol), poly(N-isopropyl acrylamide), polyacrylonitriles, poly(vinylacetates), poly(vinyl alcohols), chlorine-containing polymers (such as poly(vinyl)chloride), polyoxymethylenes, polycarbonates, polyamides, polyimides, polyurethanes, polyvinylidene difluoride (PVDF), phenolics, amino-epoxy resins, polyesters, polyethers, polyethylene terephthalates (PET), polyglycolic acids (PGA), poly-(p-phenyleneterephthalamides), polyphosphazenes, polypropylenes, silicon, as well as copolymers and combinations thereof. The substrate can also be a porous membrane made from available polymers of advanced silicon (Striemer et al. *Nature* 445: 749-53 (2007).

Substrates that are clear can be useful for viewing, visually evaluating, and/or monitoring the micro-tissues from below (e.g., with the naked eye or with a microscope). For example, the substrate can be glass. Clear substrates also allow illumination of the micro-tissues from below.

For example, the solid support can include polystyrene.

In some embodiments, the solid support comprises "tissue culture treated" polystyrene, e.g., polystyrene that has been treated with oxygen plasma to generate oxygen species in the polystyrene. See, e.g., Ramsey et al. *In Vitro* 20:802 (1984); Beaulieu et al. *Langmuir* 25:7169 (2009); and Kohen et al. *Biointerphases* 4:69 (2009).

Similarly, PDMS materials can also be treated with oxygen plasma.

A synthetic substrate can include peptides, proteins, or Matrigel™. However, matrix proteins are not needed for cell alignment and self-assembly. Instead, the substrate need only be non-toxic and sufficiently adhesive for cells to adhere thereto.

A substrate can be provided in any of a variety of forms. For example, the substrate can be a tissue culture dish (e.g., a 5-cm culture dish, a 10-cm culture dish); a multi-well cell culture plate (e.g., a 6-well cell culture plate; a 96-well cell culture plate etc.); and the like.

The stencil can be covalently bonded to the underlying substrate. The covalent bonds can be formed so that the stencil is permanently attached to the substrate. Alternatively, the covalent bonds between the stencil and the substrate can be reversed, disrupted or cleaved so that the stencil can be removed and retrieved from the substrate. For example, stencil and substrate can be covalently modified with aminosilane to present surface amine groups, and substrate and stencil can be cross-linked together with sodium alginate (molecular weight between 6 and 250 kDa) using carbodiimide chemistry. For stencil retrieval, alginate can be degraded enzymatically using alginate lyase.

The substrate can also include a porous membrane onto which the stencil is placed. The membrane can be fabricated from any of the materials used to form the substrates. However, the membrane should have pores that are smaller than cells, but large enough to allow significant flux of fluids and particles smaller than cells (e.g. pores should be from 0.5-10 μm in diameter). This includes commercially available membranes such as the Millipore Transwell™. Membranes can also be formed by introducing pores into elastomers such as PDMS. To further enhance the functionality of the devices, it is also possible that the "underside" of the membrane (the side which faces away from the loaded cells) can be modified with a microfluidic network. In this manner, adjacent micro-tissues can be subjected to different compounds of interest, including small molecules, oligonucleotides and proteins. Thus, the substrate can be a porous membrane that prevents cellular flux but allows fluid flow.

The substrate can include a network of microfluidic channels beneath a membrane, where the microfluidic channels are on the side opposite to where the cells are loaded. Such a network of microfluidic channels can be used to selectively deliver test compounds, proteins or oligonucleotides to cells in specific microwells of the stencils, or to apply a gradient of test compounds, proteins or oligonucleotides across the microwells.

When the substrate is a membrane, cell loading can be accomplished by applying a dilute cell suspension, and then applying a differential of force across the membrane using capillary action, or vacuum applied specifically through microfluidic channels. Cell loading can also be accomplished by allowing gravity to settle the cells within the microwells when the substrate is a solid surface or when the substrate includes a membrane.

Cells

Cells that can be cultured within microwells of the stencil devices include partially and fully differentiated cells. Stem cells can also be cultured in the microwells of the stencil devices, however, in general, partially and fully differentiated cells are desired for generation of micro-tissues that are accurate models of in vivo organs and tissues systems. Examples of cells that can be cultured to generate three dimensional tissues include, but are not limited to, adipocytes, cardiomyocytes, fibroblasts, endodermal cells, epithelial cells, keratinocytes, myocytes, neurons, osteoblasts, pancreatic islet cells, retinal cells, stromal cells, and the like.

The cells that are cultured depend in part on the tissue type, or nature of the disorder or condition, to be tested. In general, at least some of the cells to be cultured naturally align, elongate, and/or contract in vivo.

At least some of the cells can be genetically modified to express the GCaMP6f gene product, which is a green fluorescent calcium indicator protein that emits green fluorescence in response to action potentials. The GCaMP6f gene product is so sensitive that it can be used to detect single action potentials, for example, in neuronal somata, orientation-tuned synaptic calcium transients, and when the cardiac and skeletal muscle micro-tissues contract. Plasmids encoding the GCaMP6f gene product are available from addgene.org (see website at www.addgene.org/40755/).

The cells can also be modified to express fluorescent markers such as green fluorescent protein or mCherry. The cells can also be modified to express other types of fluorescent proteins such as any of the red, orange and yellow fluorescent proteins derived from *Discosoma* sp. (see, e.g., Shaner et al., *Nature Biotechnology* 22, 1567-1572 (2004)), the contents of which are specifically incorporated herein by reference in their entirety). mCherry is a monomeric fluorescent protein with peak absorption/emission at 587 nm and 610 nm, respectively. The mCherry protein is resistant to photo-bleaching and is stable. It matures quickly, with a $t_{0.5}$ of 15 minutes, allowing it to be visualized soon after translation The cells selected for culture in the stencil devices can be all of one cell type or be a mixture of cell types. For example, to optimally mimic an organ system, a mixture of the types of cells that found in the organ system can be employed. For example, in many cases heart disease is not caused by defects or injuries in cardiomyocytes themselves, but in fibroblasts, endothelial cells, neurons, or other cells that support the structure and function of the organ. The stencil micro-tissues can be formed with defined mixtures cells, and mixing experiments can be performed where certain cell types are genetically labeled (e.g. to track calcium flux or sarcomere structure), or where certain cell types have a defect that is associated with a disease or conditions via various mechanisms.

For example, if a three-dimensional micro-tissue model of heart is desired, a mixture of cardiomyocytes, myoblasts, epithelial cells, endothelial cells, neuronal cells, fibroblasts, multipotent cardiomyocyte progenitors, or any combinations thereof can be employed. In another example, if a three-dimensional model of skeletal muscle is desired, a mixture of muscle tissue cells such as skeletal muscle stem cells, myoblasts, myosatellite cells, epithelial cells, myoepithelial cells, fibroblasts, connective cells, myoblasts, multipotent muscle progenitors, or any combinations thereof can be employed. In a further example, if a three-dimensional model of neuronal tissues is desired, a mixture of neurons, neuronal progenitor cells, glial cells, actrocytes, basket cells, beta cells, medium spiny neuron cells, pukinje cells, renshaw cells, unipolar brush cells, granular cells, anterior horn cells, spindle cells, and combinations thereof can be employed.

Such cell types can be obtained from a variety of sources. For example, the cells can be obtained from public cell depositories (e.g., the American Type Culture Collection, ATCC), from patients, from biopsies, via differentiation or conversion of other cell types, and any combination thereof. In some cases, the cells are obtained by differentiation from stem cells, or by conversion of one cell type for another.

To mimic various organ systems, the cells can be differentiated from stem cells of various genetic backgrounds, for example, by inducing formation of stem cells from somatic cells of patients with particular diseases or conditions.

Cells seeded within microwells can include at least some progenitor cells that mature as they grow, align, and self-assemble within the microwells.

For example, the stem cells can be induced pluripotent stem cells (iPSCs) or stem cells obtained from any convenient source. The stem cells can be at least partially differentiated or converted into the lineage of a desired organ or tissue type.

Examples of stem cells that can be employed include hematopoietic stem cells, embryonic stem cells, mesenchymal stem cells, neural stem cells, epidermal stem cells, endothelial stem cells, gastrointestinal stem cells, liver stem cells, cord blood stem cells, amniotic fluid stem cells, skeletal muscle stem cells, smooth muscle stem cells (e.g., cardiac smooth muscle stem cells), pancreatic stem cells, olfactory stem cells, hematopoietic stem cells, and the like.

Suitable human embryonic stem (ES) cells include, but are not limited to, any of a variety of available human ES lines, such as BGO1(hESBGN-O1), BGO2 (hESBGN-02), BG03 (hESBGN-03) (BresaGen, Inc.; Athens, Ga.); SA01 (Sahlgrenska 1), SA02 (Sahlgrenska 2) (Cellartis AB; Goeteborg, Sweden); ES01 (HES-1), ES01 (HES-2), ES03 (HES-3), ES04 (HES-4), ES05 (HES-5), ES06 (HES-6) (ES Cell International; Singapore); UCO1 (HSF1), UC06 (HSF-6) (University of California, San Francisco; San Francisco, Calif.); WAO1 (HI), WA07 (H7), WA09 (H9), WA09/Oct4D10 (H9-hOct4-pGZ), WA13 (H13), WA14 (H14) (Wisconsin Alumni Research Foundation; WARF; Madison, Wis.). Cell line designations are given as the National Institutes of Health (NIH) code, followed in parentheses by the provider code. See, e.g., U.S. Pat. No. 6,875,607.

Suitable human ES cell lines can be positive for one, two, three, four, five, six, or all seven of the following markers: stage-specific embryonic antigen-3 (SSEA-3); SSEA-4; TRA 1-60; TRA 1-81; Oct-4; GCTM-2; and alkaline phosphatase.

Hematopoietic stem cells (HSCs) are mesoderm-derived cells that can be isolated from bone marrow, blood, cord blood, fetal liver and yolk sac. HSCs are characterized as $CD34^+$ and CD3. HSCs can repopulate the erythroid, neutrophil-macrophage, megakaryocyte and lymphoid hematopoietic cell lineages in vivo. HSCs can be in vitro induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

Mesenchymal stem cells (MSC), originally derived from the embryonal mesoderm and isolated from adult bone marrow, can differentiate to form muscle, bone, cartilage, fat, marrow stroma, and tendon. Methods of isolating MSC are available in the art; and any available method can be used to obtain MSC. See, e.g., U.S. Pat. No. 5,736,396, which describes isolation of human MSC.

Induced pluripotent stem (iPS) cells are pluripotent stem cell induced from a somatic cell, e.g., a differentiated somatic cell. iPS cells are capable of self-renewal and differentiation into cell fate-committed stem cells, including neural stem cells, as well as various types of mature cells. iPS cells can be generated from somatic cells, including skin fibroblasts, using available methods. iPS cells produce and express on their cell surface one or more of the following cell surface antigens: SSEA-3, SSEA-4, TRA-1-60, TRA-1-81, TRA-2-49/6E, and Nanog. In some embodiments, iPS cells produce and express on their cell surface SSEA-3, SSEA-4, TRA-1-60, TRA-1-81, TRA-2-49/6E, and Nanog. iPS cells express one or more of the following genes: Oct-3/4, Sox2, Nanog, GDF3, REX1, FGF4, ESG1, DPPA2, DPPA4, and hTERT. In some embodiments, an iPS cell expresses Oct-3/4, Sox2, Nanog, GDF3, REX1, FGF4, ESG1, DPPA2, DPPA4, and hTERT. Methods of generating iPS are known in the art, and any such method can be used to generate iPS. See, e.g., Takahashi and Yamanaka (2006) *Cell* 126:663-676; Yamanaka et. al. (2007) *Nature* 448:313-7; Wernig et. al. (2007) *Nature* 448:318-24; Maherali (2007) *Cell Stem Cell* 1:55-70; Nakagawa et al. (2008) *Nat. Biotechnol.* 26: 101; Takahashi et al. (2007) *Cell* 131:861; Takahashi et al. (2007) *Nat. Protoc.* 2:3081; and Okita et al. (2007) *Nature* 448:313.

iPS cells can be generated from somatic cells (e.g., skin fibroblasts) by collecting such somatic cells from a desired source (e.g., a patient). Hence, the cells can be an allogeneic or allogeneic mammalian cell population from a patient that has a disease or condition of interest. The collected cells can be induced to become pluripotent stem cells or to convert the collected cells into a different cell type.

The collected cells can be induced to express one or more pluripotency factors such as Oct-3/4, Sox2, c-myc, Klf4 a short hairpin RNA (shRNA) against p53, or a combination thereof.

Expression of endogenous or recombinantly introduced pluripotency factors can be induced by available procedures. For example, pluripotent expression vectors can be transfected into a collected cell population, and expression of the pluripotency factors encoded by those expression vectors can be induced. The pluripotent expression vectors can be integrated into the genomes of the cells, or the pluripotent expression vectors can be maintained episomally for the time needed to redirect the cells to the endodermal lineage. Episomal introduction and expression of pluripotency factors is desirable because the mammalian cell genome is not altered by insertion of the episomal vectors and because the episomal vectors are lost over time. Hence, use of episomal expression vectors allows expression of pluripotency factors for a sufficient time to convert nonpluripotent mammalian cells to pluripotent stem cells or to progenitor cells of a desired lines, while avoiding possible chromosomal mutation.

Episomal plasmid vectors encoding p53 suppression factors and/or other pluripotency factors can be introduced into mammalian cells as described for example, in Yu et al., "Human induced pluripotent stem cells free of vector and transgene sequences," *Science* 324(5928): 797-801 (2009); United States Patent Application Publication No. 20120076762, and Okita et al., "A more efficient method to generate integration-free human iPS cells," *Nature Methods* 8: 409-412 (2011), the contents of which publications are specifically incorporated herein by reference in their entireties.

For example, the pluripotency factors can be encoded within and expressed from an episomal vector that has EBNA-1 (Epstein-Barr nuclear antigen-1) and oriP, or Large T and SV40ori sequences so that the vectors can be episomally present and replicated without incorporation into a chromosome.

Cells from various lineages can be induced to a stem cell-like phenotype by procedures described by United States Patent Application Nos. 20130059385, 20120190059, 20110110899, 20100267141, 20100233804 and WO/2011/123572, the contents of which are specifically incorporated herein by reference in their entireties.

The pluripotency factors can be introduced into mammalian cells in the form of DNA, protein or mature mRNA by a technique such as lipofection, binding with a cell membrane-permeable peptide, liposomal transfer/fusion, or microinjection. When in the form of DNA, a vector such as a virus, a plasmid, or an artificial chromosome can be employed. Examples of viral vectors include retrovirus vectors, lentivirus vectors (e.g., according to Takahashi, K. and Yamanaka, S., *Cell,* 126: 663-676 (2006); Takahashi, K. et al., *Cell,* 131: 861-872 (2007); Yu, J. et al., *Science,* 318: 1917-1920 (2007)), adenovirus vectors (e.g., Okita K, et al., *Science* 322: 949 (2008)), adeno-associated virus vectors, and Sendai virus vectors (*Proc Jpn Acad Ser B Phys Biol Sci.* 85: 348-62, 2009), the contents of each of which references are incorporated herein by reference in their entireties. Also, examples of artificial chromosome vectors that can be used include human artificial chromosome (HAC), yeast artificial chromosome (YAC), and bacterial artificial chromosome (BAC and PAC) vectors. As a plasmid, a plasmid for mammalian cells can be used (e.g., Okita K, et al., *Science* 322: 949 (2008)).

A vector encoding a pluripotency factor can contain regulatory sequences such as a promoter, an enhancer, a ribosome binding sequence, a terminator, and a polyadenylation site, operably linked so that a pluripotency factor can be expressed. A vector may further contain, if desired, a selection marker sequence such as a drug resistant gene (e.g., a neomycin resistant gene, an ampicillin resistant gene, and a puromycin resistant gene), a thymidine kinase gene, and a diphtheria toxin gene, a reporter gene sequence such as a green fluorescent protein (GFP), β-glucuronidase (GUS), FLAG, or combinations thereof. Also, the above vector may have LoxP sequences located before and after the segment encoding the pluripotency factor to permit cleavage at the ends of the pluripotency factor segment (before and after) or at both ends of the segment encoding a promoter and the pluripotency factor after introduction into the mammalian cells.

The nucleic acid segment encoding a pluripotency factor can be operably linked to a promoter. The promoter is typically selected from promoters which are functional in mammalian cells, although prokaryotic promoters and promoters functional in other eukaryotic cells may be used. The promoter can be derived from promoter sequences of viral or eukaryotic genes. For example, it may be a promoter derived from the genome of a cell in which expression is to occur. However, a heterologous promoter is often desirable. Examples of eukaryotic promoters that can be employed include those promoters that function in a ubiquitous manner (such as promoters of a-actin, b-actin, or tubulin) or, alternatively, a tissue-specific manner (such as promoters of the genes for pyruvate kinase).

Tissue-specific promoters can be specific for lymphocytes, dendritic cells, skin, brain cells and epithelial cells. Examples of promoters include CD2, CD11c, keratin 14, Wnt-1 and Rhodopsin promoters. An epithelial cell promoter such as SPC can be used. Viral promoters may also be used, for example the Moloney murine leukemia virus long terminal repeat (MMLV LTR) promoter, the rous sarcoma virus (RSV) LTR promoter or the human cytomegalovirus (CMV) IE promoter. The promoters employed for expression of pluripotency factors can be inducible promoters that respond to specific stimuli. An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent such as a protein, metabolite, growth regulator, phenolic compound, steroid, or a physiological stress imposed directly by, for example heat, or indirectly through the action of a pathogen or disease agent such as a virus. It may be advantageous for the promoters to be inducible so that the levels of expression of the heterologous gene can be regulated during the life-time of the cell. In addition, any of these promoters may be modified by the addition of further regulatory sequences, for example enhancer sequences. Chimeric promoters may also be used comprising sequence elements from two or more different promoters described above.

In some embodiments, the cells to be cultured in the microwells are genetically modified to replace, modify, or add a gene of interest. For example, such genetic modification can be used to generate micro-tissues that realistically model in vivo diseased organs or tissues with conditions of interest.

The collected cells can include mutant cells and/or genetically modified cells with a variety of modified genes. Examples of genes in which mutations can affect cardiac function include any of the following: ABCC9, ACTC1, ACTN2, ANK1, ANKRD1, AKAP9, ANK2, BAG3, CACNA1C, CACNB2, CASQ2, CAV3, COX15, CRYAB, CSRP3, CTF1, DES, DMD, DNAJC19, DSC2, DSG2, DSP, DTNA, EYA4, FHL2, FKTN, FOXD4, GIRK4, GLA, hERG, KCNE1, KCNE2, KCNH2, KCNJ2, KCNJ5, KCNJ8, KCNQ1, KCNQ2, LAMA4, LAMP2, LDB3, LMNA, MiRP1, MYBPC3, MYH6, MYH7, MYL2, MYL3, MYOZ2, NEXN, PKP2, PLN, PRKAG2, PSEN1, PSEN2, RBM20, RYR2, SCN4B, SCN5A, SDHA, SGCD, SNTA1, SYNE1, SYNE2, TAZ, TCAP, TMEM43, TMPO, TNNC1, TNNT2, TNNC1, TNNI3, TPM1, TRDN, TTN, TTR, VCL, or any combination thereof. See, e.g., McNally et al., *J. Clin. Invest.* 123(1): 19-26 (2013), and George, *J. Clin. Invest.* 123(1): 75-84 (2013), the contents of which references are specifically incorporated herein by reference in their entirety.

Examples of genes in which mutations can affect skeletal muscle function include any of the following: ACTA1, BAG3, DMD, EMD, FHL1, LMNA, MTM1, MYBPC3, MYH2, MYH7, NEB, RYR1, SYNE1, SYNE2, TNNT1, TPM2, TPM3, TTN, or any combination thereof. See table, published annually in the Journal of Neuromuscular Disorders, the contents of the select set of the listed genes are incorporated by reference herein (see website at www.musclegenetable.fr).

Examples of genes in which mutations can give rise to neuronal conditions include CACNA1C, KCNQ1, KCNH2, KCNJ2, CACNB2, CACNA2D1, SCN5A, SMN1, HSPB1, HSPB3, AARS, GARS, or any combination thereof.

In some embodiments the cells to be cultured in the stencils are human cells. Alternatively, the cells to be cultured in the stencils are animal cells, such as from domestic animals, zoo animals, laboratory animals, or wild animals.

Methods

The devices described herein are useful for generating micro-tissues that realistically model in vivo organ and/or tissue systems. Methods of making such micro-tissues involve seeding selected mammalian cells into one or more microwells of a device described herein, and culturing the seeded cells within the microwells to thereby induce alignment and self-assembly of the mammalian cells into one or more micro-tissues.

The mammalian cells can be seeded in at least two adjacent holes of a microwell, wherein the two holes are joined by a canal. Mammalian cells can be seeded in multiwells to permit generation of multiple micro-tissues useful, for example, for statistically relevant studies for testing micro-tissue models of selected organ or tissue types.

The microwells are typically seeded with fewer cells than are currently employed for toxicity, therapeutic agent identification, and drug testing. For example, some researchers have generated tissues from about 250,000 to about 1 million cells. However, the micro-tissues described herein can be generated from about 2000 to about 9,500 cells, or about 3000 to about 9000 cells, or about 4000 to about 8500 cells, or about 5000 to about 8000 cells per microwell.

The seeded cells are cultured for about 2 hours to about 14 days, or for about 1 day to about 10 days, or for about 2 days to 7 days, or for about 2 days to about 6 days, or for about 2 days to 5 days.

Culture media that can be employed include DMEM™, DMEM/F12, or Knock-Out (KO) DMEM available from Gibco (supplied e.g. by Gibco Invitrogen, Sigma, BD, Lonza) that contain low concentration of human or animal serum, or no serum, and bFGF, VEGF, ascorbic acid, heparin, and/or hydrocortisone as supplements. Another type of medium that can be mTESR-1 human pluripotent stem cell culture medium (STEMCELL Technologies), StemPro34 (Invitrogen), or EGM-2 BulletKit™ (Lonza). Non-limiting examples of optional factors than may be further included are insulin, IGF-I, hEGF, transferrin and/or hormones such as triiodothyronine.

For example, human ESCs and iPSCs can be cultured on Matrigel (BD Biosciences) coated plates with mTESR-1 human pluripotent stem cell culture medium (STEMCELL Technologies) to 80% confluence. Such cells can be dissociated with Accutase (Sigma) to small clumps containing 10-20 cells and resuspended in 2 ml basic media (StemPro34, Invitrogen, containing 2 mM glutamine, Invitrogen, 0.4 mM monothioglycerol, Sigma, 50 µg/ml ascorbic acid, Sigma, and 0.5 ng/ml BMP4, R&D Systems) to form embryoid bodies (EBs). Other factors such as BMP4 (10 ng/ml), human bFGF (5 ng/ml), and Activin A (3 ng/ml) can be added a day or a few days later to the basic media for cardiac specification. The media for embryoid bodies so formed can be replaced or refreshed with basic media containing human DKK1 (50 ng/ml) and human VEGF (10 ng/ml), followed by basic media containing human bFGF (5 ng/ml) and human VEGF (10 ng/ml) a few days thereafter.

When the desired level of differentiation is obtained, the cells can be seeded into the microwells of the devices described herein. The cells in the microwells grow, self-assemble, and form three-dimensional tissues. For example, cells in adjacent holes grow and align along the canal joining the adjacent holes. The micro-tissues formed in the wells exhibit contractility with greater synchronicity than two-dimensional monolayers of the same cell type and composition.

The micro-tissues formed in the microwells of the devices described herein respond to drugs with greater synchronicity, for example, than two-dimensional monolayers of the same cell type and composition. For example, the micro-tissues formed in such microwells exhibit chronotropic and/or inotropic responses to drugs that are more synchronized compared to than two-dimensional monolayers of the same cell type and composition. Note, an inotropic drug response is a marker of mature cardiomyocytes (Yang et al. Circ Res 114(3): 511-23 (2014)). Micro-tissues formed in the microwells exhibit an inotropic response to isoproterenol but a monolayer of the mammalian cells forming such micro-tissues does not.

In general, the micro-tissues formed using the devices and methods described herein exhibit a mature phenotype that is characteristic of in vivo organ and tissue systems.

The micro-tissues can be evaluated to ascertain or confirm the functional and structural properties of the micro-tissues. For example, after culturing the seeded cells within the microwells, the cells and/or tissues within the microwells can be evaluated to determine whether cells are aligned in the canals of one or more of the microwells, to determine whether cells have formed three-dimensional structures in one or more canals or holes of the microwells, or a combination thereof. The cells and/or micro-tissues can also be evaluated to determine whether cells are contracting along the longitudinal axis of one or more of the microwells. The methods described herein can also include determining micro-tissue morphology, genetic expression, contraction rate, contraction intensity, electrical activity, calcium transient amplitude, intracellular $Ca^{2+}$ level, cell size, contractile force production, sarcomeric a-actinin distribution, or a combination thereof.

As illustrated herein, the micro-tissues formed in the microwells exhibit contractility with greater synchronicity than two-dimensional monolayers of the same cell type and composition. The micro-tissues formed in the microwells also respond to drugs with greater synchronicity than two-dimensional monolayers of the same cell type and composition. For example, as illustrated herein the micro-tissues formed in the microwells exhibit chronotropic and/or inotropic responses to drugs that are more synchronized compared to than two-dimensional monolayers of the same cell type and composition. The micro-tissues formed in the microwells also exhibit an inotropic response to isoproterenol but a monolayer of the animal cells does not.

The micro-tissues formed by the methods described herein are stable. For example, the stencil used to generate the micro-tissues can be removed to provide intact micro-tissues that adhere to the substrate. Removal of the stencil can facilitate certain types of analyses, such as recovery of cells from the micro-tissues and determination of expression patterns and levels of one or more mRNAs or proteins.

The micro-tissues can be subjected to a variety of analytical procedures with or without removal of the stencil from the micro-tissues. For example, the following types of analyses can be performed with or without removal of the stencil from the micro-tissues: fixing one or more microtissues, fixing one or more micro-tissues, freezing one or more micro-tissues, sectioning one or more micro-tissues, staining one or more micro-tissues, or a combination thereof.

For example, multiple micro-tissues either within the stencil, or after removal of the stencil, can be submerged into a hydrogel-forming mixture that crosslinks to form a gel that will support and hold the micro-tissues for easy manipulation during processes such as fixing, cryosectioning, embedding in paraffin, sectioning, staining, in situ hybridization, histochemical evaluation, and combinations thereof.

The micro-tissues can immersed or inverted into hydrogels such as agarose, alginate, fibrin, gelatin-methacrylate, polyethylene oxide diacrylate, polyAMPS, polyvinylpyrrolidone, methylcellulose, hyaluronan, polyvinyl alcohol, sodium polyacrylate, acrylate, or any combination thereof.
Patient-Specific, Isogenic Disease, and/or Genetically Engineered Micro-Tissues Because the micro-tissues described herein require fewer cells than the current engineered heart tissues, the stencil-based micro-tissues are amenable to the study of many different cell lines. In contrast, devices that require large numbers of progenitor cells typically limit researchers to using induced pluripotent stem cells or human embryonic stem cell derived progenitor cells from cell lines that differentiate into the progenitor cells with a high yield. By requiring fewer input cells, the devices presented here increase flexibility, and even cell lines that do not give high yields can be used. Hence, patient-specific cell lines, or genome edited cell lines in which patient-specific mutations are corrected, or "wild type" iPS from healthy volunteers that are modified to harbor disease-associated mutations can be employed.

Additionally, the use of fewer cells enables the use of various reporter cell lines. For example, tissues made with iPS-cardiomyocytes that harbor the GCaMP6f calcium indicator allow continuous recording of calcium flux (see, e.g., FIG. 8). The GCaMP6f gene product is a green fluorescent calcium indicator that emits green fluorescence in response to action potentials. The GCaMP6f gene product is so sensitive that it can be used to detect single action potentials, for example, in neuronal somata, orientation-tuned synaptic calcium transients, and when the cardiac and skeletal muscle micro-tissues contract.

Plasmids encoding the GCaMP6f gene product are available from addgene.org (see website at www.addgene.org/40755/).
Cardiac Disease/Condition Models The micro-tissues described herein can be used to identify new and existing drugs useful for treatment of various cardiac diseases and conditions. For example, micro-tissues can be generated from cells exhibiting mutations correlated with the development of various cardiac conditions and/or diseases. The micro-tissues can also be incubated under conditions that will give rise to a cardiac condition or disease. After formation of a cardiac micro-tissue model test compounds can be incubated with the model micro-tissues and the micro-tissues can be evaluated to ascertain whether any of the test compounds have therapeutic value.

Hence, a method is described herein for identifying a compound for treatment of a cardiac disease or condition that involves generating at least one micro-tissue model of the cardiac disease or condition, contacting the micro-tissue model with a test compound, and determining with the test compound alleviates at least one symptom of the cardiac disease or condition. A series of micro-tissue models can simultaneously be tested, for example, by generating micro-tissue models in multiple wells of microtiter dish, or in multiple wells of a culture dish. Each dish can contain a series of control micro-tissues (e.g., healthy micro-tissues, tissue biopsy samples exhibiting symptoms of the disease or condition, two-dimensional monolayers of the cells used to generate the micro-tissue model, or any combination thereof).

Dilated cardiomyopathy (DCM) is one of the cardiomyopathies, a group of diseases that primarily affect the myocardium. In DCM a portion of the myocardium is dilated, often without any obvious cause. Left or right ventricular systolic pump function of the heart is impaired, leading to progressive cardiac enlargement and hypertrophy, a process called remodeling. Although in many cases no etiology is apparent, dilated cardiomyopathy can result from a variety of toxic, metabolic, or infectious agents. About 25-35% of patients have familial forms of the disease, with most mutations affecting genes encoding cytoskeletal proteins, while some affect other proteins involved in contraction. The disease is genetically heterogeneous, but the most common form of its transmission is an autosomal dominant pattern. Cytoskeletal proteins involved in DCM include cardiac troponin T (TNNT2), α-cardiac actin, desmin, and the nuclear laminin A and C, and various other contractile proteins.

Where the disease is DCM, the micro-tissues can be stimulated with positive inotropic stress, such as a β-adrenergic agonist before, during or after contacting model micro-tissues with the test agent(s). In some embodiments the β-adrenergic agonist is norepinephrine, isoproterenol, or a combination thereof. The types of test agents that can be contacted with DCM micro-tissue models can also include genetic agents in the pathways that promote cardiogenesis, integrin and cytoskeletal signaling, and ubiquitination pathway. Compared to control, healthy micro-tissues, DCM micro-tissue models can exhibit decreased calcium transient amplitude, decreased contractility, and abnormal sarcomeric a-actinin distribution. The model tissues so generated can be evaluated to ascertain what effects therapeutic drugs may have, and/or the effects of unknown compounds on such model micro-tissues can be determined.

Hypertrophic cardiomyopathy (HCM), is a condition in which sarcomeres replicate causing heart muscle cells to increase in size, which results in the thickening of the heart muscle. In addition, the normal alignment of muscle cells is disrupted, a phenomenon known as myocardial disarray. HCM also causes disruptions of the electrical functions of the heart. HCM is most commonly due to a mutation in one of 9 sarcomeric genes that results in a mutated protein in the sarcomere. Myosin heavy chain mutations are associated with development of familial hypertrophic cardiomyopathy. Hypertrophic cardiomyopathy is usually inherited as an autosomal dominant trait, which mutations reported in cardiac troponin T (TNNT2); myosin heavy chain (MYH7); tropomyosin 1 (TPM1); myosin binding protein C (MYBPC3); 5'-AMP-activated protein kinase subunit gamma-2 (PRKAG2); troponin I type 3 (TNNI3); titin (TTN); myosin, light chain 2 (MYL2); actin, alpha cardiac muscle 1 (ACTC1); and cardiac LIM protein (CSRP3). An insertion/deletion polymorphism in the gene encoding for angiotensin converting enzyme (ACE) alters the clinical phenotype of the disease. The D/D (deletion/deletion) genotype of ACE is associated with more marked hypertrophy of the left ventricle and may be associated with higher risk of adverse outcomes.

As shown herein, both short-term (30 minutes) and chronic (5 days of daily dosing) exposure to the β-adrenergic agonist isoproterenol, MYBPC3$^{-/-}$ micro-tissues exhibited a blunted decrease in beat-rate (e.g. a decreased chronotropic response). Such an effect can further be exacerbated with drugs that accelerate the disease. Such a condition can lead to chronic reduced beating rates, compromised contraction, and significantly more cells with abnormal sarcomeric α-actinin distribution.

Where the micro-tissue disease model is HCM, the micro-tissue model can also be stimulated with positive inotropic stress, such as a β-adrenergic agonist before, during or after contacting with the test agent. Under such conditions, HCM micro-tissue models can display higher hypertrophic responses, which can be reversed by a β-adrenergic blocker. Compared to healthy micro-tissues, HCM micro-tissue model can exhibit increased cell size and up-regulation of HCM related genes, and more irregularity in contractions characterized by immature beats, including a higher frequency of abnormal Ca2+ transients, characterized by secondary immature transients. These micro-tissue models can have increased intracellular $Ca^{2+}$ levels. Appropriate text compounds for such an HCM micro-tissue model can include agents that target calcineurin or other targets associated with calcium affinity.

Anthracycline-induced cardiotoxicity (and resistance to anthracycline-induced toxicity) is a condition generated by administration of anthracyclines. Anthracyclines such as doxorubicin are frontline chemotherapeutic agents that are used to treat leukemias, Hodgkin's lymphoma, and solid tumors of the breast, bladder, stomach, lung, ovaries, thyroid, and muscle, among other organs. The primary side effect of anthracyclines is cardiotoxicity, which results in severe heart failure for many of the recipients receiving regimens utilizing this chemotherapeutic agent.

To identify therapeutic agents with utility against anthracycline-induced cardiotoxicity, cardiac micro-tissues can be generated and exposed to an anthracycline such as doxorubicin until symptoms of anthracycline-induced cardiotoxicity are evident. The micro-tissue model so generated can then be contacted with test agents. Test can be performed to ascertain with any of the test agents alleviate or reduce the symptoms of anthracycline-induced cardiotoxicity. Anthracyclines have differential toxicity in different patients, and it is likely that certain genetic conditions predispose individuals to the cardiotoxic effects of these drugs (Gianni et al., *J Clinc. Oncol.* 26(22): 3777-84 (2008)). Accordingly, micro-tissues may be used to screen for mutations that lead to toxicity with these drugs, to determine whether a specific genetic mutation would put an individual at higher risk for cardiotoxicity upon receiving said drug.

Arrhythmogenic right ventricular dysplasia (ARVD) is an autosomal dominant disease of cardiac desmosomes that results in arrhythmia of the right ventricle and sudden cardiac death. It is second only to hypertrophic cardiomyopathy as a leading cause for sudden cardiac death in the young.

To generate micro-tissue models of ARVD, patient specific iPSC-cardiomyocytes (iPSC-CMs) can be obtained from patients carrying a hereditary mutation for ARVD. Family matched samples can be used to generate micro-tissue controls. These ARVD micro-tissue models and control micro-tissues can be used for drug screening and to identify molecular targets for such therapy.

Left Ventricular Non-Compaction (LVNC, aka non-compaction cardiomyopathy) is a hereditary cardiac disease which results from impaired development of the myocardium (heart muscle) during embryogenesis. Patients with mutations causing LVNC develop heart failure and abnormal cardiac electrophysiology early in life.

To generate micro-tissue models of LVNC, patient specific iPSC-cardiomyocytes (iPSC-CMs) can be obtained from patients carrying a hereditary mutation for LVNC. Family matched samples can be used to generate micro-tissue controls. These LVNC micro-tissue models and control micro-tissues can be used for drug screening and to identify molecular targets for therapy.

Double Inlet Left Ventricle (DILV) defects are congenital heart defects in which both the left and right atria feed into the left ventricle. As a result, children born with this defect only have one functional ventricular chamber, and trouble pumping oxygenated blood into the general circulation.

To generate micro-tissue models of DILV, patient specific iPSC-cardiomyocytes (iPSC-CMs) can be obtained from patients carrying a hereditary mutation for DILV. Family matched samples can be used to generate micro-tissue controls. These DILV micro-tissue models and control micro-tissues can be used for drug screening and to identify molecular targets for therapy.

Long QT (Type-1) Syndrome (LQT-1, KCNQ1 mutation) is a hereditary arrhythmic disease in which the QT phase of the electrocardiogram is prolonged, resulting in increased susceptibility for arrhythmia and sudden cardiac death. There are 13 known genes associated with LQT.

To generate micro-tissue models of LQT, patient specific iPSC-cardiomyocytes (iPSC-CMs) can be obtained from patients carrying a hereditary mutation for LQT. Family matched samples can be used to generate micro-tissue controls. These LQT micro-tissue models and control micro-tissues can be used for drug screening and to identify molecular targets for therapy.

For example, to determine which drugs can be effective against a patient's cardiac condition or disease, cells can be obtained from the patient, one or more cardiac micro-tissues can be generated from the patient's cells, a test compound (e.g., a drug) can be incubated with the one or more micro-tissues so generated, and the effects of the test compound upon the one or more micro-tissues can be evaluated to thereby determine which test compounds (e.g. drugs) can be effective against a patient's cardiac condition or disease.

Muscular and Neuronal Micro-Tissue Models

The micro-tissues described herein can be used to identify new and existing drugs useful for treatment of various muscular and/or neuronal diseases and conditions. For example, micro-tissues can be generated from cells exhibiting mutations correlated with the development of various muscular or neuronal conditions and/or diseases. The micro-tissues can also be incubated under conditions that will give rise to a muscular or neuronal condition or disease. After formation of the desired micro-tissue model test compounds can be incubated with the model micro-tissues and the micro-tissues can be evaluated to ascertain whether any of the test compounds have therapeutic value, for example, to relieve symptoms of the disease or condition.

Hence, a method is described herein for identifying a compound for treatment of a muscular tissue disease or condition that involves generating at least one micro-tissue model of the muscular disease or condition, contacting the micro-tissue model with a test compound, and determining with the test compound alleviates at least one symptom of the muscular disease or condition.

Similarly, another method is described herein for identifying a compound for treatment of a neuronal tissue disease or condition that involves generating at least one micro-tissue model of the neuronal disease or condition, contacting the micro-tissue model with a test compound, and determining with the test compound alleviates at least one symptom of the neuronal disease or condition.

A series of micro-tissue models can simultaneously be tested, for example, by generating micro-tissue models in multiple wells of microtiter dish, or in multiple wells of a culture dish. Each dish can contain a series of control micro-tissues (e.g., healthy micro-tissues, tissue biopsy samples exhibiting symptoms of the disease or condition, two-dimensional monolayers of the cells used to generate the micro-tissue model, or any combination thereof).

Examples of muscular and/or neuronal diseases and/or conditions that the micro-tissues can model include muscular dystrophies, neuropathies, myasthenia gravis, Creutzfeldt-Jakob disease, cerebrovascular accident (stroke), Parkinson's disease, multiple sclerosis, Huntington's disease (Huntington's chorea), Lambert-Eaton syndrome, inflammatory myopathies, polymyositis, primary muscular (myopathic) disorders, polymyalgia rheumatic, dermatomyositis, inclusion body myositis, rhabdomyolysis, or combinations thereof. Other types of diseases and/or conditions that the micro-tissues can model include spinal-muscular atrophies (disorders of lower motor neurons), amyotrophic lateral sclerosis (a mixed upper and lower motor neuron condition).

Other conditions and/or diseases that the micro-tissues can model include neuropathies, which involve dysfunction of the peripheral nerves including motor neurons. The motor neurons carry the electrical signals directly from the spinal cord and brain stem to activate muscle movement. Neuropathies also include conditions and diseases of the sensory neurons, which convey sensory information such as pain, temperature, light touch, vibration and position to the brain. Conditions or diseases of the autonomic neurons, which go to the internal organs and control blood vessel reflexes, can also be modeled by the micro-tissue models prepared using the devices and methods described herein.

In general, cells with mutations that can give rise to any such conditions or diseases can be seeded into the devices described herein, and cultured to generate micro-tissues for testing. Such cells can be reprogrammed to generate stem cells or progenitor cells having the desired mutation and the desired stage of differentiation prior to seeding in the microwells.

Test Compounds

Any test compounds of interest can be incubated with the micro-tissues described herein. For example, libraries of compounds as well as newly synthesized compounds can be screened to ascertain their safety and/or efficacy in the micro-tissue models described herein. Both control and disease model micro-tissues can be contacted with, and/or incubated in the presence of test compounds.

Examples of drugs or test compounds that can be tested for efficacy or toxicity in any of the micro-tissue models include any of the following from LC Laboratories: bortezomib, bexarotene, clofarabine, docetaxel, decitabine, doxorubicin, ixabepilone, K252a, nilotinib hydrochloride monohydrate, okadaic acid, taxol134, sorafenib, sunitinib, U0126, vincristine, or any combination thereof. Other examples of drugs or test compounds that can be tested for efficacy or toxicity in any of the micro-tissue models include any of the following from Sigma Aldrich include any of the following: monosodium glutamate/L-glutamic acid monosodium salt hydrate, adrenaline, bromobenzene, cinchophen, cadmium chloride, bisphenol A, arsenic, lead chloride, dioxane, $Na_2CrO_4$, bioallethrin, amprolium, chlorpromazine, carbon tetrachloride, carbaryl, ochratoxin A, cypermethrin, paraquat, benzene, $HgCl_2$, chlorpyrifos, diazinon, HCBD, hexachlorobutadiene, ethylenethiourea, lindane, maneb, permethrin, rotenone135, ziram, dexamethasone, trichloroethylene, pyrimethamine, roxarsone, albuterol, cisplatin, tetracycline, alpidem, aristolochic acid, aprotinin, acetaminophen, amitriptyline, antimycin135, BMAA (b-N-methylamino-L-alanine), busulfan, propulsid, isoflurane, GBR 12909, epinephrine, epirubicin hydrochloride, fenfluramine, fipexide, flecainide, fluorouracil, gentamicin, glafenine, hydroxyurea, imipenem, isoniazid, isoproterenol, kainite, L-741,626, lamotrigine, letrozole, capsaicin, NMDA, metoprolol, mitoxantrone hydrochloride, deltamethrin, nomifensine, nefazodone, pemoline, L-phenylalanine, propylthiouracil/6-Propyl-2-thiouracil, valproic acid, phenylbutazone, probenecid, pergolide, procainamide, carbamazepine, accutane, isotretinoin, lovastatin, atorvastatin, trovafloxacin, sitaxsentan, rosigliatazone, retinoic acid, trans-retinoic acid, D-serine, sibutramine, cerivastatin, tolcapone, bromfenac, alosetron, pentostatin, thalidomide, troglitazone, tobramycin, thiotepa, vinorelbine tartrate, verapamil, or any combination thereof.

Other test compounds can also be evaluated for efficacy and/or lack of toxicity by incubating any the micro-tissues described herein with such test compounds.

Kits

The invention also relates to one or more kits for generating and/or testing any of the micro-tissues described herein. The kits can include any of the devices described herein, or components for making any of the devices described herein, as well as instructions for making and/or using the devices. The kits can also include cells for generating micro-tissues.

For example, the kits can include one or more devices that include a cell adhesion substrate; and an elastomeric stencil overlay, as well as instructions for making and/or using the devices; wherein the elastomeric stencil has one or more cut-out patterned microwells comprising two or more circular, oval, rectangular, square, V-shaped, or triangular holes, each hole joined to an adjacent hole by a canal; and wherein the cell adhesion substrate binds cells within at least the holes of the cut-out pattern. The kit can also include any of the other features and components of the devices described herein. The instructions for making and/or using the devices can include instructions for preparing device for generating micro-tissues, for seeding the microwells of the device, for culturing the device(s) that contain cells to make micro-tissues, for analyzing the physiological activities of the micro-tissues, for analyzing the gene expression of the micro-tissues, for removing the stencil if desired, for preparation an use of an appropriate gel or tissue embedding agent for analysis of the micro-tissues, for immersing or inverting the micro-tissues into a gel or embedding medium, and combinations thereof.

The kits can also include a master patterning template, a substrate, an elastomeric material and instructions for assembling a device from such components. The instructions for making and/or using the devices can include instructions for preparing the substrate for the stencil overlay, for coating the substrate with one or more cell adhesion agents, for making the (e.g. elastomeric) material that will form the stencil, for generating microwells in the (e.g. elastomeric) material, for curing the (e.g. elastomeric) material of the stencils, for coating the stencils with a blocking agent, for using the devices to make micro-tissues, for testing and evaluating micro-tissues in the devices, or any combination thereof.

The kit can also include one or more containers that have cells for generating micro-tissues. Cells for model test micro-tissues can be included in one or more containers. Control cells for making control micro-tissues can be provided in one or more separate containers. The cells can be pure cultures of certain cell types, or mixtures of cells, for example, as described herein. The cells included in the various containers can be those for generating disease micro-tissue models, and/or control micro-tissues. The instructions for making and/or using the devices can include directions for mixing appropriate cell types to generate healthy and/or mutant or diseased micro-tissues of various organ or tissue types. The instructions can also include instructions on how to test various disease model micro-tissues in the presence and absence of test compounds.

Definitions

As used herein and in the appended claims, the singular forms "a," "an," and "the" include plural reference unless the context clearly dictates otherwise. Thus, for example, a reference to "a device," "a micro-tissue," "a compound," "a cell," "a nucleic acid" or "a polypeptide" includes a plurality of such devices, tissues, compounds, cells, nucleic acids or polypeptides (for example, a series of devices or tissues, a solution of cells, nucleic acids or polypeptides, a suspension of cells, or a series of compound, cell, nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The following non-limiting examples illustrate some aspects of the invention.

EXAMPLE 1

Materials and Methods

This Example illustrates some of the materials and methods that can be employed to make and use the invention.

SU-8 Master Wafer Fabrication

Lithography protocols were used to create an SU-8 wafer that served as a patterning template (Bian 2009). Briefly, silicon wafers were clean-etched in pirhana (3:1 mixture of sulfuric acid to hydrogen peroxide) at 80° C. for 15 minutes in a chemical fume hood. Next, wafers were cleaned twice in 1 L of double-distilled $H_2O$ and allowed to air dry. Clean wafers were then heated to 225° C. for 10 minutes for full dehydration, then cooled to room temperature, and a 250 µm thick coating of SU-8 100 was applied by spin coating (ramp-up to 500 rpm, hold for 10 seconds, then ramp up to 1000 rpm and hold for 30 seconds), and soft-baking (65° C. for 15 minutes, then ramp up to 95° C. and hold for 2 hr). To form thicker (500 µm) SU-8 masters, a second cycle of SU-8 100 spin-coating and soft-baking was applied, and the time of the 95° C. step was increased to 16 hr. Wafers were protected from ambient light during all processing steps.

After soft-baking, wafers were cooled to room temperature. A transparency mask (company) was applied and the SU-8 was exposed to UV light at 12 mW/cm$^2$ for 3×60 second cycles (250 µm) or 6×60 second cycles (500 µm) with 60 seconds of off-time between exposures to prevent wafer heating. After UV exposure, wafers were post-exposure baked at 45° C. for 24 hr, and then exposed to SU-8 developer for 2-20 hours and subsequently hard baked at 175° C. for more than 2 hr. Finally, freshly prepared wafers were exposed to vapors of Tridecafluoro-1,1,2,2-Tetrahydrooctyl-1-Trichlorosilane for 24 hr in a vacuum bell chamber to prevent adhesion of polymers to the SU-8/silicon surface in subsequent processing steps. Finally, freshly prepared wafers were exposed to vapors of trichlorosilane for 24 hr in a vacuum bell chamber to prevent adhesion of polymers to the SU-8/silicon surface in subsequent processing steps.

Elastomeric Stencil Fabrication

Poly(dimethyl siloxane) elastomer (PDMS; Sylgard 184 Kit, Dow Corning) was mixed at a 10:1 ratio of 10 parts PDMS to 1 part cross linker compound, and degassed in a vacuum bell chamber. Next, the liquid PDMS was sandwiched between the surface of the patterned SU-8, and a piece of LaserJet transparency paper backed by a glass slide. The assembled sandwich was incubated at 60° C. for 24 hr to crosslink the polymer. After PDMS crosslinking, stencils were incubated in acetone for 2 hr and then washed in isopropyl alcohol.

Preparing Stencils for Micro-Tissue Assembly

A stencil (or array of stencils) is of an appropriate size to fit inside and at the bottom of an incubation plate. Stencils should be small enough to be well centered in the plate or in the wells of the plate, and away from the walls of the wells. Any fluid that is placed atop the stencil should have no chance of touching the sides of the plate or the well, otherwise cells can seed poorly.

PDMS stencils were applied to the surface of standard tissue culture polystyrene substrates (BD Falcon). In some cases, the surface of the substrate (e.g., the wells) was wetted with a few drops of isopropyl alcohol. The stencil was laid down carefully to avoid trapping air between the stencil and the plastic surface. The plate with the stencils positioned within wells can be spun at 2500×g for 25 minutes to eliminate air bubbles.

Next, the stencil-substrate constructs were incubated at 65-75° C. for 3-12 hours (e.g., overnight) to seal the stencils to the substrate (and evaporate off the isopropyl alcohol is used), thereby forming an air-tight and reversible seal (FIG. 1A). In some cases, PDMS substrates were first disinfected with isopropyl alcohol and washed in double distilled $H_2O$, and then adsorbed onto a thin layer of Matrigel, in a sterile fume hood.

Stencil-substrate constructs were next disinfected with pure isopropyl alcohol or ethanol for 30 minutes. The stencil-substrate constructs can be spun at 2500 g for 25 minutes, to completely wet the microwells inside the stencil. The stencil-substrate constructs can be dried incubated for about 1 hour to insure disinfection. The alcohol was removed and replaced with sterile 60% isopropyl alcohol or with 70% ethanol solution (in double distilled $H_2O$). In some cases, the alcohol was removed by replacing that solution with three changes of pure double distilled $H_2O$. During each of these washes, the substrates can be degassed for 15 minutes. The alcohol can be aspirated off and air-dried. In some cases, the substrates were degassed for 15 minutes. To test whether a stencil is bound to the substrate, the stencil can be poked with a sterile pipette or tweezers; any stencil that easily moves should be discarded. Sterile water can be added the stencil-substrate constructs, and the stencil-substrate constructs can be spun at 2500×g for 25 minutes to wet the inside of the stencils. At this point, substrates were stored up to one week before performing tissue assembly studies.

To inhibit protein and cell adhesion to the PDMS stencils, the stencils were coated with Pluronics F68 (1%) for 1 hour at room temperature, without vacuum degassing or centrifuging (FIG. 1A). The Pluronics solution was removed by aspiration. This short treatment was sufficient to prevent cell adhesion to the PDMS but not sufficient to prevent cell adhesion to the tissue culture plastic. Next, substrates were washed 3 times using PBS, for 15 minutes with vacuum degassing, or by spinning the stencil-substrate constructs for 20 minutes at 2500×g. In some cases the wash solutions contained 0.1% Pluronics F68. To promote cell adhesion, the stencil-substrates were incubated overnight, at room temperature and with vacuum degassing, in 10-20 µg/mL Bovine Plasma Fibronectin (Invitrogen) or in 0.1% Bovine Plasma Fibronectin (FIG. 1A). In some cases, the fibronectin solution was added and the stencil-substrate constructs were spun for 20 minutes at 2500×g, and the constructs were incubated at room temperature overnight.

Micro-Tissue Assembly

Induced pluripotent stem cells (iPS cells) were generated or frozen iPS cells were thawed, and cardiomyocytes were generated from the iPS cells (iPS-CM). The iPS-CM can be stored as frozen cells and thawed for later use, or IPS-CM can be freshly generated from iPS cells. Typically, "immature" cardiomyocytes, obtained between 15 and 25 days after the initiation of cardiomyocyte differentiation from human pluripotent cells were used. The protocol used was similar to the one originally published by Lian et al. (*Proc. Natl. Acad. Sci. USA* 109(27): E1848-57 (2012)).

A mixture of cardiomyocytes and stromal cells (typically Thy1 positive, CD31 negative fibroblasts; Ma et al., *Biomaterials* 35(5): 1367-77 (2014)) with 50-80% cardiac troponin positive fibroblasts, and the remainder as stromal was prepared.

For fresh cardiomyocytes and stroma, cells were singularized by enzymatic digestion, and then concentrated to $10^7$ cells per mL. For frozen cardiomyocytes and stroma, twice as many cells were used to account for cell death upon thawing. Cells were resuspended into Embryoid Body 20 media (EB20; Dulbecco's Modified Eagle Media, DMEM, with high glucose containing non-essential amino acids, sodium pyruvate, 20% certified fetal bovine serum and glutamine) supplemented with 10 µM Y27632 and 150 µg/mL L-ascorbic acid.

The iPS-CM and fibroblasts were washed with PBS, and then trypsinized with 0.25% trypsin in PBS. In some cases, the cardiomyocytes were first digested with Accutase™ for 20 minutes before "spiking" the digestion solution with 1 part Accutase with 1 part 0.25% trypsin. In some cases, a "gentle" digestion was employed using 0.05% trypsin for the fibroblasts. In general, digestion with trypsin (optionally with Accutase™) is preferable to mechanical shearing to separate the cells. Incubation in the trypsin solution can be at 37° C. for 5-12 minutes, until see single cells are visible under a microscope. The trypsin digestion was quenched with EB20 (without drugs or supplements). The cells were collected by centrifugation at 300 g for 5 minutes and then resuspended into the EB20/ascorbic acid/Y27632 media. The cells were counted, collected, and resuspended at a concentration of $10^7$ cells/mL in EB20/Y27362/L-ascorbic acid media.

The water of fibronectin solution bathing the wells is carefully removed from wells by vacuum aspiration such that the tops of PDMS stencils remain wet but the sides of the stencils are dry. Next, a small volume of PBS can be added so that the wells are wet, the PBS is removed, and the cells are added to one well at a time. In some instances a small volume of cell suspension (10-50 µL) is added directly to the wells, rather than adding and removing the PBS before adding the cells. The volume of PBS or cells employed can vary, depending on the surface area of the stencils.

To force aggregation of cells for tissue formation, the wells were centrifuged at 200 g for 5 minutes. Under the microscope, the "filling" of wells and the status of the cells can be observed. Beating of the cells should be visible. If no beating is observed, feed the cells with EB20/ascorbic acid (without Y27632).

In some experiments, the aggregated cell masses can were incubated, without addition of media, for 30 minutes, at which point, excess media (typically, 2 mL per well of a 12 well plate) was added (EB20 with 10 µM Y27632 and 150 µg/mL L-ascorbic acid; FIG. 1A).

Media was exchanged at 24-48 hr. If micro-tissues were not beating, the media was exchanged daily for EB20 until beating was observed. At this point, media was exchanged for either StemPro34 (Invitrogen) or RPMI with B27 supplement (Invitrogen), in some case with insulin and/or 150 µg/mL L-ascorbic acid. Tissues were fed every other day, with ascorbic acid added during the first week.

In some optimization studies, C2C12 mouse myoblasts expressing the nuclear marker H2B-mCherry under the constitutive EFla promoter were utilized as a model contractile cell line. C2C12s were propagated in DMEM with high glucose, supplemented with glutamine, sodium pyruvate and 10% Fetal Bovine Serum.

Physiologic Analysis of Micro-Tissues

The beating rate, maximum contraction velocity, and spatial coordination of beating within micro-tissues was assessed visually, and quantified using image processing software was used, such as the custom block-matching optical flow software, described in a publication that is currently under review (Huebsch 2014). Micro-tissue response to drugs, including verapamil and isoproterenol, was tested using an automated inverted microscope (Zeiss).

Analysis of Cardiomyocyte Structure and Size within Micro-Tissues

Figure 2A:
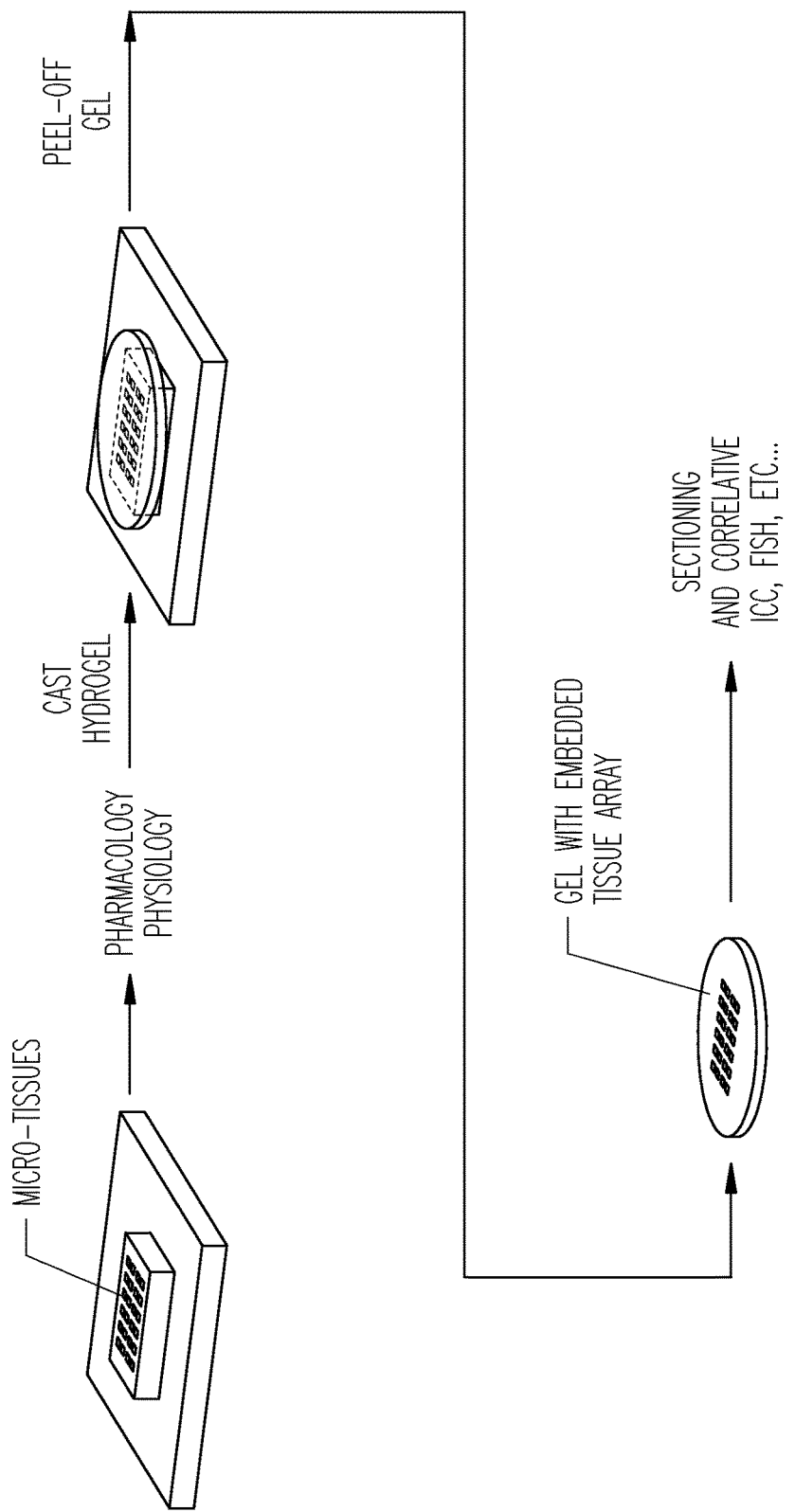
FIG. 2A-2D illustrate the cellular structure of micro-tissues and their biomarker expression as analyzed by a hydrogel inversion process.
Figure 2B:
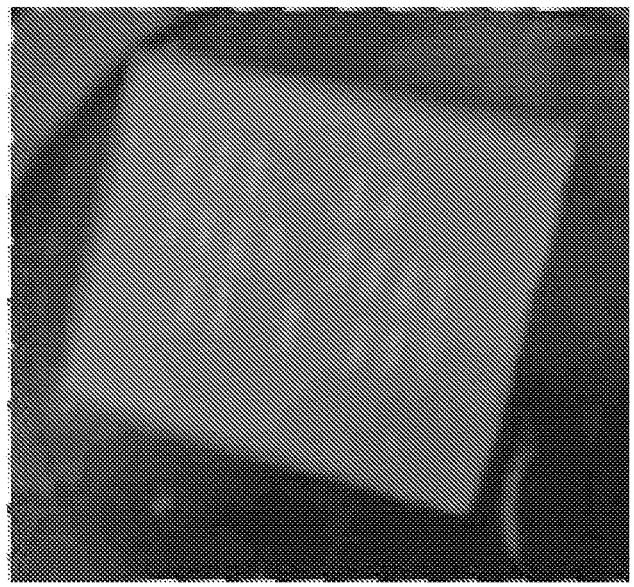
Figure 2C:
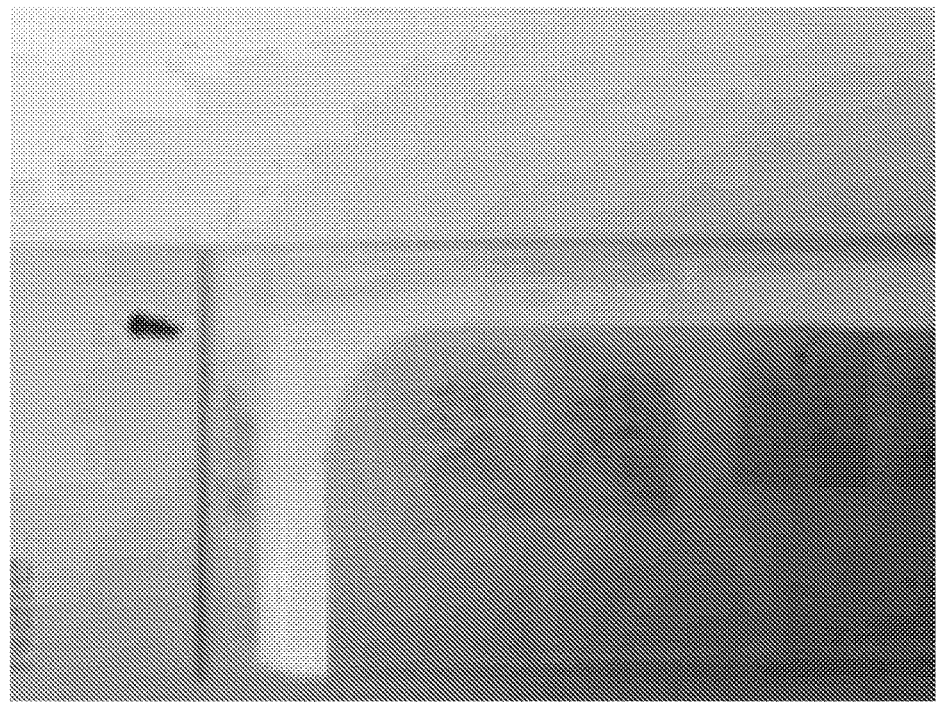
Figure 2D:
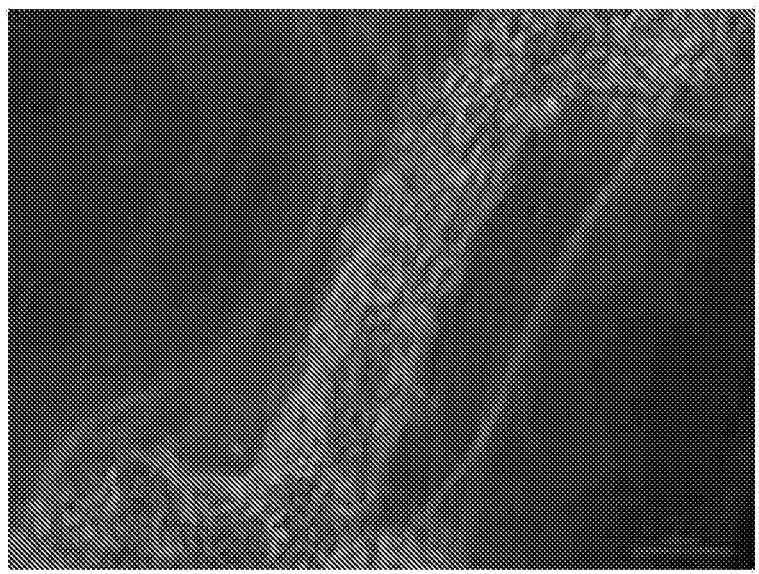

To enable robust, high-fidelity sectioning of micro-tissues, a method termed "Hydrogel Inversion" was devised. For this method, the elastomeric stencil was either removed with tweezers, or left intact. Cells are either left alive, or fixed (for example, with methanol/acetone or paraformaldehyde). A pre-hydrogel polymer or monomer mixture was next added to the micro-tissues. As the gel became cross-linked, the tissue became embedded within, so that when the gel was removed from the substrate, the micro-tissue array is taken with it (FIG. 2A-2B). In the case where the stencil is removed, relatively viscous pre-hydrogel polymers (e.g. 2% wt agarose; FIG. 2B) were sometimes used. If the stencil was not removed before hydrogel inversion, a less viscous pre-hydrogel polymer or monomer mixture was employed (e.g. calcium-alginate; FIG. 2D). This technique is similar to the InVERT technique recently published by Stevens et al. (Stevens 2013).

Hydrogel-embedded micro-tissue arrays were next sectioned with standard techniques (e.g. cryosectioning after embedding into optical cutting temperature medium, OCT, or paraffin sectioning). To assess gross morphology, standard stains (e.g. hematoxylin/eosin) were applied. To assess cell size, wheat germ agglutinin or other surface-stains (e.g. antibodies against vincullin) were used. To assess sarcomeric structure and alignment within the tissue, antibodies against sarcomeric actinin were used.

EXAMPLE 2

Micro-Tissue Assembly

Figure 1B:
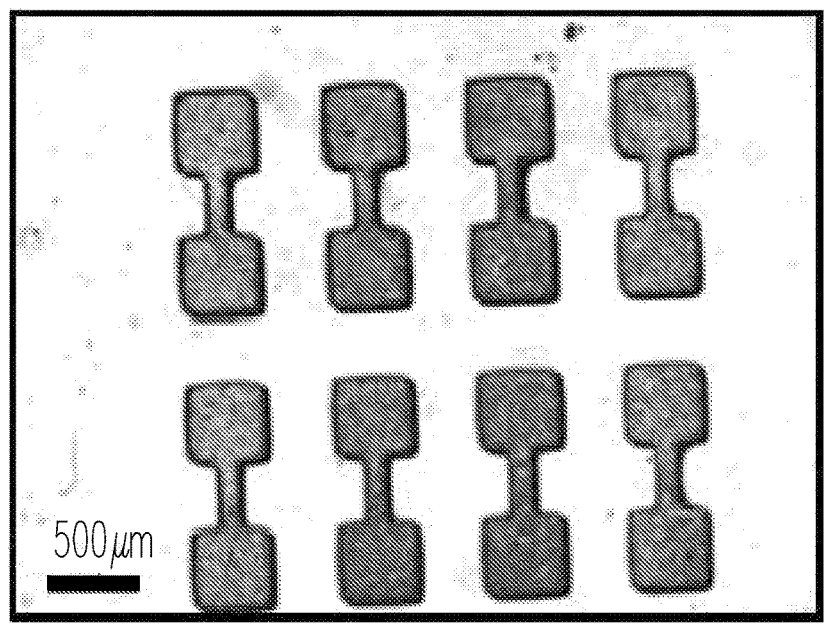
Figure 1C:
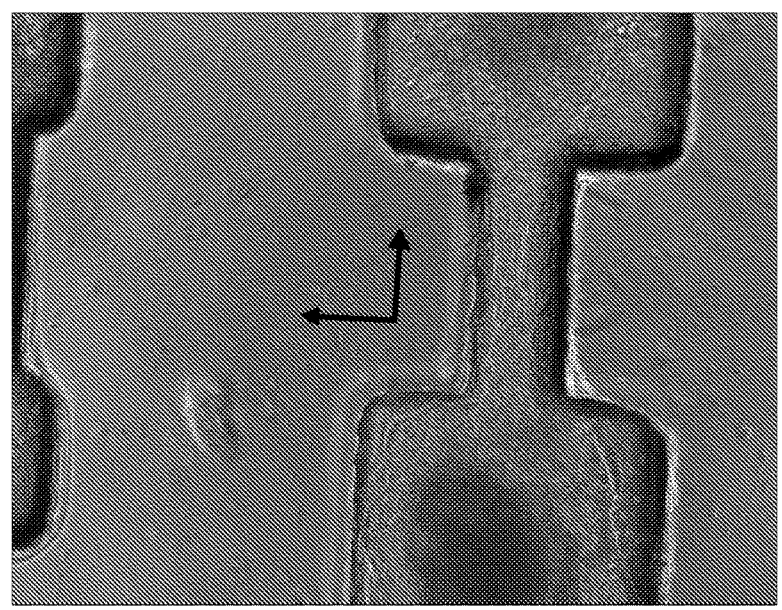

When a concentrated suspension of cells was seeded into micro-tissue stencil-substrate constructs, the cells routinely partitioned into the micro-well portion of the construct (e.g. within the holes present in the elastomeric stencils; FIG. 3A1-3A4). Analysis of induced pluripotent stem cell-cardiomyocyte (iPS-CM) contractility and tissue assembly within micro-tissues revealed that beating began to occur within 1 day of introducing fresh cells, or within 2 days of thawing frozen cells (data not shown).

When micro-tissues were formed within PDMS that was not blocked to minimize cell adhesion, distinct layers of tissue formed above the microwells (on the PDMS surface) and within microwells, and in some cases, these tissue layers separated from one another within 2 days of re-plating (FIG. 3A). The blocking agent Pluronic F68 was applied to diminish cell adhesion to the top of the stencil, between micro-wells.

This approach to forming a tissue with elastomeric stencils was compared to previously described work by Folch and coworkers (see, e.g., Folch et al., *J Biomed Mater Res* 2000; 52(2): 346-53; and Li et al., *Crit Rev Biomed Eng.* 2003; 31(5-6):423-88). Folch and coworkers typically removed elastomeric stencils within 1-2 days of seeding cells, and cells proliferated to fill the void spaces inside "micro-wells." However, for non-proliferating cells, or slowly proliferating cells, like iPS-CM, it is advisable to seed cells at tissue-level confluency.

Figure 3B:
FIGS. 3B and 3C show representative images of micro-tissues formed from cardiomyocytes differentiated from induced pluripotent stem cells (iPS-CM) within micro-wells of PDMS stencils that were passivated against protein adhesion (to provide isolated tissues) where the microwells in FIG. 3B have a rectangular geometry and the microwells in FIG. 3C have a dogbone geometry. The width of the rectangle and the canal, also called the "shaft," of the dog-bone was 100 µm in both experiments. Note that with the rectangular geometry, the mass of cells tends to collapse toward the center of the device, whereas with the dogbone geometry, the large cell masses on either end of the narrow "shaft" region are prevented from collapsing into the center of the device.
Figure 3C:
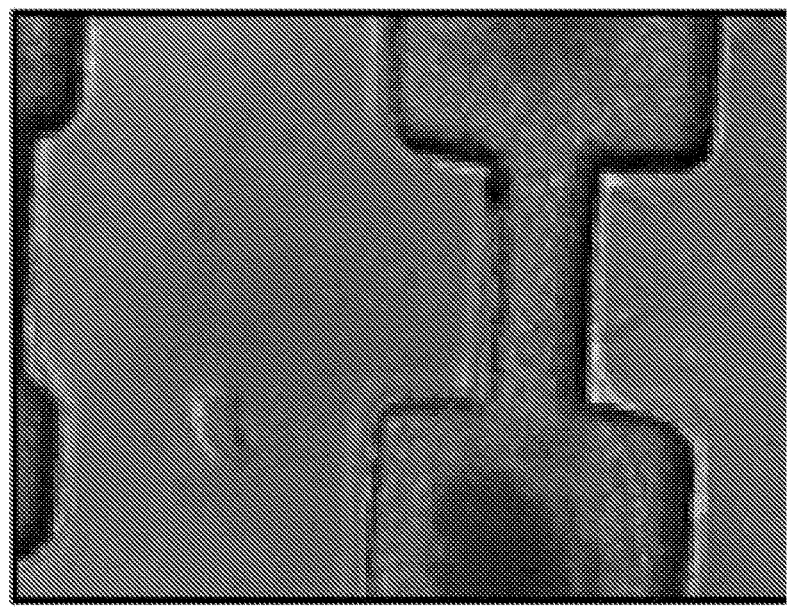

High concentrations of cell populations were used during seeding to allow formation of individual tissues (mechanically independent from one another). To prevent protein and cell adhesion when such large numbers of cells were employed. For initial studies, the PDMS surfaces of the devices were blocked with detergents (Pluronics F68). During these studies with C2C12 and iPS-CM, it was noted that controlling the aspect ratio of the through-holes within the elastomeric stencil would elicit some initial cell alignment. However, both cell types tended to contract into balls of tissue with weak contractility, especially when a simple rectangular microwell was employed (FIG. 3B). Thus, a "strain bottleneck" was generated in the stencil that had the form of a "dogbone" shape. The dogbone shape confined "knobs" of tissue across from one another, but linked the tissues with a shaft within which cells and tissues were subjected to high tensile stress, resulting in cellular alignment (FIG. 3C).

To further diminish "bridging" of tissues across stencil well indentations (e.g. by formation of syncytia that span different micro-wells, thereby causing tissues within to behave as a single, electromechanically connected unit), the depth of wells was increased by increasing the stencil thickness from 50-100 µm (typical thickness for elastomeric membranes) to 250-500 µm. The deeper wells substantially diminished interconnectivity between individual micro-tissues, even when the PDMS surface failed to repel cell adhesion (compare FIGS. 3D and 3E).

Within stencils of optimal thickness and geometry, C2C12 cells formed a pre-stressed tissue with organized stress fibers (FIG. 3F). Sub-optimal geometry (e.g. shafts that are too wide) eliminated this organization (FIG. 3G), and resulted in a "ball" of cells in the middle of the shaft of the dogbone. Hence, narrower canals (relative to the area of the knob regions) tend to generate aligned tissues with synchronous motion. In all studies following this initial work (except as noted), stencils had a thickness of 250-500 µm and the "optimal" dogbone geometry described in FIG. 3F.

Figure 3H:
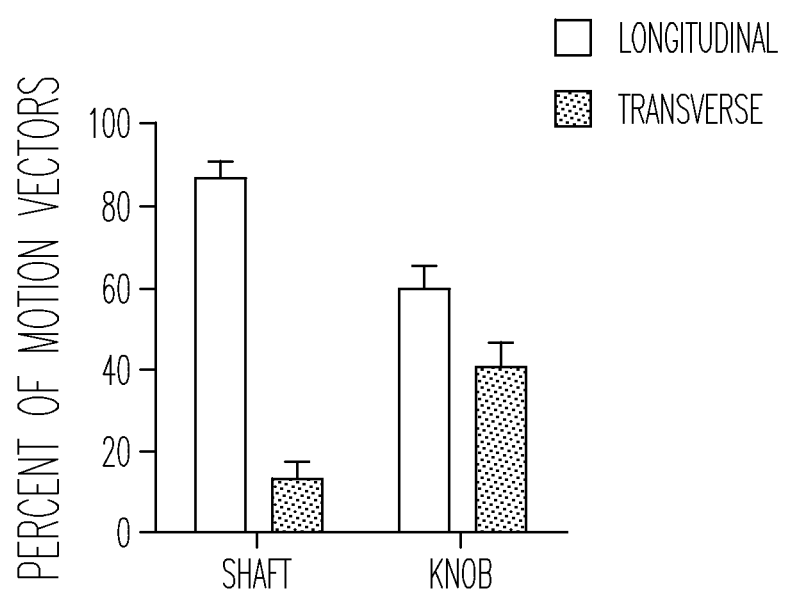
FIG. 3H graphically illustrates that the majority of motion vectors of contractile tissues are along the longitudinal axis of the dogbone microwell shaft, rather than occurring transverse to the shaft. In contrast, motion vectors within the knobs of dogbone microwells occur both longitudinally and transversely.

Beginning five days after seeding cells into micro-tissue molds, the beating parameters of spontaneously beating (non-paced) iPS-CM micro-tissues were analyzed. Analysis revealed that beating occurred in a nearly unidirectional manner, along the longitudinal axis of the dogbone shaft (FIG. 3H; FIG. 4A). Quantifying motion from adjacent dogbone micro-wells revealed beating was slightly asynchronous in unpaced cells, suggesting that no syncytium forms between wells (FIG. 4B). Despite this difference, micro-tissues maintained in RPMI media with B27 supplement all beat at nearly the same rate (FIG. 4B). Micro-tissues incubated in StemPro 34 media beat with a slightly more variable rate from one tissue to the next, but at a basal rate closer to the physiological levels of 1 Hz for human cells (data not shown).

Figure 3I:
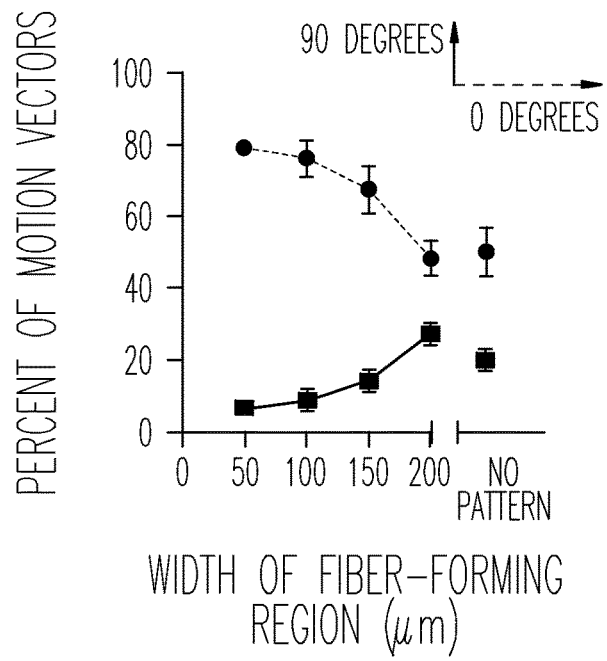
FIG. 3I graphically illustrates a correlation between the width of the dogbone shaft and the percent of motion vectors occurring along the shaft (0 degrees, circular symbols), as well as the correlation between the width of the dogbone shaft and the percent of motion vectors occurring perpendicular to the shaft (90 degrees, square symbols).
Figure 3J:
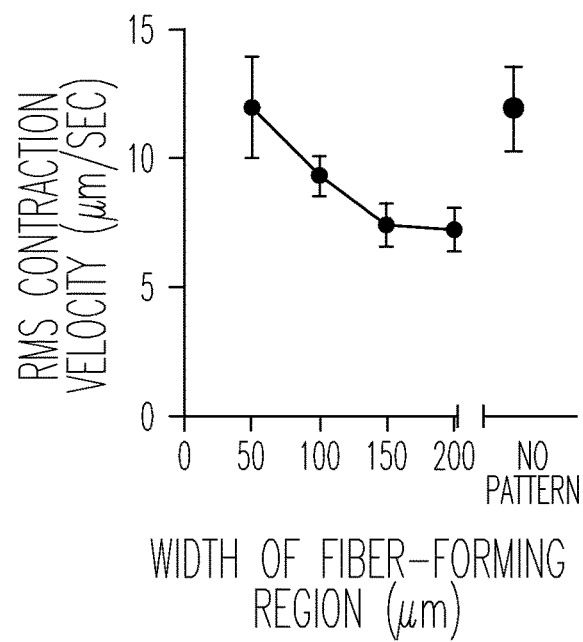
FIG. 3J graphically illustrates that there is an inverse correlation between the width of the dogbone shaft and the contraction velocity of tissues therein.

The directionality and uniformity of contraction, as well as the well-security of the tissues were used to optimize the design of the stencils. As shown in FIG. 3I, the highest percentage of motion (contraction) vectors along the shaft (0 degrees, circular symbols) was observed when the shaft was 50-150 µm wide. Only 5-10% of motion vectors were observed at 90 degrees to the shaft when the shaft was 50-100 µm wide (FIG. 3I, square symbols). Interestingly, the contraction velocity was inversely correlated with the width of the shaft (FIG. 3J). Tissues in a shaft width of about 50 µm contracted faster than those in a shaft that was 150-200 µm wide (FIG. 3J). These data indicate an optimal width for the shaft may be about 100 µm wide.

Figure 3L:
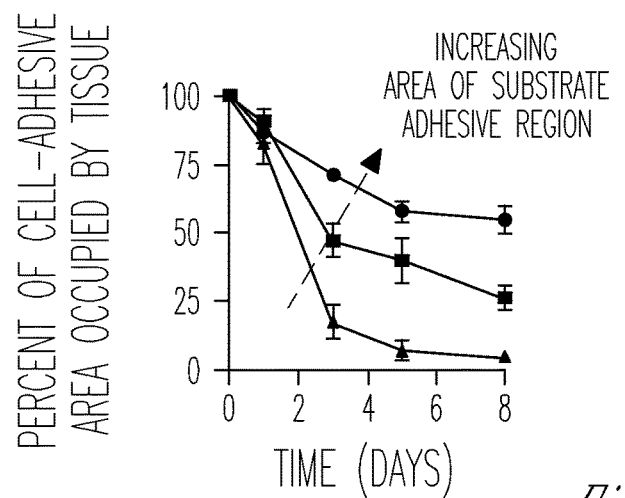
FIG. 3L graphically illustrates the percentage of tissues that remained attached to microwell knobs over time as a function of microwell knob area. More micro-tissues remained attached to the microwells that have knob areas of 500 µm×500 µm (circular symbols), than to microwells that had knob areas of 250 µm×250 µm (square symbols), or to microwells that had knob areas of 100 µm×250 µm (triangle symbols).

However, the knob dimensions also influence the stability of the tissues. As shown in FIG. 3K-3L, tissues adhered to larger knob dimensions better than smaller knob dimensions. For example, after about 5 days of culture, a higher percentage of tissues remained attached to knobs with areas of 500 µm×500 µm than to knobs with areas of 250 µm×250 µm, or to knobs with an area of 100 µm×250 µm (FIG. 3K-3L).

Figure 3M:
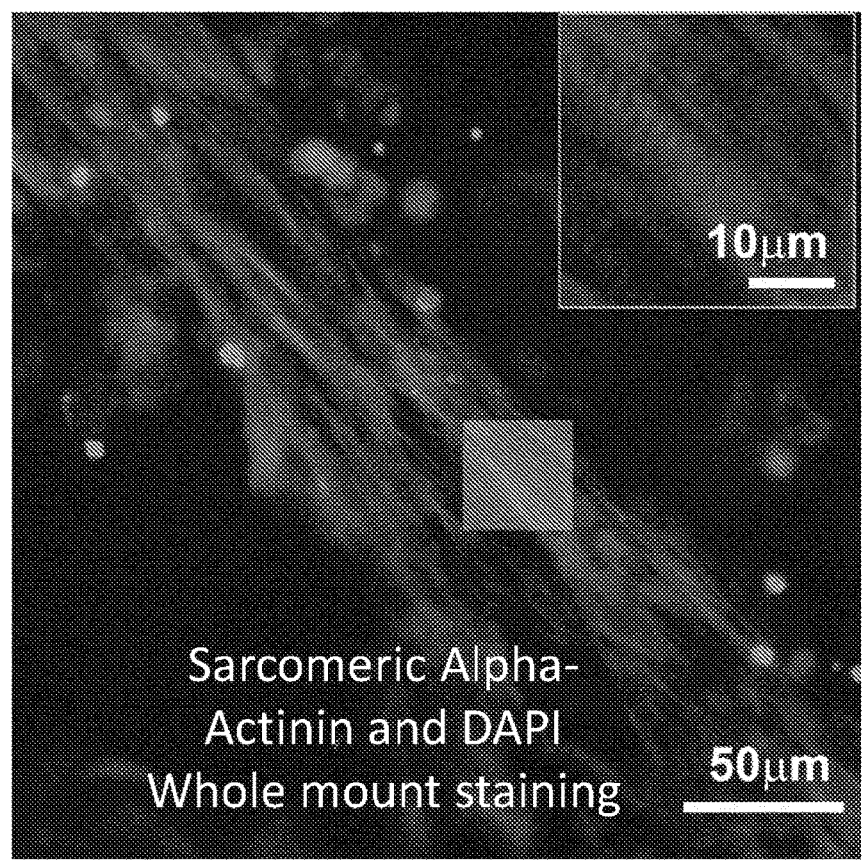
Figure 3N:
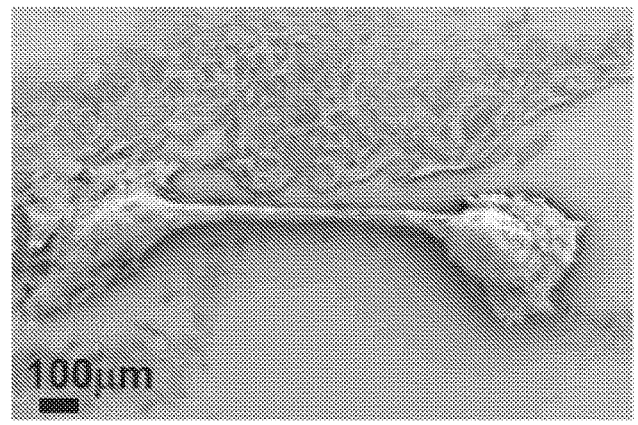
Figure 3O:
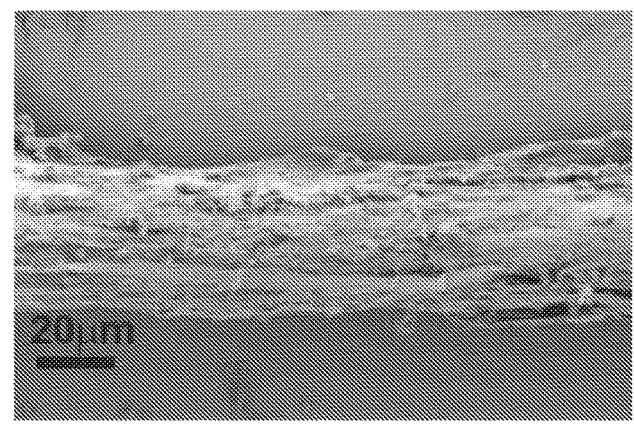
Figure 3P:
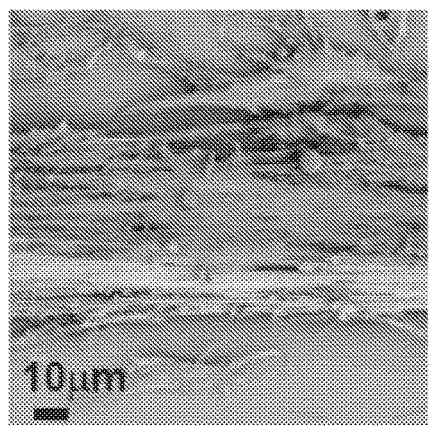
Figure 3Q:
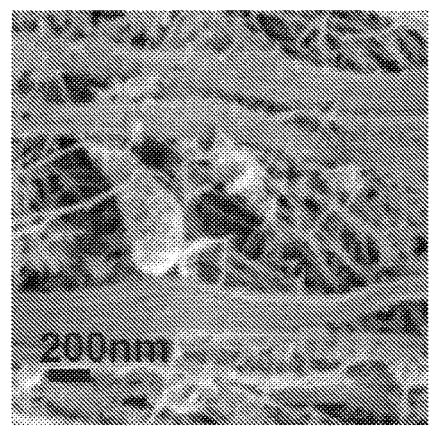

FIG. 3M-3Q show micro-tissues formed from a 50:50 mixture of iPSC-cardiomyocytes and isogenic iPSC-derived fibroblasts, where the whole micro-tissue shown in FIG. 3N was stained to show sarcomeric alpha-actinin (to show the "micro-muscle" structure) and DAPI was used to visualize nuclei (FIG. 3M). FIG. 3N-3Q show scanning electron micrographs of the entire micro-tissue (FIG. 3N), the micro-tissue shaft (FIG. 3O), an expanded view of the micro-tissue shaft, illustrating the alignment of myofilaments therein (FIG. 3P), and sub-micron scale filaments within the micro-tissue knob (FIG. 3Q). Hence, the methods described herein are useful for forming "micro-muscles" that can be used a muscle models for experimental testing.

EXAMPLE 3

Figure 4C:
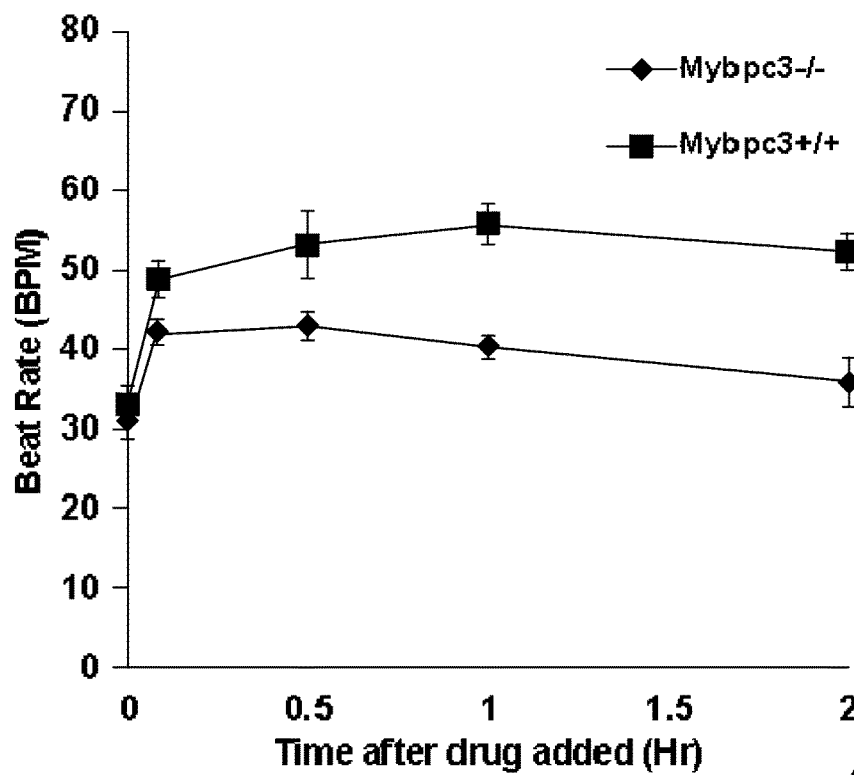
Figure 4D:
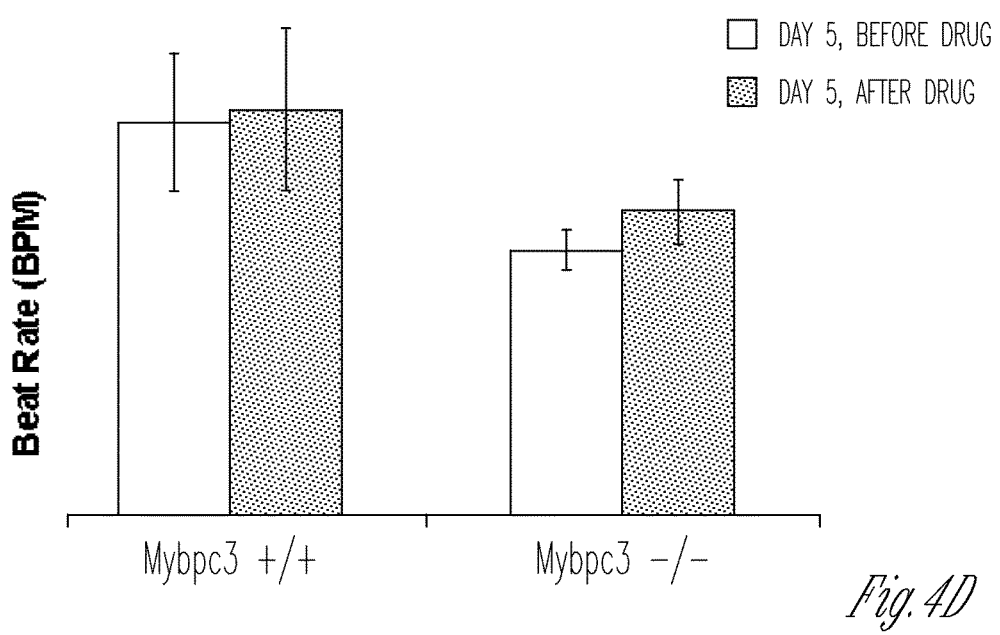
Figure 4E:
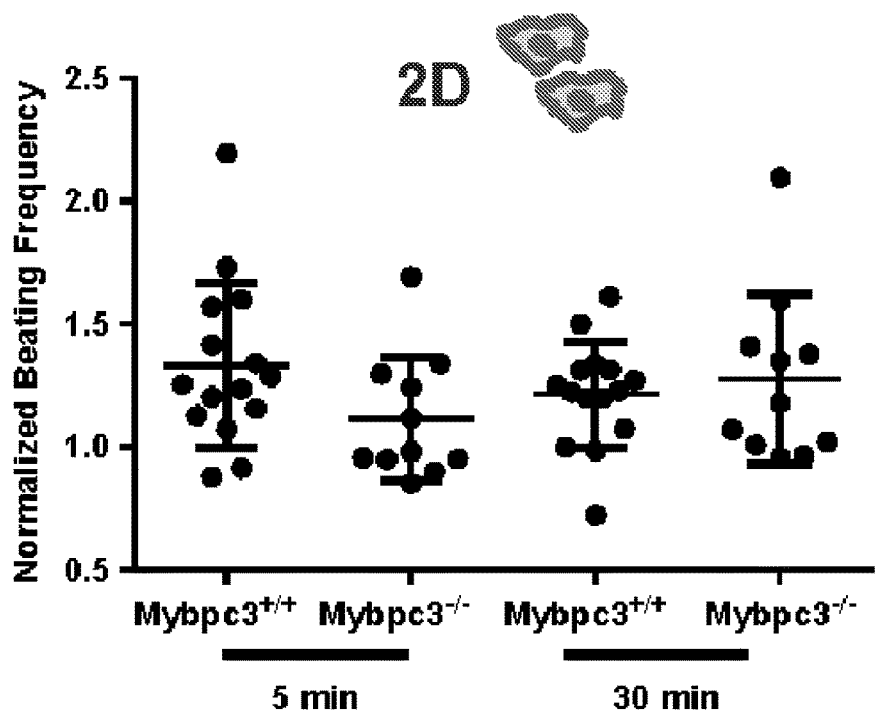
Figure 4F:
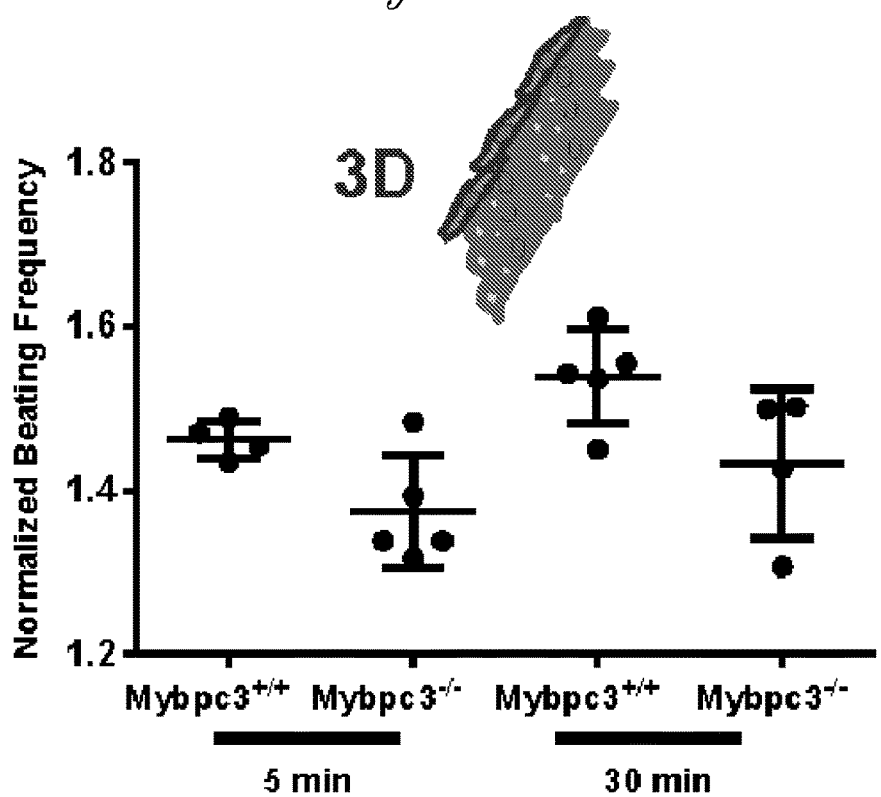

Physiology of Human Induced Pluripotent Stem Cell Derived Cardiomyocytes in Micro-Tissues To model hypertrophic cardiomyopathy, MYPBC3 was knocked out of wild type iPS. The cardiomyocytes derived from MYPBC3$^{-/-}$ iPS had a similar basal beat rate compared to their wild type counterparts (FIG. 4C). However, upon both short-term (30 minutes) and chronic (5 days of daily dosing) exposure to the β-adrenergic agonist isoproterenol, MYBPC3$^{-/-}$ micro-tissues exhibited a blunted decrease in beat-rate (e.g. a chronotropic response; FIG. 4C-4D).

iPS-CM in unpatterned, standard two-dimensional (2D) culture exhibited much more variability in their basal beat rate and in their drug response than the three-dimensional (3D) tissues generated from iPS-CM using the stencils (FIG. 4E-4F). In particular, the beating frequency trends of 2D cultured cells were more disperse and their beating patterns were less distinct than observed for the 3D tissues generated using the stencils (FIG. 4E-4F).

Figure 4G:
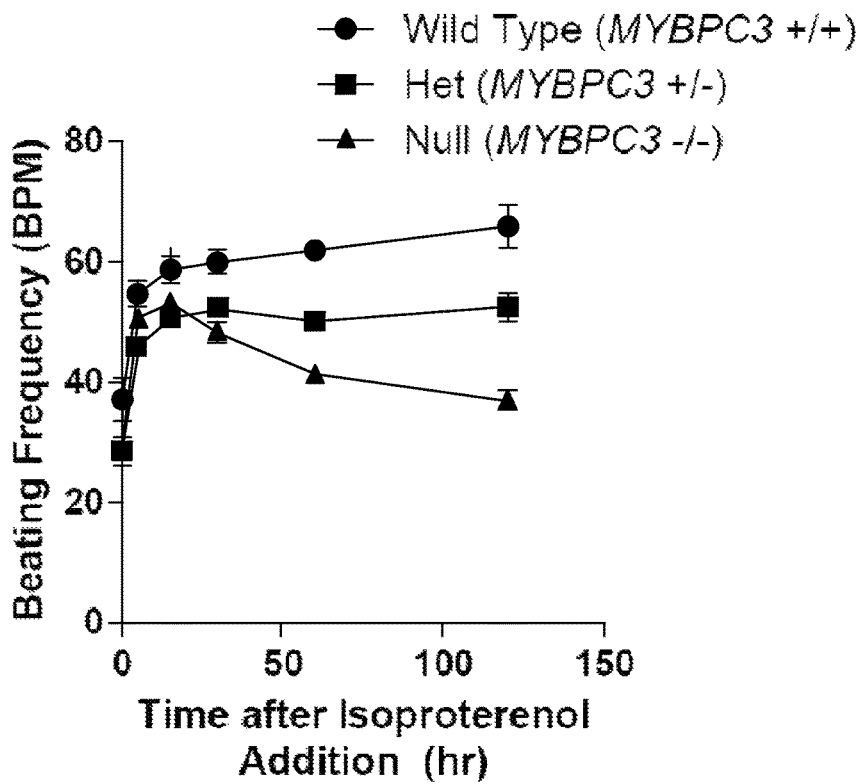
Figure 4H:
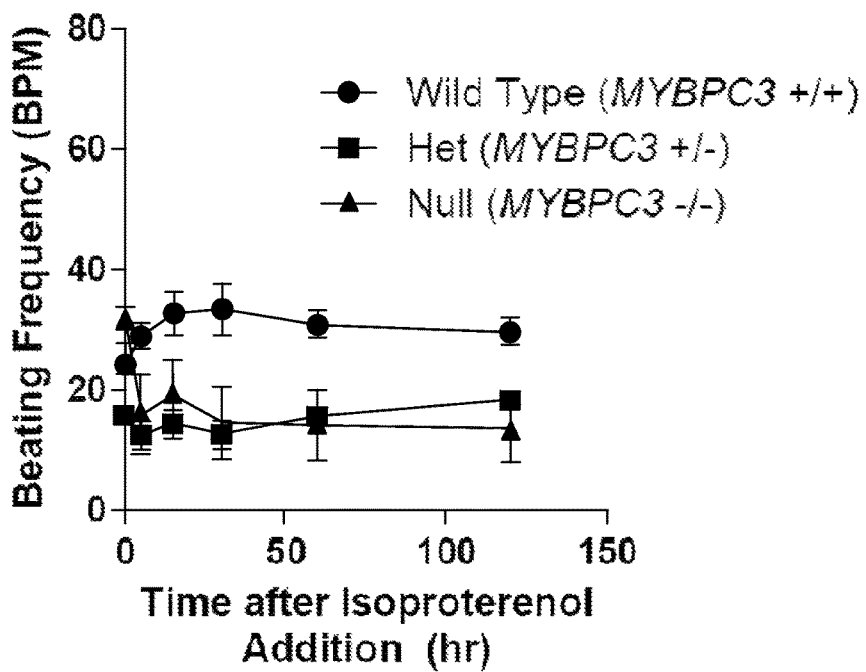

FIGS. 4G and 4H further illustrate that micro-tissues generated from mutant cells are excellent models of human diseases. Micro-tissues were generated within the dogbone-shaped microwells described herein from three different cell types: wild type MYPBC3$^{+/+}$ iPS, heterozygous MYPBC3$^{+/-}$ iPS, and null MYPBC3$^{-/-}$ iPS. As shown in FIGS. 4G, isoproterenol differentially affected the beating frequencies and the drug responses rates of the micro-tissues. FIG. 4G shows that wild type cells exhibited the greatest increase in beating frequency in response to isoproterenol, and that while the beating frequencies of both the heterozygous and null MYPBC3 tissues initially increased in response to isoproterenol, the null MYPBC3$^{-/-}$ iPS tissues returned to a lower beating frequency significantly faster than either of the heterozygous or wild type MYPBC3 tissues (FIG. 4G). The beating frequency of the heterozygous MYPBC3 tissues in response to isoproterenol was distinct from the beating frequencies of wild type and null MYPBC3 tissues: less than the wild type MYPBC3 tissues but greater than the null MYPBC3 tissues (FIG. 4G). However, upon repeated exposure to isoproterenol, the differences heterozygous and null MYPBC3 tissue responses became less significant (FIG. 4H). Hence, prolonged adrenergic stress revealed a functional deficit in heterozygous and homozygous null MYBPC3 micro-tissues. These data illustrate that the micro-tissues generated as described herein are excellent models of disease states, and that the tissues can exhibit the physiological effects of even subtle genetic changes that can be present in human populations.

In additional studies on wild type iPS-CM micro-tissues, the two-dimensional iPS-CM monolayers tended to exhibit erratic/unpredictable responses to isoproterenol (FIG. 5A). At high doses, some 2D-cultured cells and cell clusters stopped beating (FIG. 5A1), but no such effects were observed for 3D-cultured micro-tissues generated within stencil wells (FIG. 5A5). The behavior observed for 3D-cultured tissues formed within the stencil wells was more consistent with previous data from studies involving healthy patients infused with isoproterenol (Brown 1983).

Figure 5B:
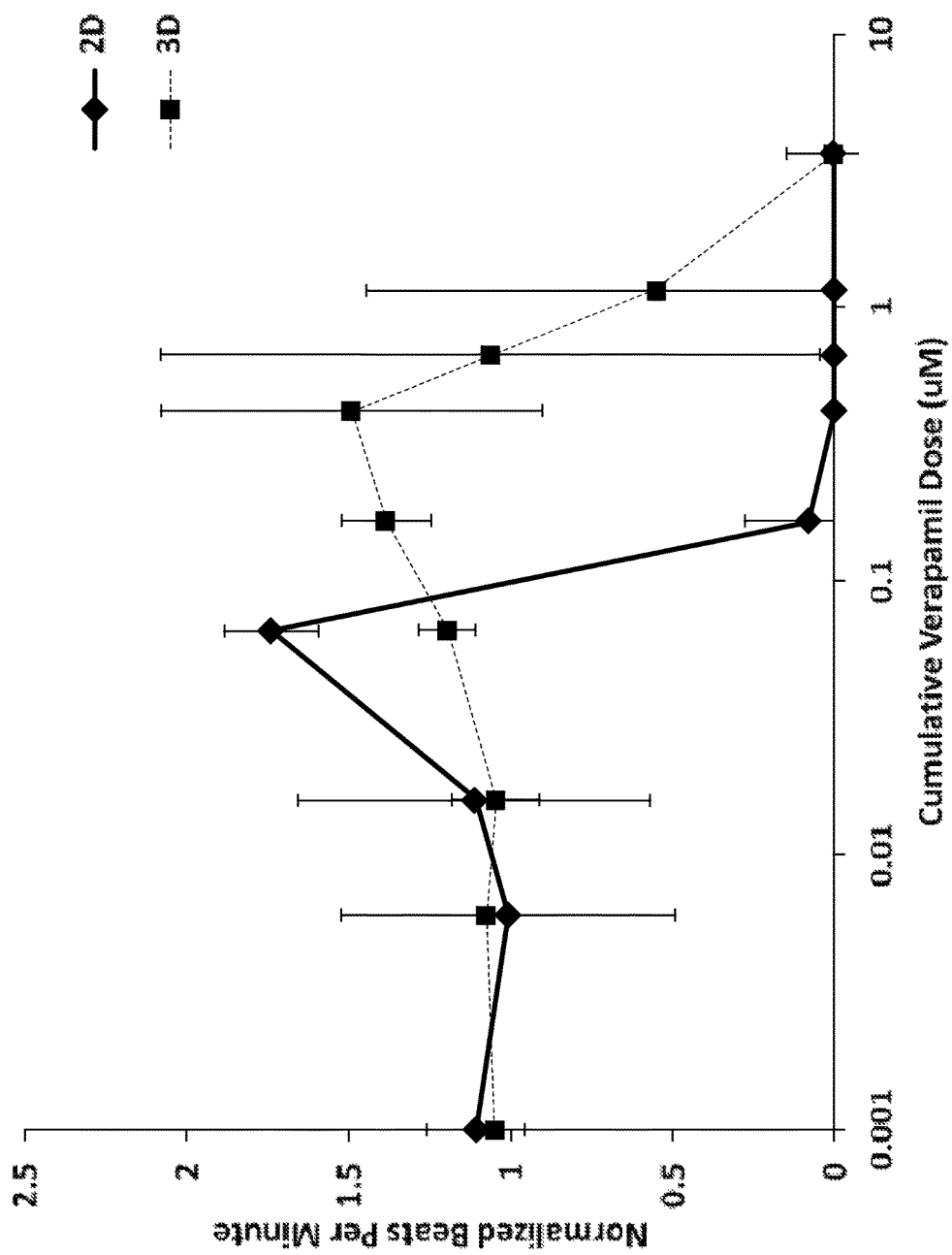

Furthermore, when cultured within the stencil wells, micro-tissues formed from wild type iPS-CM exhibited a higher IC$_{50}$ value for verapamil compared to the same cells when cultured in non-patterned, 2D monolayers (FIG. 5B). Verapamil is a drug that agonizes cardiomyocyte beating via calcium and antagonizes potassium channels. The higher IC$_{50}$ for stencil-generated micro-tissues is similar to results observed by Navarrete (2013) for mature (day 80) embryoid-body derived cardiomyocytes.

Figure 5C:
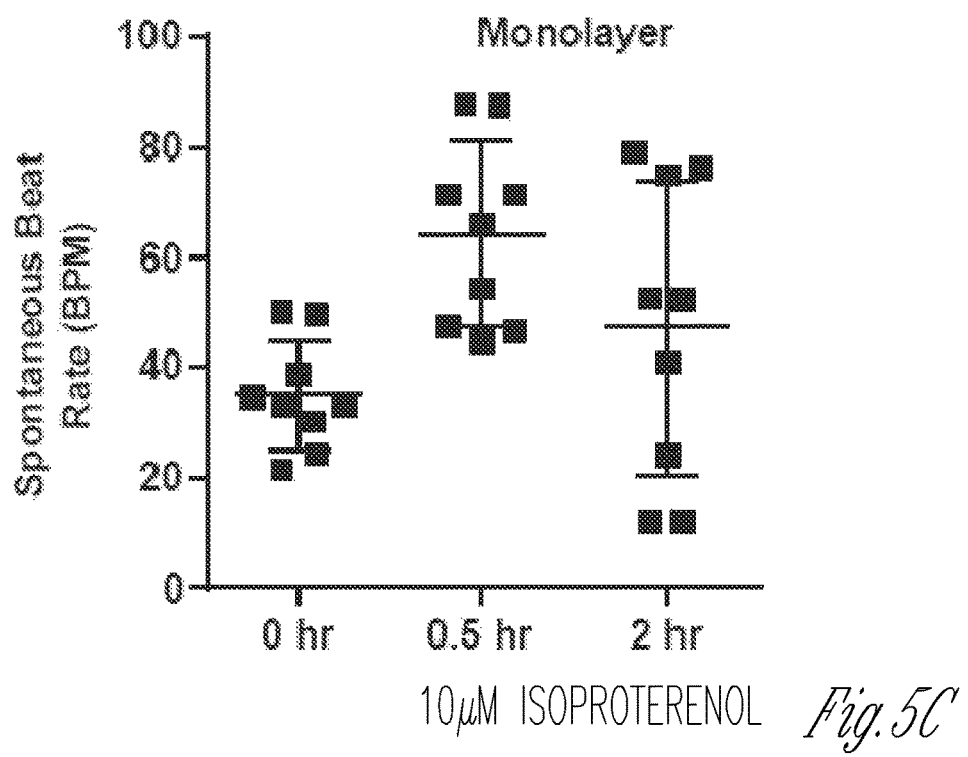
Figure 5D:
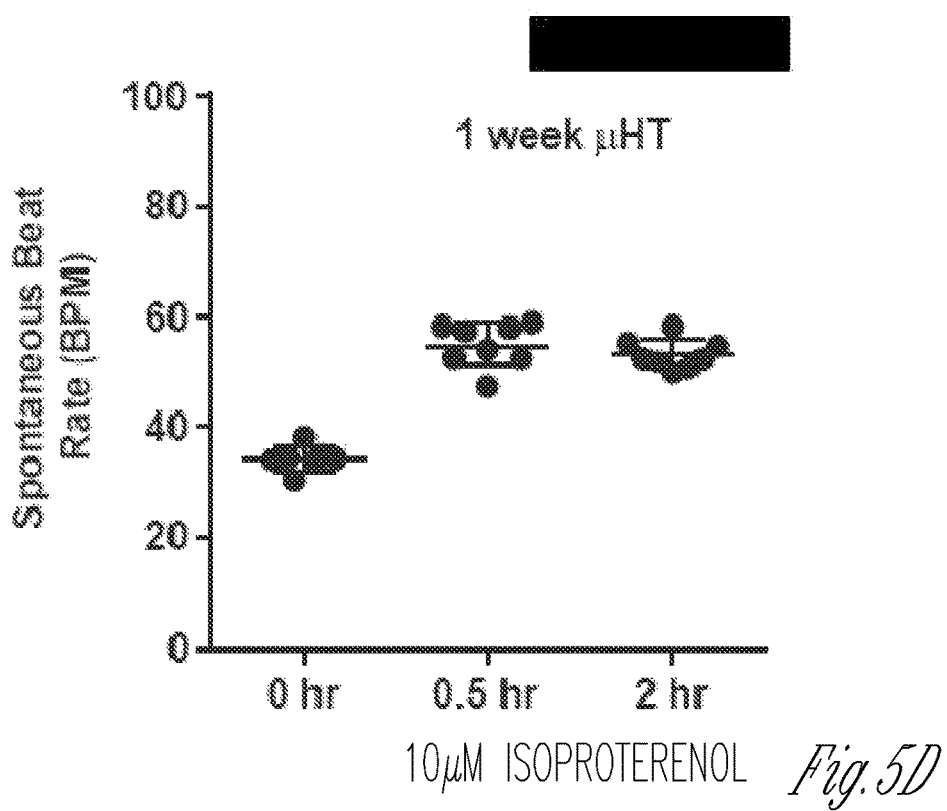

FIGS. 5C-5D further illustrate that the responses of independent micro-tissues generated as described herein exhibit more reproducible drug responsiveness than do two-dimensional monolayers of cells. As shown in FIG. 5C, the beat rate of cell monolayers in response to isoproterenol varies significantly from one test to the next. However, the responses of three-dimensional micro-tissues to isoproterenol are highly reproducible (FIG. 5D).

EXAMPLE 4

Analysis of Cardiomyocyte Structure and Biomarkers in Micro-Tissues

To correlate physiologic responses to cardiomyocyte structure and biomarkers, hydrogel inversion was applied to paraformaldehyde fixed micro-tissues.

Figure 6E:
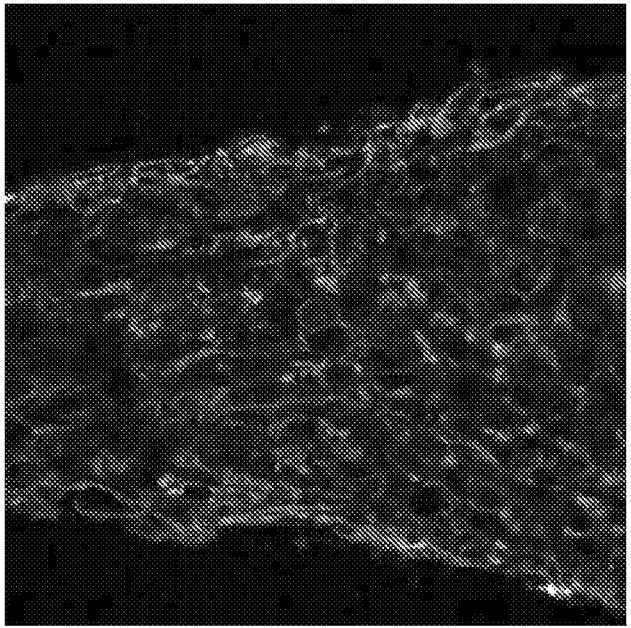
Figure 6D:
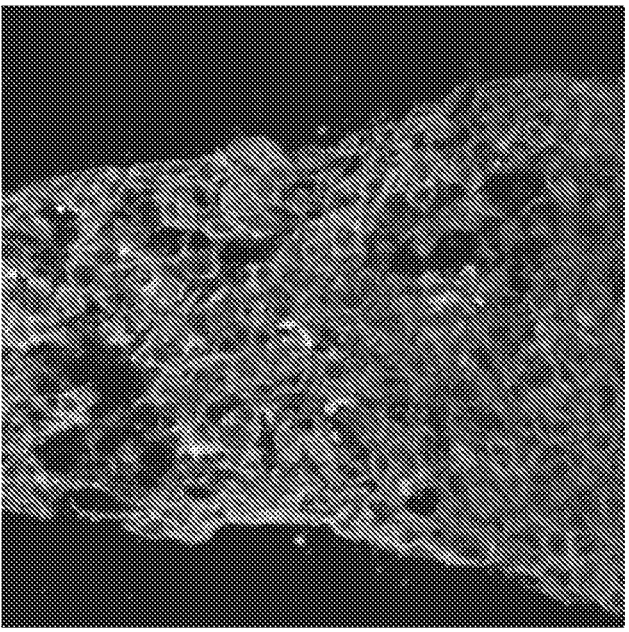

In preliminary studies, wild type iPS-CM micro-tissues were sectioned to visualize cell size and sarcomere integrity. These studies indicated that, despite the fact that the input population used to form micro-tissues was less than 75% pure via FACs analysis of cardiac troponin I (data not shown), the vast majority of cells in a given slice were cardiomyocytes that stained positive for sarcomeric actinin (FIG. 6). The longitudinal alignment of sarcomeres was consistent with the longitudinal beating observed within these micro-tissues.

EXAMPLE 5

Micro-Tissues with iPS-CM with the GCaMP6f Calcium Indicator

Induced pluripotent stem cells genetically modified to express the GCaMP6f calcium indicator gene product, and then differentiated into cardiomyocytes (iPS-CM). Micro-tissues were made with iPS-CM harboring the GCaMP6f calcium indicator, to allow continuous recording of calcium flux as illustrated in FIG. 8.

Figure 8A:
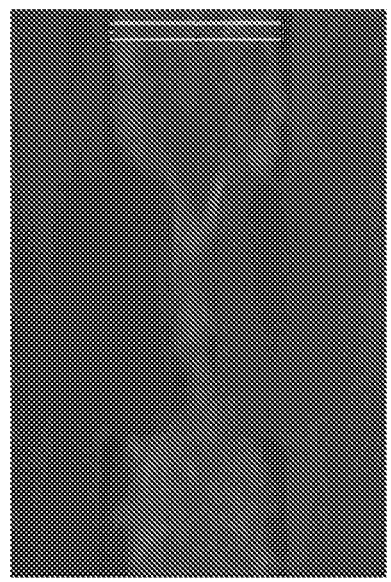
Figure 8B:
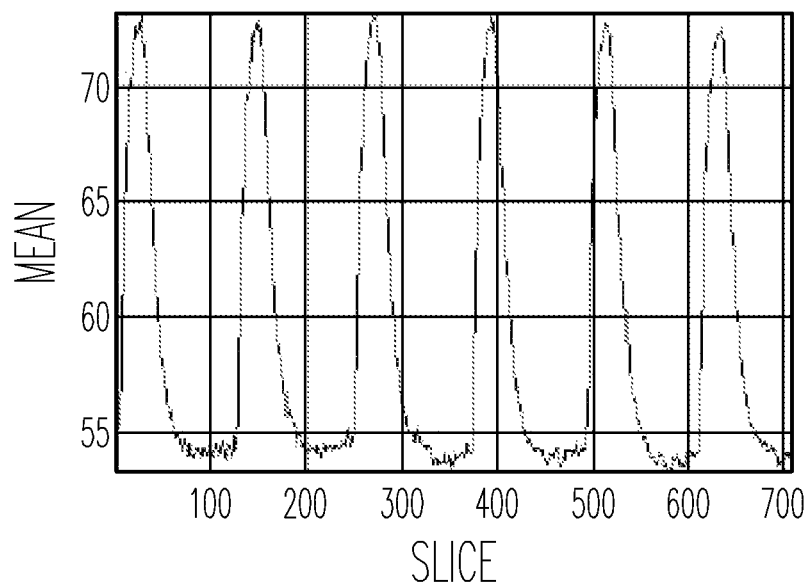

FIG. 8A identifies the region monitored for the fluorescence signal of the GCaMP gene product (light box near the top of the micro-tissue image). As shown in FIG. 8B, the signal is repetitive and the intensity of the signal is proportional to intracellular calcium concentration. FIG. 8C shows calcium flux as measured by expression of GCaMP in unpaced iPS-CM micro-tissues (FIG. 8C1), and in iPS-CM micro-tissues subjected to 1 Hz (FIG. 8C2) and 2 Hz (FIG. 8C3) electrical field pacing.

FIG. 8D-8E illustrate the functional maturation of iPS-CM-derived micro-tissues (µHT, micro-heart tissues). After 1 or 2 weeks of incubation in the stencil microwells, the micro-tissues were paced at 1 Hz for analysis of inotropy. A comparison of the synchronicity and drug response of 1 week micro-tissues (FIG. 8D) with 2 week micro-tissues (FIG. 8E) indicates that the calcium flux of 'younger' micro-tissues that were incubated for 1 week were more synchronous than the 'older' micro-tissues that were incubated for 2 weeks. Both younger and older micro-tissues responded to isoproterenol, but the younger tissue responses were somewhat more synchronous.

EXAMPLE 6

Micro-Tissues formed by Mixing Different Cells of Defined Phenotype and Genotype The Example illustrates some of the properties of micro-tissues formed from mixed cells.

Cells were obtained from a healthy volunteer, induced pluripotent stem cells were generated and then differentiated into either cardiomyocytes (iPS-CM) or fibroblasts (EB-fibroblasts), referred to as "wild type" cells. Isogenic, wild type iPS-CM or MYBPC3$^{+/-}$ and MYBPC3$^{-/-}$ iPS-CM were then combined with the EB-fibroblasts to form mixed tissues. The MYBPC3 knockout cells harbor a constitutively expressed mCherry markers that express a red fluorescent protein that allows the MYBPC3$^{-/-}$ cells to be distinguished within tissues. As shown in FIG. 9, the cardiomyocytes (lighter areas, red in the original) aggregated within the center of micro-tissues that formed. These results illustrate how boundary constraints applied by stencils with specific geometries combine with cells' propensity for self-assembly, to cause formation of structurally complex micro-tissues with multiple cellular components.

The use of purified, genetically distinct cell populations is especially important when identifying heart tissue pathophysiology that is related to supporting cells (e.g. endothelial cells, fibroblasts, peripheral neurons). For example, hereditary central nervous system disorders such as sudden unexplained death of epilepsy (SUDEP) involve impaired sympathetic cardiac innervation (Finsterer & Wahbi, *J. Neurol. Sci.* (2014). Furthermore, cells in which drug addiction can be modeled by genetically engineered signaling pathways activated by bioorthogonal drugs (Conklin et al., *Nat. Methods* 5(8): 673-78 (2008)), light (Deisseroth, *Nat. Methods,* 8:26-29 (2011)) or other modalities. Such models can identify whether cardiotoxic effects of drugs occur due to a primary insult in cardiomyocytes, or secondarily, due to an insult in other cell types. Two-way communication between cardiomyocytes and neurons is further important in patients' ability to detect cardiac ischemia, and ischemic death of cardiomyocytes specifically within the device could be mimicked by using genetically encoded, doxycycline inducible "death switches," or over-expression of polypeptides that are pathologic and activated during cardiac ischemia (Razzaque et al., *Circ Res* 113(5): 553-61 (2013)). In these instances, neuronal response to injury of innervated cardiomyocytes could be detected through markers, such as GCaMP, engineered specifically into the cell population used to form the neuronal compartment.

Finally, simply by virtue of the fact that micro-tissue can be assembled from independently produced, defined, engineered cell populations, genetically engineered or non-engineered cells can be modified transiently or permanently with synthetic molecules or scaffolds that enable control over cell-cell interactions, or which allow distinct cell populations to be "pre-loaded" with devices that elute drugs either from an intracellular or extracellular compartment.

This foregoing types of information would be impossible to glean from studies on purified cardiomyocytes, and difficult to ascertain without the ability to engineer biology of specific cells within the tissue.

EXAMPLE 7

Micro-Tissues can be Evaluated on Existing Apparatuses for Muscle Testing

This Example illustrates that micro-muscles can be mounted onto apparatus typically used for adult rodent muscle, and macro-scale hESC-CM Engineered Heart Muscles, and that the micro-muscles exhibit behavior similar to such muscles (i.e., the micro-muscles stay intact upon being stretched and increase their passive tension when stretched).

Figure 10A:
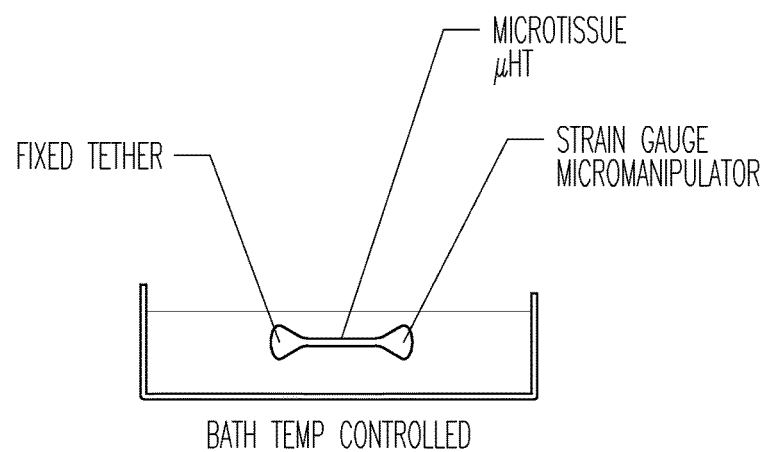
Figure 10B:
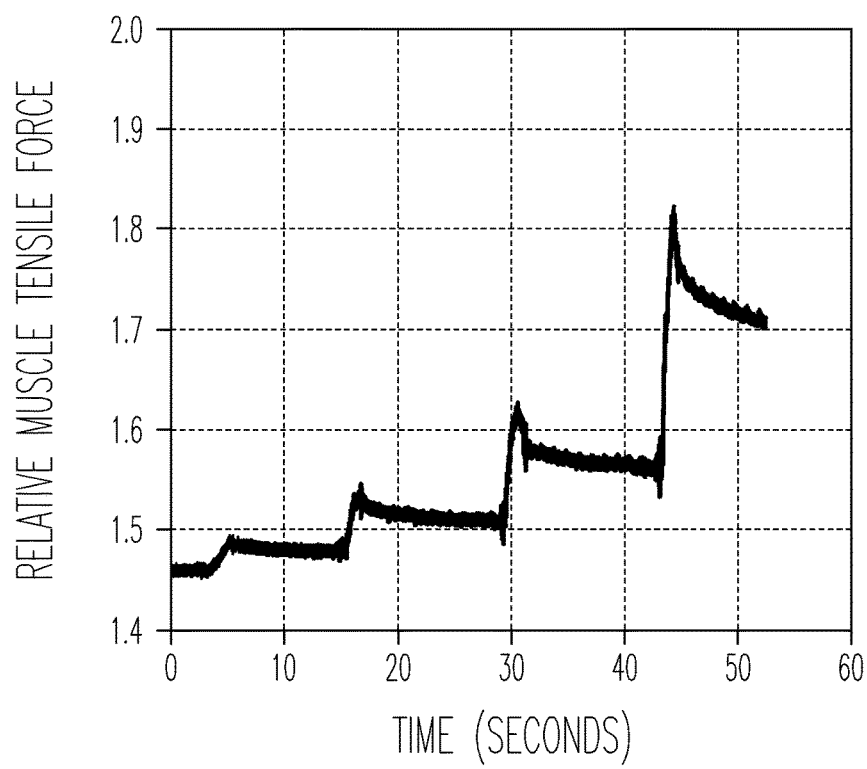

Approximately 3000 cardiomyocytes were seeded into the stencil microwell as a mixture of 50% iPS-cardiomyocytes and 50% EB-fibroblasts, and the cells were incubated for three weeks to form the micro heart tissue (µHT) or micro-muscle. FIG. 10A is a schematic diagram of a micro-muscle on a strain gauge micromanipulator. FIG. 10B illustrates the relative muscle tensile force of such cardiac micro-muscles as a function of time.

For comparison, FIG. 10C1-10C3 shows a re-drawing of results obtained by Tulloch et al. for an engineered heart macro-muscle that was generated from approximately two million cardiomyocytes differentiated from human embryonic stem cells (hESC-CM), after the hESC-CM were incubated in a stencil for three weeks to generate an engineered heart muscle (EHM) that contained about 53% hESC-CM. See Tulloch et al., *Circ Res.* 109(1):47-59 (2011).

EXAMPLE 8

Micro-Muscle Responses to Tension (Stretching) and Electrical Field Pacing

This Example illustrates some of the physiological properties of micro-muscles formed from cell populations containing cardiomyocytes (iPS-CM).

Figure 11A:
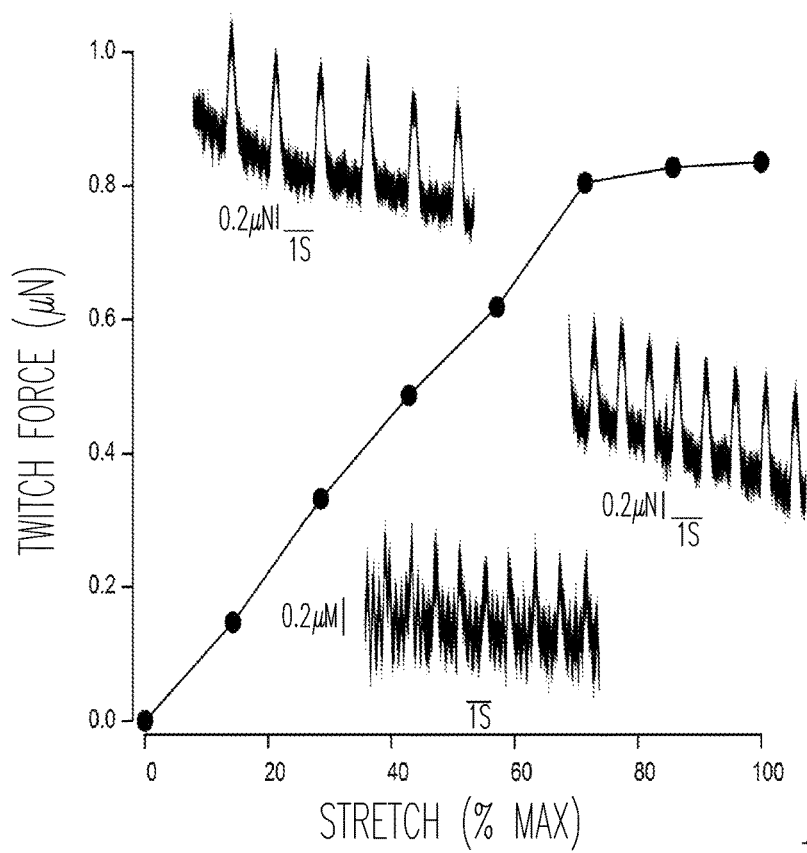
FIG. 11A-11F show that micro-muscles exhibit Frank-Starling behavior (twitch force increases with increasing passive tension) and that micro-tissues are responsive to electrical field pacing.
Figure 11B:
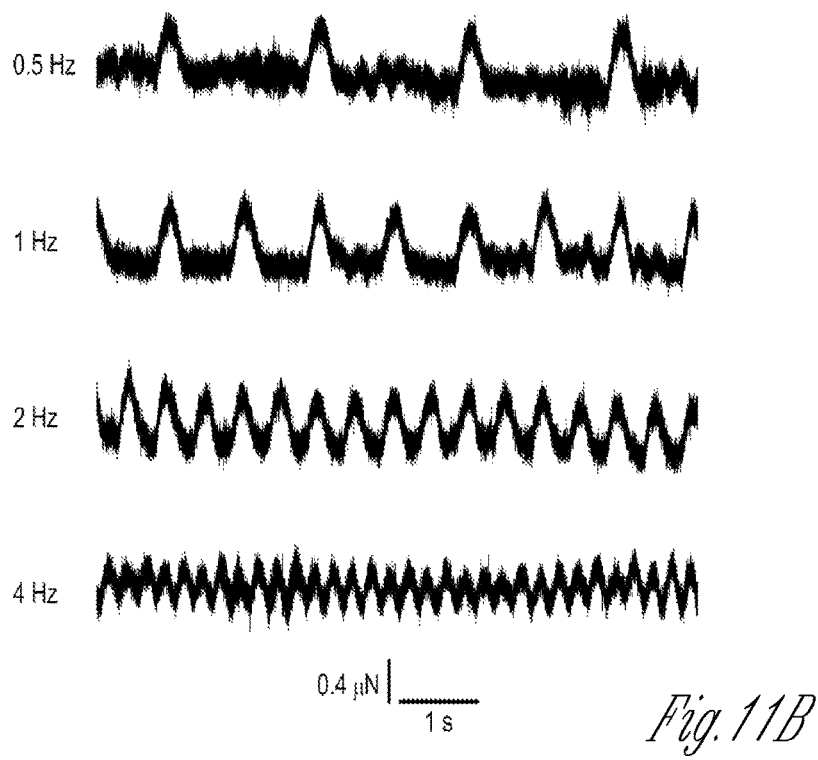

FIG. 11A illustrated the twitch force of micro-muscles as a function of stretch (percent of maximum stretch). As illustrated, the micro-muscles exhibit Frank-Starling behavior where their twitch force increases with increasing passive tension. In addition, the micro-muscles are also responsive to electrical field pacing (FIG. 11B).

Figure 11C:
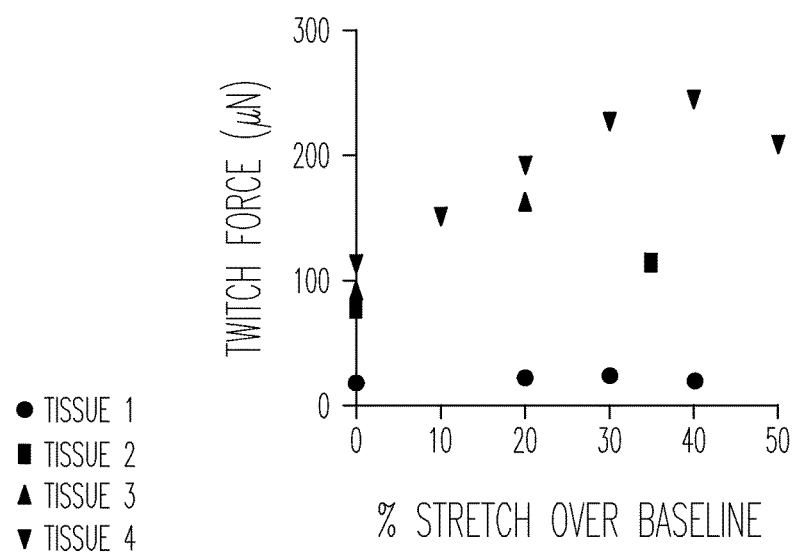

FIG. 11C illustrates that healthy micro-muscles (triangle symbols) exhibit consistent Frank-Starling behavior, whereas micro-muscles that have been damaged (circular and square symbols) do not exhibit consistent Frank-Starling behavior. Hence, when damaged, micro-tissues exhibit physiologically relevant disease symptoms, and are an excellent model of damaged cardiac muscle.

EXAMPLE 9

Calcium Dose Responses of Micro-muscles

This example illustrates that micro-muscles exhibit calcium dose responses that are like macro-heart tissues.

Representative micro-muscle heart tissues were generated by seeding small numbers of cardiomyocytes into stencil microwells as described herein. Separate micro-muscles were then contacted with different extracellular calcium concentrations.

Figure 11D:
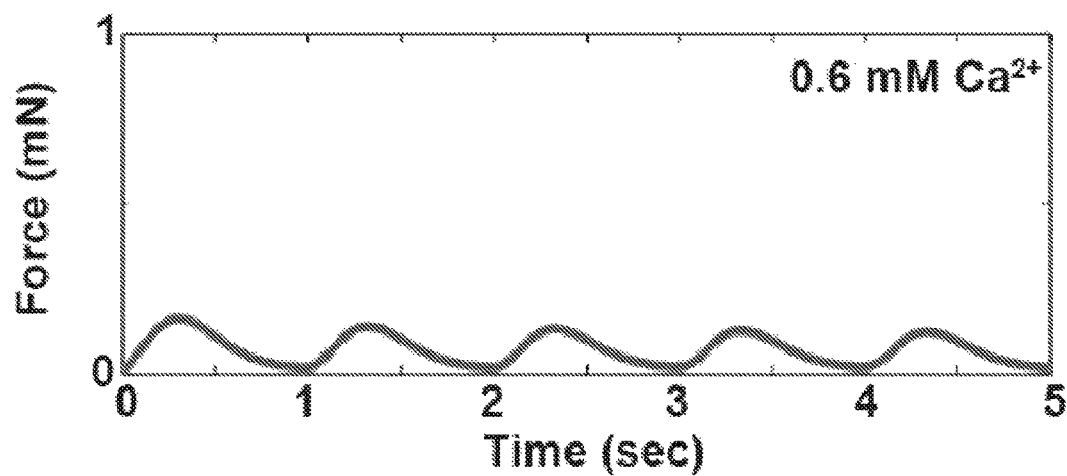
Figure 11E:
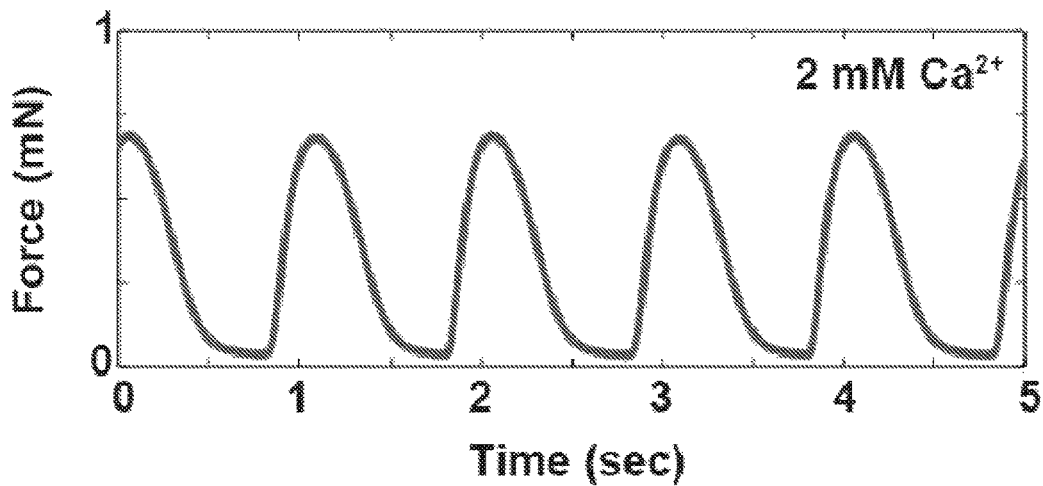
Figure 11F:
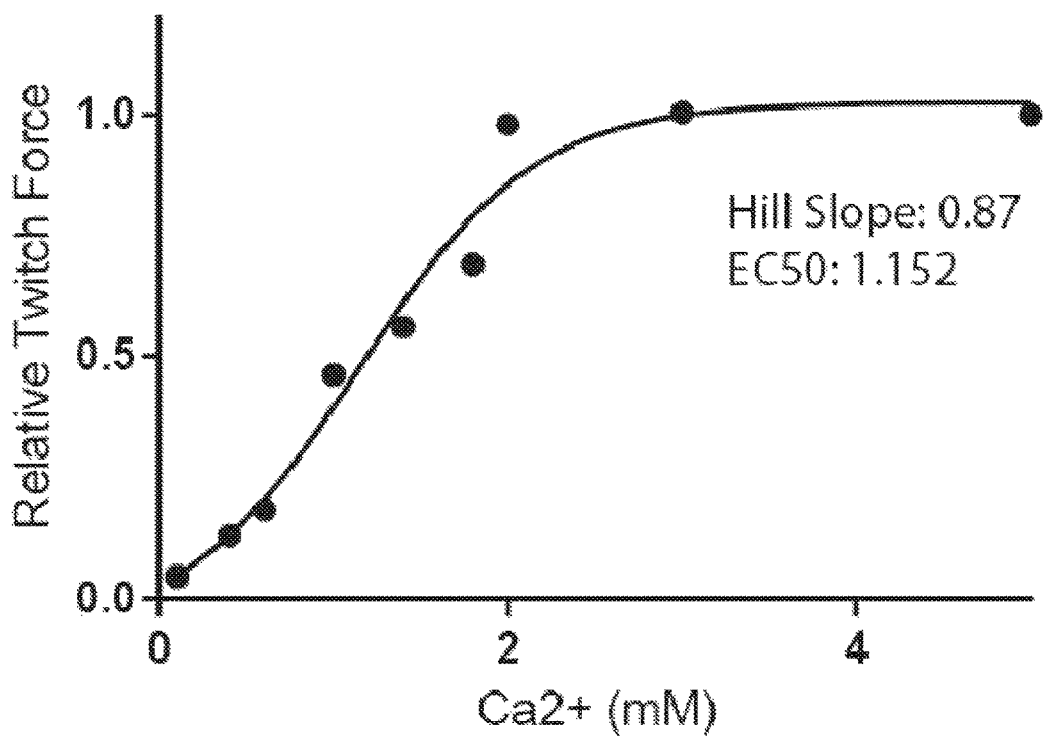

FIGS. 11D-11F illustrate calcium dose-responses of micro-muscles generated from cell populations containing cardiomyocytes. As illustrated, the twitch force of micro-muscles dramatically increases as the extracellular calcium concentrations increase.

These data illustrate that the micro-muscles exhibit physiological characteristics that are comparable to much larger tissue-engineered heart muscles. For example, the micro-muscles exhibit similar increases in twitch force (during beating) to those observed in macro-scale engineered heart muscle (containing more than $5 \times 10^5$ cells/tissue) that are typically formed from human embryonic stem cell derived cardiomyocytes.

Not only do micro-muscles behave comparably to much larger engineered heart tissues, but the micro-tissues respond appropriately to inotropic stimuli.

EXAMPLE 10

High-Throughput Engineering of Micro-Tissues

This Example illustrates that generation of micro-tissues can be by high-throughput procedures.

Figure 12A:
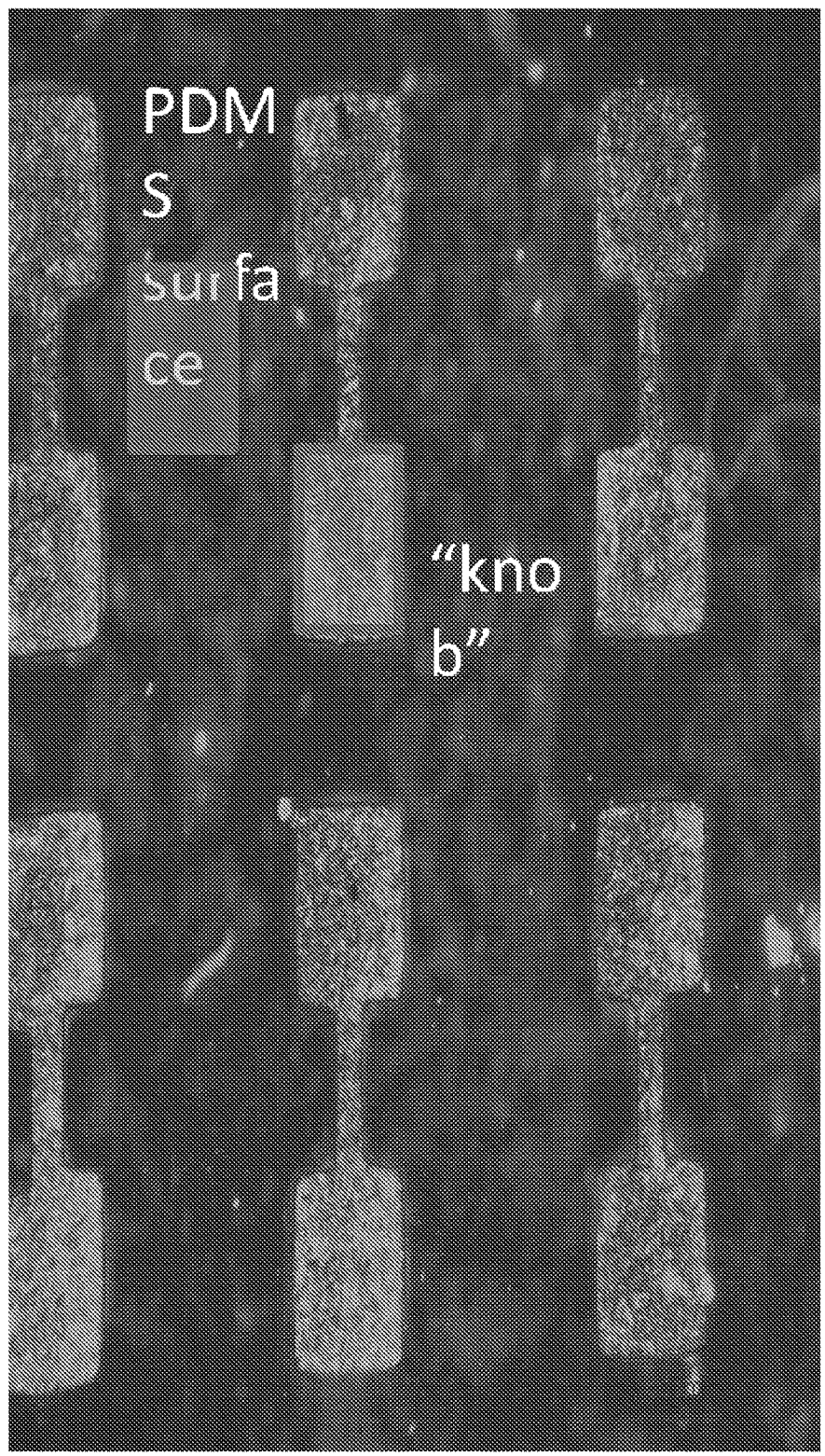
FIG. 12A-12C illustrate that the stencil is readily adapted for high throughput generation of micro-tissues, for robotic fluid manipulation of cells and micro-tissues, and that the effects of such high throughput and robotic manipulation can be monitored by observing signals from the micro-tissues.
Figure 12B:
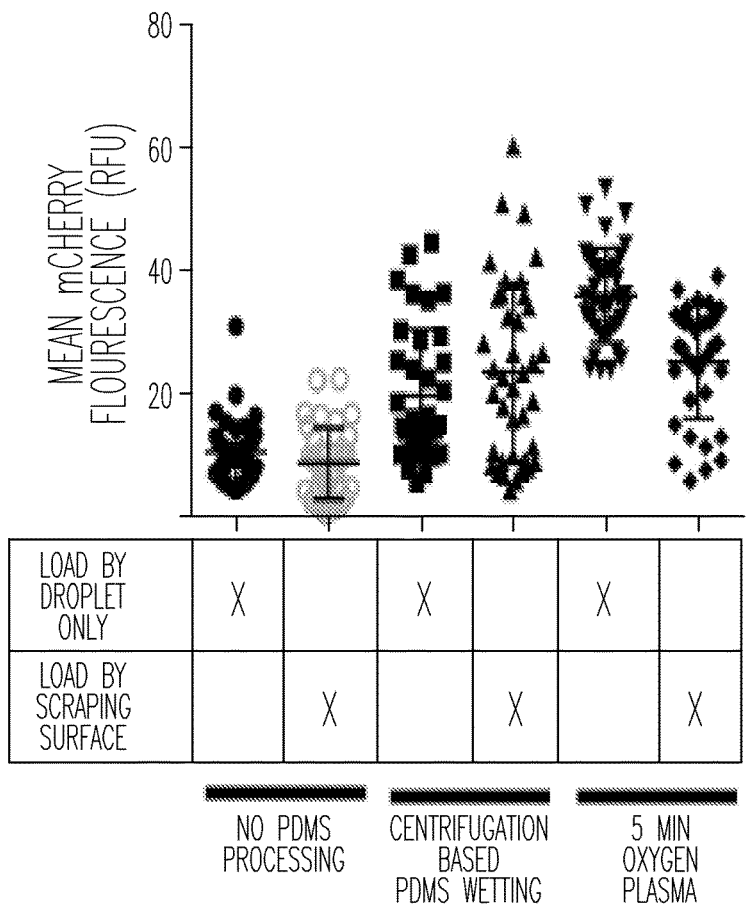
Figure 12C:
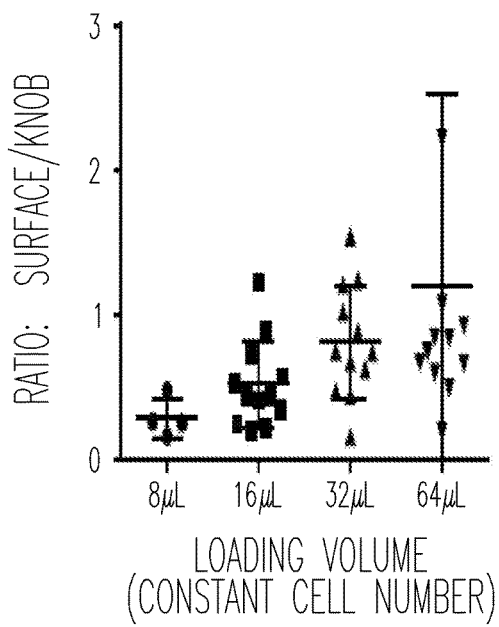

FIG. 12A-12C illustrate that the stencil and other materials engineered for higher throughput, and for robotic fluid handling of cells and micro-tissues are compatible with effective micro-muscle formation. FIG. 12A shows an image of a stencil, illustrating the surface of the PDMS material employed in the stencil, as well as the micro-wells, each with a knob and a canal. FIG. 12B graphically illustrates the mean mCherry fluorescence of mCherry-expressing micro-muscles where the cells that generated the micro-muscles were loaded by either a droplet (only) or by scraping the surface of the stencil to load the cells into microwells. Also shown in FIG. 11B are the processes to which the loaded cells were subjected including no PDMS processing, centrifugation-based wetting of the PDMS stencil, or 5 minutes of oxygen plasma treatment. Current methods involve loading by scraping the cells into wells. However, the microwells can automatically be loaded droplets of cells, which permits faster processing and enables generation of larger numbers of micro-tissues. Also as shown in FIG. 12B, the physiological responses of cells and micro-tissues manipulated by automation (or by manual manipulation) can be monitored by observing the mean mCherry fluorescence.

FIG. 12C graphically illustrates the surface covered by cells upon drop loading different volumes of cells where the cell number of cells loaded was constant. As illustrated, decreased water contact angle achieved by making the stencil surface more hydrophilic allows loading of cells into micro-wells by pipetting only, which is a method that is compatible with robotic automation.

REFERENCES

Ankrum J A, et al. Engineering cells with intracellular agent-loaded microparticles to control cell phenotype. *Nat. Protoc.* 2014; 9(2): 233-45.

Bian W, Liau B, Badie N, Bursac N. Mesoscopic hydrogel molding to control the 3D geometry of bioartificial muscle tissues. *Nat Protoc.* 2009; 4(10): 1522-34.

Brown M J, Brown D C, Murphy M B. Hypokalemia from Beta-Receptor Stimulation by Circulating Epinephrine. *New Eng. J. Med.* 1983; 309: 1414-9.

Conklin B R, et al. Engineering GPCR signaling pathways with RASSLs. *Nat. Methods.* 2008; 5(8): 673-8.

Deisseroth K. Optogenetics. *Nat. Methods* 2011; 8: 26-9.

Finsterer J, Wahbi K. CNS-disease affecting the heart: Brain-heart disorders. *J Neurol Sci* 2014, http:/dx.doi/org/10.1016/j.jns.2014.07.003

Folch A, Jo B H, Hurtado O, Beebe D J, Toner M. Microfabricated elastomeric stencils for micropatterning cell cultures. *J Biomed Mater Res* 2000; 52(2): 346-53.

Gartner Z J, Bertozzi C R. Programmed assembly of 3-dimensional micro-tissues with defined connectivity. *Proc. Natl. Acad. Sci. USA* 2009; 106(12): 4606-10.

Gianni L, et al. Anthracycline Cardiotoxicity: From Bench to Bedside. *J Clinc. Oncol.* 2008; 26(22): 3777-84.

Huebsch N, Loskill P et al. Automated video-based contractility analysis of human iPS-derived cardiomyocytes cultured over different spatial scales. In Revision (*Tissue Engineering Part C—Methods*).

Lian X et al. Directed cardiomyocyte differentiation from human pluripotent stem cells by modulating Wnt/β-catenin signaling under fully defined conditions. *Nat. Protoc.* 2013; 8(1): 162-75.

Ma Z et al. Three-dimensional filamentous human diseased cardiac tissue model. *Biomaterials* 2014; 35(5): 1367-77.

McNally et al., *J. Clin. Invest.* 123(1): 19-26 (2013).

Myers F B et al. Robust pluripotent stem cell expansion and cardiomyocyte differentiation via geometric patterning. *Integr. Biol.* 2013; 5: 1495-506.

Navarrete E G, Lian P, Lan F, et al. Screening drug-induced arrhythmia events using human induced pluripotent stem cell-derived cardiomyocytes and low-impedance microelectrode arrays. *Circulation* 2013; 128(11 Suppl 1): S3-13.

Razzaque M A, et al. An endogenously produced fragment of cardiac myosin-binding protein C is pathogenic and can lead to heart failure. *Circ. Res.* 2013; 113(5): 553-61.

Stevens K R et al. InVERT modeling for scalable control of tissue microarchitecture. *Nat. Commun.* 2013; 4:1847.

Tourovskaia A et al. Micropatterns of Chemisorbed Cell Adhesion-Repellent Films using Oxygen Plasma Etching and Elastomeric Masks. *Langmuir* 2003; 19(11): 4754-64.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various features of the invention according to the foregoing description in the specification.

Statements:

1. A device for confining mammalian cells, forcing cellular/tissue alignment and tissue self-assembly, comprising:
   a cell adhesion substrate; and
   a removable elastomeric stencil overlay;
   wherein the elastomeric stencil has one or more cut-out patterned microwells comprising two or more circular, oval, rectangular, square, V-shaped, or triangular holes, each hole joined to an adjacent hole by a canal (shaft); and
   wherein the cell adhesion substrate binds cells within at least the holes of the cut-out pattern.

2. The device of statement 1, wherein the removable elastomeric stencil comprises polydimethylsiloxane (PDMS), surface functionalized PDMS, polyimide, polyurethane, SU8, thermoplastics, poly(methylmethacrylate) (PMMA), polycarbonate (PC), polystyrene (PS), polyethylene terephthalate (PET), poly(vinyl chloride) (PVC), fibrin, glass, quartz, silicon, hydrogel forming polymers (e.g. polyacrylamide, polyethylene glycol, alginate, agarose, gelatin, collagen) or any combination thereof.

3. The device of statement 1 or 2, wherein each of the microwells has a depth of at least 250 μm or at least 500 μm.

4. The device of any of statements 1-3, wherein each of the microwells has a depth of about 200 μm to about 1000 μm, or about 250 μm to about 750 μm, or about 250 μm to about 500 μm.

5. The device of any of statements 1-4, wherein each of the microwells has a volume of about 0.05 μL to about 2 μL, or of about 0.1 μL to about 1.0 μL, or of about 0.1 μL to about 0.5 μL.

6. The device of any of statements 1-5, wherein each of the canals of each of the microwells is about 10 μm to about 200 μm wide, or about 50 μm to about 150 μm wide, or about 75 μm to about 125 μm wide.

7. The device of any of statements 1-6, wherein each of the canals of each of the microwells is about 100 μm to about 2000 μm in length.

8. The device of any of statements 1-7, wherein the width of each of the canals compared to the width of the holes is about 1:3 to about 1:10, or about 1:3 to about 1:7, or about 1:3 to about 1:5, or at least about 1:4.

9. The device of any of statements 1-8, wherein each of the holes has an area of about 50 µm² to about 250,000 µm².
10. The device of any of statements 1-9, wherein each of the holes has an area of about 50 µm² to about 250,000 µm².
11. The device of any of statements 1-10, wherein the stencil, including the walls of the holes, is coated with a blocking agent to inhibit cell adhesion to the stencil.
12. The device of statement 11, wherein the blocking agent comprises Pluronics, polyethylene oxide, alginate, poly-N-isopropylacrylamide, bovine serum albumin, bisacrylamide, alginate, agarose, polyethylene glycol diacrylate, or any combination thereof.
13. The device of any of statements 1-12, wherein the substrate comprises glass, silicon, polyolefin, polystyrene, poly(alkyl)methacrylate, poly(alkyl)acrylate, poly(acrylamide), poly(carbonate), poly(ethylene glycol), poly(N-isopropyl acrylamide), polyacrylonitrile, poly(vinylacetate), poly(vinyl alcohol), a chlorine-containing polymer, poly(vinyl)chloride, polyoxymethylene, polycarbonate, polyamide, polyimide, polyurethane, polyvinylidene difluoride (PVDF), phenolic, amino-epoxy resin, polyester, polyether, polyethylene terephthalate (PET), polyglycolic acid (PGA), poly-(p-phenyleneterephthalamide), polyphosphazene, polypropylene, or a combination thereof.
14. The device of any of statements 1-13, wherein the stencil is permanently or reversibly covalently bonded to the substrate.
15. The device of any of statements 1-14, wherein the stencil and/or the substrate has been covalently modified with aminosilane to present surface amine groups, and the substrate and the stencil are crosslinked together.
16. The device of any of statements 1-15, wherein the substrate and the stencil are crosslinked together with sodium alginate.
17. The device of statement 16, wherein the alginate can be degraded enzymatically using alginate lyase to permit removal of the stencil.
18. The device of any of statements 1-17, in which the substrate comprises a porous membrane that prevents cellular flux but allows fluid flow.
19. The device of any of statements 1-18, wherein the substrate comprises a network of microfluidic channels beneath a membrane.
20. The device of any of statements 1-18, wherein the substrate comprises a network of microfluidic channels beneath a membrane, with one or more microchannels operably connected to one or more microwells.
21. The device of statement 19 or 20, wherein the network of microfluidic channels is operably connected to one or more reservoirs, each reservoir thereby operably connected to a microwell.
22. The device of statement 21, wherein one or more reservoirs each separately comprise one or more test compounds, drugs, proteins, oligonucleotides, nucleic acids, or a combination thereof.
23. The device of any of statements 19-22, wherein the network of microfluidic channels further comprises one or more micropump to remove and deliver fluids to one or more to microwells.
24. The device of any of statements 1-23, wherein the substrate comprises a coating of cell adhesion molecules.
25. The device of statement 24, wherein the cell adhesion molecules comprise fibronectin, alginate, E-selectin, gelatin, laminin, matrigel, collagen, fibrinogen, bisacrylamide, RGD peptides, PHSRN peptides, and DGEA peptides, and combinations thereof.
26. The device of any of statements 1-24, wherein the substrate is not coated with a blocking agent that inhibits cell adhesion.
27. The device of any of statements 1-26, wherein the substrate comprises a culture dish, or a multi-well culture dish having at least 4 wells, or 4 to 96 wells, with at least one device in each well.
28. The device of any of statements 1-27, further comprising a cell culture medium in the culture dish.
29. The device of any of statements 1-28, further comprising a cell culture medium in the microwells.
30. The device of any of statements 1-29, further comprising mammalian cells in the microwells.
31. The device of any of statements 1-30, further comprising a mixture of mammalian cell types in the microwells.
32. The device of statement 30 or 31, wherein the mixture of mammalian cell types typically present in a mammalian organ selected from the group consisting of heart, muscle, and neuronal tissue.
33. The device of any of statements 30-32, wherein the mixture of mammalian cell types comprises heart tissue cells selected from the group consisting of cardiomyocytes, fibroblasts, epithelial cells, endothelial cells, neuronal cells, myoblasts, and combinations thereof.
34. The device of any of statements 30-33, wherein the mixture of mammalian cell types comprises muscle tissue cells selected from the group consisting of skeletal muscle stem cells, myoblasts, myosatellite cells, epithelial cells, myoepithelial cells, endothelial cells, neuronal cells, fibroblasts, and combinations thereof.
35. The device of any of statements 30-34, wherein the mixture of mammalian cell types comprises neuronal tissue cells selected from the group consisting of neurons, neuronal progenitor cells, glial cells, actrocytes, basket cells, beta cells, medium spiny neuron cells, pukinje cells, renshaw cells, unipolar brush cells, granular cells, anterior horn cells, spindle cells, and combinations thereof.
36. The device of any of statements 30-35, further comprising cells that comprise a heterologous marker gene, a heterologous reporter gene, a mutant gene, or a combination thereof.
37. The device of statement 36, wherein the marker gene encodes a fluorescent protein.
38. The device of statement 36 or 37, wherein the reporter gene encodes a calcium-activated protein.
39. The device of any of statements 36-38, wherein the reporter gene encodes a GCaMP6f calcium protein that can exhibit a fluorescent signal to a single action potential and/or that can exhibit a fluorescent signal to each action potential in a series of action potentials.
40. The device of any of statements 36-39, wherein the mutant gene is contributes to a disease or condition.
41. The device of any of statements 36-40, wherein the mutant gene is in any of the following genes: ABCC9, ACTC1, ACTN2, ANKRD1, AKAP9, ANK2, BAGS, CACNA1C, CACNB2, CASQ2, CAV3, COX15, CRYAB, CSRP3, CTF1, DES, DMD, DNAJC19, DSC2, DSG2, DSP, DTNA, EYA4, FHL2, FKTN, FOXD4, GLA, KCNE1, KCNE2, KCNH2, KCNJ5, KCNJ8, KCNQ1, KCNQ2, LAMA4, LAMP2, LDB3, LMNA, MYBPC3, MYH6, MYH7, MYL2, MYL3, MYOZ2, NEXN, PKP2, PLN, PRKAG2, PSEN1, PSEN2, RBM20, RYR2, SCN5A, SDHA, SGCD, SNTA1, SYNE1, SYNE2, TAZ, TCAP, TMEM43, TMPO, TNNC1, TNNT2, TNNC1, TNNI3, TPM1, TRDN, TTN, TTR, VCL, or any combination thereof.

42. The device of any of statements 36-41, wherein the mutant gene is recombinantly introduced.
43. The device of any of statements 1-42, further comprising about 1000 to about 10,000 cells in at least one microwell.
44. The device of any of statements 1-43, further comprising about 2000 to about 9,500 cells, or about 3000 to about 9000 cells, or about 4000 to about 8500 cells, or about 5000 to about 8000 cells in at least one microwell.
45. The device of any of statements 1-44, further comprising mammalian cells in at least two adjacent holes of a microwell, wherein the at least two holes are joined by a canal.
46. The device of any of statements 1-45, wherein cells in the microwells grow and form three-dimensional tissues.
47. The device of any of statements 1-46, wherein cells in adjacent holes grow and align along the canal joining the adjacent holes.
48. The device of any of statements 1-47, wherein cells within the micro-tissues formed in the wells exhibit contractility with greater synchronicity than two-dimensional monolayers of the same cell type and composition.
49. The device of any of statements 1-48, wherein cells within the micro-tissues formed in the wells respond to drugs with greater synchronicity than two-dimensional monolayers of the same cell type and composition.
50. The device of any of statements 1-49, wherein cells within the micro-tissues formed in the wells exhibit chronotropic and/or inotropic responses to drugs and the responses are more synchronized compared to than two-dimensional monolayers of the same cell type and composition.
51. The device of any of statements 1-50, wherein cells within the micro-tissues formed in the wells exhibit an inotropic response to isoproterenol but a monolayer of cells of the same type and composition does not.
52. The device of any of statements 1-51, wherein the micro-tissues exhibit an increased maximal contraction velocity to verapamil at doses of at least 0.5 µM but a monolayer of cells of the same type and composition does not.
53. A method of inducing self-assembly of mammalian cells into one or more three-dimensional micro-tissues comprising seeding the mammalian cells into one or more microwells of the device of any of statements 1-52, and culturing the seeded cells within the microwells, to thereby induce the self-assembly of the mammalian cells into one or more micro-tissues.
54. The method of statement 53, wherein about 2000 to about 9,500 cells, or about 3000 to about 9000 cells, or about 4000 to about 8500 cells, or about 5000 to about 8000 cells are seeded into each of several microwells of the device.
55. The method of statement 53 or 54, wherein a mixture of cells are seeded into each of several microwells of the device.
56. The method of any of statements 53-55, wherein a mixture of mammalian cell types is seeded into each of several microwells of the device, each mixture comprising cells from a selected mammalian organ.
57. The method of statement 56, wherein the mammalian organ is selected from the group consisting of heart, muscle, and neuronal tissue.
58. The method of any of statements 55-57, wherein the mixture of mammalian cell types comprises heart tissue cells selected from the group consisting of cardiomyocytes, fibroblasts, epithelial cells, endothelial cells, neuronal cells, myoblasts, and combinations thereof.
59. The method of any of statements 55 to 58, wherein the mixture of mammalian cell types comprises muscle tissue cells selected from the group consisting of skeletal muscle stem cells, myoblasts, myosatellite cells, epithelial cells, myoepithelial cells, endothelial cells, neuronal cells, fibroblasts, and combinations thereof.
60. The method of any of statements 55-59, wherein the mixture of mammalian cell types comprises neuronal tissue cells selected from the group consisting of neurons, neuronal progenitor cells, glial cells, actrocytes, basket cells, beta cells, medium spiny neuron cells, pukinje cells, renshaw cells, unipolar brush cells, granular cells, anterior horn cells, spindle cells, and combinations thereof.
61. The method of any of statements 53-60, wherein the at least a portion of the mammalian cells comprise a heterologous marker gene, a heterologous reporter gene, a mutant gene, or a combination thereof.
62. The method of statement 61, wherein the marker gene encodes a fluorescent protein.
63. The method of statement 61 or 62, wherein the reporter gene encodes a calcium-activated protein.
64. The method of any of statements 61-63, wherein the reporter gene encodes a GCaMP6f calcium protein that can exhibit a fluorescent signal to a single action potential, and/or that can exhibit a fluorescent signal to each action potential in a series of action potentials.
65. The method of any of statements 61-64, wherein the mutant gene is contributes to a disease or condition.
66. The method of any of statements 61-65, wherein the mutant gene is in any of the following genes: ABCC9, ACTC1, ACTN2, ANKRD1, AKAP9, ANK2, BAG3, CACNA1C, CACNB2, CASQ2, CAV3, COX15, CRYAB, CSRP3, CTF1, DES, DMD, DNAJC19, DSC2, DSG2, DSP, DTNA, EYA4, FHL2, FKTN, FOXD4, GLA, KCNE1, KCNE2, KCNH2, KCNJ5, KCNJ8, KCNQ1, KCNQ2, LAMA4, LAMP2, LDB3, LMNA, MYBPC3, MYH6, MYH7, MYL2, MYL3, MYOZ2, NEXN, PKP2, PLN, PRKAG2, PSEN1, PSEN2, RBM20, RYR2, SCN5A, SDHA, SGCD, SNTA1, SYNE1, SYNE2, TAZ, TCAP, TMEM43, TMPO, TNNC1, TNNT2, TNNC1, TNNI3, TPM1, TRDN, TTN, TTR, VCL, or any combination thereof.
67. The method of any of statements 61-66, wherein the mutant gene is recombinantly introduced.
68. The method of any of statements 53-67, wherein seeding the mammalian cells into one or more microwells comprises settling the cells into the microwells via gravity.
69. The method of any of statements 53-68, wherein seeding the mammalian cells into one or more microwells comprises settling the cells into the microwells by fluid flow through a membrane at the bottom of the microwells.
70. The method of any of statements 53-69, wherein seeding the mammalian cells into one or more microwells comprises settling the cells into the microwells by applying a differential force across a membrane at the bottom of the microwells to draw fluid through the microwells and the membrane while retaining the cells in the microwells.
71. The method of any of statements 53-70, wherein the seeded cells are cultured for about 2 hours to about 14 days, or for about 1 day to about 10 days, or for about 2 days to 7 days, or for about 2 days to about 6 days, or for about 2 days to 5 days.
72. The method of any of statements 53-71, wherein the functional properties of the seeded cells change as the culture time increases.
73. The method of statement 71, wherein the functional properties comprise chronotropic and/or inotropic properties.
74. The method of statement 71 or 72, wherein the functional properties comprise chronotropic and/or inotropic responses to drugs.
75. The method of any of statements 53-74, further comprising introducing one or more test compound, drug, protein, oligonucleotide, nucleic acid, or a combination thereof into one or more of the microwells while the cells are cultured in the microwells.
76. The method of any of statements 53-75, further comprising determining whether cells are aligned in one or more canals of one or more of the microwells.
77. The method of any of statements 53-76, further comprising determining whether cells have formed three-dimensional structures in one or more canals or holes of the microwells.
78. The method of any of statements 53-77, further comprising determining whether cells are contracting along the longitudinal axis of one or more of the microwells.
79. The method of any of statements 53-78, further comprising determining micro-tissue morphology, genetic expression, contraction rate, contraction intensity, electrical activity, calcium transient amplitude, intracellular $Ca^{2+}$ level, cell size contractile force production, sarcomeric a-actinin distribution, or a combination thereof.
80. The method of any of statements 53-79, wherein cells within the micro-tissues formed in the microwells exhibit contractility with greater synchronicity than two-dimensional monolayers of the same cell type and composition.
81. The method of any of statements 53-80, wherein cells within the micro-tissues formed in the microwells respond to drugs with greater synchronicity than two-dimensional monolayers of the same cell type and composition.
82. The method of any of statements 53-81, wherein cells within the micro-tissues formed in the microwells exhibit chronotropic and/or inotropic responses to drugs that are more synchronized compared to than two-dimensional monolayers of the same cell type and composition.
83. The method of any of statements 53-82, wherein cells within the micro-tissues formed in the wells exhibit an inotropic response to isoproterenol but a monolayer of the animal cells does not.
84. The method of any of statements 53-83, wherein the micro-tissues exhibit an increased maximal contraction velocity to verapamil at doses of at least 0.5 μM but a monolayer of the animal cells does not.
85. The method of any of statements 53-84, further comprising culturing one or more micro-tissues in a medium containing a test compound, drug, oligonucleotide, nucleic acid, protein, or a combination thereof.
86. The method of any of statements 53-85, further comprising removing the stencil to generate intact micro-tissues.
87. The method of any of statements 53-86, further comprising cleaving, disrupting, or reversing covalent bonds between the stencil and the substrate, to allow removal of the stencil.
88. The method of any of statements 53-87, further comprising removing the stencil to generate intact micro-tissues that adhere to the substrate.
89. The method of any of statements 53-88, further comprising recovering cells from the microwells and determining expression of one or more mRNA or protein.
90. The method of any of statements 53-89, further comprising damaging one or more micro-tissues (e.g, by scoring or cutting through a portion of one or more microtissues, to thereby generate an injured tissue), embedding one or more micro-tissues, fixing one or more micro-tissues, freezing one or more micro-tissues, sectioning one or more micro-tissues, staining one or more micro-tissues, or any combination thereof.
91. The method of any of statements 53-90, wherein micro-tissues are present within a stencil when embedding one or more micro-tissues, fixing one or more micro-tissues, freezing one or more micro-tissues, sectioning one or more micro-tissues, staining one or more micro-tissues, or a combination thereof.
92. The method of any of statements 53-91, wherein the mammalian cells seeded in the microwells are wild type or mutant somatic cells.
93. The method of any of statements 53-92, wherein the mammalian cells seeded in the microwells were derived from induced pluripotent stem cells by differentiation of the induced pluripotent stem cells into a desired lineage.
94. The method of any of statements 53-93, wherein the mammalian cells seeded in the microwells are wild type or mutant somatic cells converted into cells of a different differentiation lineage.
95. A kit comprising the device of any of statements 1-52, and instructions for making and/or testing micro-tissues in the device(s).
96. A kit comprising a master patterning template, a substrate, a material for making a stencil, and instructions for assembling the device of any of statements 1-52.
97. The kit of statement 95 or 96, wherein the instructions include instructions for preparing the substrate for the stencil overlay, for coating the substrate with one or more cell adhesion agents, for making the (e.g. elastomeric) material that will form the stencil, for generating microwells in the (e.g. elastomeric) stencil material, for curing the (e.g. elastomeric) material of the stencils, for coating the stencils with a blocking agent, for seeding cells into the microwells of the devices, for using the devices to make micro-tissues, for introducing test compounds, oligonucleotides, nucleic acids, proteins, or a combination thereof into the microwells, for testing and evaluating micro-tissues in the devices, for removing the stencils (with or without micro-tissues in the stencils), for testing and evaluating micro-tissues removed from the devices, or any combination thereof.

98. The kit of any of statements 95-97, further comprising one or more containers that comprise cells for generating micro-tissues.

99. The kit of statement 98, wherein the containers comprise cells for generating micro-tissue disease models, and optionally one or more separate containers comprising cells for generating control micro-tissues.

100. The kit of any of statements 95-99, wherein the instructions include directions for mixing appropriate cell types to generate healthy and/or mutant or diseased micro-tissues of various organ or tissue types, directions on how to test disease model micro-tissues in the presence and absence of test compounds, or a combination thereof.

The specific devices, methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The following claims summarize aspects of the invention.

What is claimed:

1. A method of inducing self-assembly of mammalian cells into one or more dog-bone shaped micro-tissues comprising
    seeding the mammalian cells into one or more microwells of a device comprising
        a cell adhesion substrate; and
        a removable elastomeric stencil overlay comprising one or more cut-out patterned microwells comprising two or more circular, oval, rectangular, square, V-shaped, or triangular holes, each hole joined to an adjacent hole by a canal; and
    culturing the seeded cells within the microwells, to thereby induce self-assembly of the mammalian cells into one or more dog-bone micro-tissues shaped within adjacent holes and along the canal joining the adjacent holes;
    wherein the cell adhesion substrate binds cells within at least the holes of the cut-out pattern.

2. The method of claim 1, wherein about 2000 to about 9500 cells are seeded into each of several microwells of the device.

3. The method of claim 1, wherein each of the microwells has a depth of at least 250 μm or at least 500 μm.

4. The method of claim 1, wherein at least one of the microwells has at least two square holes with a side length "L" of 250 μm to 1000 μm, and the canal joining the two square holes has a longitudinal length "X" of 250-1000 μm a transverse width "Y" of 50-200μm.

5. The method of claim 1, wherein the ratio of L to Y is at least five.

6. The method of claim 1, wherein the seeded cells are a mixture of mammalian cell types typically present in a mammalian organ.

7. The method of claim 6, wherein the mammalian organ is selected from the group consisting of heart, muscle, and neuronal tissue.

8. The method of claim 1, wherein the mammalian cells comprise a heterologous marker gene, a heterologous reporter gene, a mutant gene, or a combination thereof.

9. The method of claim 1, wherein the mammalian cells comprise a marker gene encodes a fluorescent protein.

10. The method of claim 1, wherein the mammalian cells comprise a mutation in any of the following genes: ABCC9, ACTC1, ACTN2, ANKRD1, AKAP9, ANK2, BAG3, CACNA1C, CACNB2, CASQ2, CAV3, COX15, CRYAB, CSRP3, CTF1, DES, DMD, DNAJC19, DSC2, DSG2, DSP, DTNA, EYA4, FHL2, FKTN, FOXD4, GLA, KCNE1, KCNE2, KCNH2, KCNJ5, KCNJ8, KCNQ1, KCNQ2, LAMA4, LAMP2, LDB3, LMNA, MYBPC3, MYH6, MYH7, MYL2, MYL3, MYOZ2, NEXN, PKP2, PLN, PRKAG2, PSEN1, PSEN2, RBM20, RYR2, SCN5A, SDHA, SGCD, SNTA1, SYNE1, SYNE2, TAZ, TCAP, TMEM43, TMPO, TNNC1, TNNT2, TNNC1, TNNI3, TPM1, TRDN, TTN, TTR, VCL, or any combination thereof.

11. The method of claim 1, wherein seeding the mammalian cells comprises settling the cells into the microwells by gravity or by fluid flow through a membrane at the bottom of the microwells.

12. The method of claim 1, further comprising introducing a test compound, oligonucleotide, nucleic acid, protein, or a combination thereof into one or more microwells while culturing the seeded cells within the microwells.

13. The method of claim 1, further comprising introducing a test compound, oligonucleotide, nucleic acid, protein, or a combination thereof into one or more microwells via membrane at the bottom of the microwells, where the microwells are operably connected to a network of microfluidic channels for introduction of the test compound, oligonucleotide, nucleic acid, protein, or a combination thereof.

14. The method of claim 1, further comprising determining whether cells are aligned in one or more canals of one or more of the microwells.

15. The method of claim 1, further comprising determining whether cells have formed dog-bone shaped structures in one or more canals or holes of the microwells.

16. The method of claim 1, further comprising determining whether cells are contracting along the longitudinal axis of one or more of the microwells.

17. The method of claim 1, further comprising culturing one or more micro-tissues in a medium containing a test agent.

18. The method of claim 1, further comprising determining micro-tissue morphology, genetic expression, contraction rate, contraction intensity, electrical activity, calcium transient amplitude, intracellular $Ca^{2+}$ level, cell size contractile force production, sarcomeric α-actinin distribution, or a combination thereof.

19. The method of claim 1, wherein cells within the micro-tissues formed in the microwells exhibit contractility with greater synchronicity than two-dimensional monolayers of the same cell type and composition.

20. The method of claim 1, wherein cells within the micro-tissues formed in the microwells respond to drugs with greater synchronicity than two-dimensional monolayers of the same cell type and composition.

21. The method of claim 1, wherein cells within the micro-tissues formed in the microwells exhibit more synchronized chronotropic and/or inotropic responses to drugs compared to than two-dimensional monolayers of the same cell type and composition.

22. The method of claim 1, further comprising removing the stencil to generate intact micro-tissues.

23. The method of claim 1, further comprising recovering cells from the microwells and determining expression of one or more mRNA or protein.

24. The method of claim 1, further comprising immersing one or more micro-tissues in a support medium, damaging one or more micro-tissues, embedding one or more micro-tissues, fixing one or more micro-tissues, fixing one or more micro-tissues, freezing one or more micro-tissues, sectioning one or more micro-tissues, staining one or more micro-tissues, or a combination thereof.

25. The method of claim 1, wherein the mammalian cells seeded in the microwells are wild type or mutant somatic cells converted into induced pluripotent stem cells and then differentiated into a desired lineage.

* * * * *